United States Patent
Affholter et al.

(10) Patent No.: US 6,605,430 B1
(45) Date of Patent: Aug. 12, 2003

(54) DNA SHUFFLING OF MONOOXYGENASE GENES FOR PRODUCTION OF INDUSTRIAL CHEMICALS

(75) Inventors: Joseph A. Affholter, Morgan Hill, CA (US); S. Christopher Davis, San Francisco, CA (US); Sergey A. Selifonov, Los Altos, CA (US)

(73) Assignee: Maxygen, Inc., Redwood, CA (US)

( * ) Notice: Subject to any disclaimer, the term of this patent is extended or adjusted under 35 U.S.C. 154(b) by 0 days.

(21) Appl. No.: 09/373,928

(22) Filed: Aug. 12, 1999

Related U.S. Application Data

(60) Provisional application No. 60/096,271, filed on Aug. 12, 1998, and provisional application No. 60/130,810, filed on Apr. 23, 1999.

(51) Int. Cl.$^7$ ............... C12Q 1/68; C07H 21/02
(52) U.S. Cl. ............... 435/6; 435/69.1; 435/183; 435/189; 435/DIG. 2; 435/DIG. 14; 435/DIG. 17; 536/23.1; 536/23.2
(58) Field of Search ............... 435/6, 5, 69.1, 435/235.1, 320.1, DIG. 1, DIG. 2, DIG. 3, DIG. 14, DIG. 17; 935/76, 77, 78, 14, 180

(56) References Cited

U.S. PATENT DOCUMENTS

| | | |
|---|---|---|
| 5,512,463 A | 4/1996 | Stemmer |
| 5,514,588 A | 5/1996 | Varadaraj |
| 5,605,793 A | 2/1997 | Stemmer |
| 5,763,239 A | 6/1998 | Short et al. |
| 5,789,228 A | 8/1998 | Lam et al. |
| 5,811,238 A * | 9/1998 | Stemmer et al. ............... 435/6 |
| 5,814,473 A | 9/1998 | Warren et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,876,997 A | 3/1999 | Kretz |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,985,646 A | 11/1999 | Murphy et al. |

FOREIGN PATENT DOCUMENTS

| | | |
|---|---|---|
| EP | 0911396 A2 | 4/1999 |
| EP | 0911396 A3 | 5/1999 |
| EP | 0934999 A1 | 8/1999 |
| WO | WO 95/22625 | 8/1995 |
| WO | WO 95/34679 | 12/1995 |
| WO | WO 97/07205 | 2/1997 |
| WO | WO 97/20078 | 6/1997 |
| WO | WO 97/25410 | 7/1997 |
| WO | WO 97/35957 | 10/1997 |
| WO | WO 97/35966 | 10/1997 |
| WO | WO 97/44361 | 11/1997 |
| WO | WO 97/48416 | 12/1997 |
| WO | WO 97/48717 | 12/1997 |
| WO | WO 97/48794 | 12/1997 |
| WO | WO 98/00526 | 1/1998 |
| WO | WO 98/01581 | 1/1998 |
| WO | WO 98/13485 | 4/1998 |
| WO | WO 98/13487 | 4/1998 |
| WO | WO 98/24799 | 6/1998 |
| WO | WO 98/27230 | 6/1998 |
| WO | WO 98/28416 | 7/1998 |
| WO | WO 98/31837 | 7/1998 |
| WO | WO 98/36080 | 8/1998 |
| WO | WO 98/41622 | 9/1998 |
| WO | WO 98/41623 | 9/1998 |
| WO | WO 98/41653 | 9/1998 |
| WO | WO 98/42832 | 10/1998 |
| WO | WO 98/48034 | 10/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/60096 | 11/1999 |
| WO | WO 99/65927 | 12/1999 |

OTHER PUBLICATIONS

Joo, Hyun; Lin, Zhanglin; and Arnold, Frances H. "Laboratory evolution of peroxide–mediated cytochrome P450 hydroxylation" Nature. vol. 399. (Jun. 1999) pp. 670–673.

Aoyama T, et al. (1989) *Journal Of Biological Chemistry*, 264 (18): 10388–10395.

(List continued on next page.)

*Primary Examiner*—Padmashri Ponnaluri
(74) *Attorney, Agent, or Firm*—Donald J. Pochopien; Sharon M. Fujita; Norman J. Kruse

(57) ABSTRACT

This invention provides improved monoxygenases, dehydrogenases, and transferases that are useful for the biocatalytic synthesis of compounds such as α-hydroxycarboxylic acids, and aryl- and alkyl-hydroxy compounds. The polypeptides provided herein are improved in properties such as regioselectivity, enzymatic activity, stereospecificity, and the like. Methods for obtaining recombinant polynucleotides that encode these improved polypeptides are also provided, as are organisms that express the polypeptides and are thus useful for carrying out said biocatalytic syntheses. Also provided by the invention are methods for increasing said solvent resistance of organisms that are used in the synthetic methods.

9 Claims, 11 Drawing Sheets

OTHER PUBLICATIONS

Crameri et al. (1998) *Nature*, 391:288–291.
Dierks E. A. etal. (1998) *Journal of Biological Chemistry* 273(36):23055–23061.
Gotoh, O. (1992) *Journal of Biological Chemistry* 267(1): 443–478.
Lewis, D. F. V. & Lake B. G. (1997) *Xenobiotica*, 27(5): 443–478.
O'Keefe D. P. et al (1991) *Molecular Microbiology* 5(9): 2099–2105.
Panke, S. et al. (1998) *Applied and Environmental Microbiology*, 64(6): 2032–2043.
Pompon, D. & Nicholas A. (1989) *Gene*, 83(1):15–24.
Ruettinger, R. T. et al. (1989) *Journal of Biological Chemistry*, 264(19): 10987–10995.
Sevrioukova, I. F. & Peterson, J. A. (1995) *Biochimie*, 77: 562–572.
Shimoji,M. et al. (1998) *Biochemistry*, 37(25): 9959–8852.
Valetti F. et al. (1998) *Biosensors and Bioelectronics*, 13: 675–685.
Wackett, L. P. (1998) *Annals New York Academy of Science*, 864:142–152.
Watanabe, I. & Serizawa, N. (1998) *Gene*, 210(1):109–116.
Database EMBL Nucleotide & Protein Sequences, Jun. 10, 1997, AP002124402, Hinxton GB.
Database WPI, Section Ch, Week 199314, Derwent Publication Ltd., London, GB: Class B04, An 1993–111879, XP002124410.
Chang, C., et al. (1999) "Evolution of a cytokine using DNA family shuffling." *Nature Biotechnology* 17:793–797.
Christians, F.C. et al., (1999) "Directed evolution of thymidine kinase for AZT phosphorylation using DNA family shuffling." *Nature Biotechnology* 17:259–264.
Crameri et al., (1993) "10(20)–Fold aptamer library amplification without gel purification," *Nuc. Acids Res.* 21(18):4410.
Crameri, A. & Stemmer, W.P.C. (1995) "Combinatorial multiple cassette mutagenesis creates all the permutations of mutant and wildtype cassettes." *Biotechniques* 18:194–195.
Crameri, A. et al. (1996) "Construction and evolution of antibody–phage libraries by DNA shuffling." *Nature Medicine* 2:100–103.
Crameri, A. et al., (1997) "Molecular evolution of an arsenate detoxification pathway by DNA shuffling." *Nature Biotechnology* 15:436–438.
Gates, C.M. et al., (1996) "Affinity selective isolation of ligands from peptide libraries through display on a lac repressor headpiece dimer". *Journal of Molecular Biology* 255:373–386.
Minshull, J., Stemmer, W.P.C. (1999) "Protein evolution by molecular breeding." *Current Opinion in Chemical Biology* 3:284–290.
Ness, J. et al., (1999) "DNA shuffling of subgenominc sequences of subtilisin." *Nature Biotechnology* 17:893–896.
Patten, P.A. et al., (1997) "Application of DNA Shuffling to Pharmaceuticals and Vaccines." *Current Opinion in Biotechnology* 8:724–733.
Stemmer, W.P.C. (1996) "Sexual PCR and Assembly PCR." In: *The Encyclopedia of Molecular Biology*. VCH Publishers, New York. pp. 447–457.
Stemmer, W.P.C. & Soong, N.W. (1999) "Molecular breeding of viruses for targeting and other clinical properties." *Tumor Targeting* 4:59–62.
Zhang, J. et al., (1997) "Directed evolution of an effective fucosidase from a galactosidase by DNA shuffling and screening." *Proceedings of the National Academy of Sciences, USA* 94:4504–4509.
Aono et al., (1998) *J. Bacteriol.* 180:938–944.
Beltrametti, et al., (1997) *Appl. Environ. Microbiol.* 63(6):2232–2239.
Clever (1997) *EMBO J.* 16:2535–2544.
Crameri et al. (1996) *Nature Biotechnolog* 14:315–319.
Crameri et al. (1996) *Nature Medicine* 2(1): 1–3.
Dierks et al., (1998) *J. Biol. Chem.* 273(36): 23055–61.
Drauz & Waldmann eds. (1995) Enzyme Catalysis in Organic Synthesis, vol. II, Chapter B.6.1.4, VCH Publishers, Inc. 1995.
Duport et al., (1998) *Nature Biotechnol.* 16:186.
Gotoh, (1992) *J. Biol. Chem.* 267:83–90.
Halpert et al., (1998) *Drug Metabolism and Disposition* 26(12):1223–1231.
Iding et al. (1998) *Biochem. Biophys. Acta* 1358:307–313.
Itoh et al., (1996) *Biosci. Biotechnol. Biochem.* 60(11): 1826–1830.
Kieboom et al., (1998) *J. Biol. Chem.* 273: 85–91.
Kiianitsa (1997) *Proc. Natl. Acad. Sci. U.S.A.* 94:7837–7840.
Kim et al. (1998) *J. Bacteriol.* 180: 3692–2696.
Kok et al., (1989) *J. Biol. Chem.* 264(10): 5435–5441.
Kok et al., (1989) *J. Biol. Chem.* 264(10): 5442–5451.
Li & Poulos (1997) *Nature Struc. Biol.* 4: 140–146.
Li et al., (1998) *J. Bacteriol.* 180:2987–2991.
Lee et al. (1996) *Biochem. Biophys. Res. Commun.* 218(1):17–21.
Loida and Sligar (1993) *Protein Eng.* 6(2): 207–212.
Marconi, et al. (1996) *Appl. Environ. Microbiol.* 62(1):121–127.
Matsumoto et al. (1992) *Chem. Pharm. Bull. (Tokyo)* 40(7): 1721–1726.
Matsumoto et al. (1994) *Biol. Chem. Bull.* 17(11):1441–1445.
Matsumoto et al. (1995) *Chem. Pharm. Bull. (Tokyo)* 43(2):216–222.
Namsaraev (1997) *Mol. Cell. Biol.* 17:5359–5368.
O'Connor, et al., (1997) *Appl. Environ. Microbiol.* 63(11):4287–4291.
Pinkart and White (1997) *J. Bacteriol.* 179:4219–4226.
Pompon et al., (1996) *Methods Enzymol.* 272:51.
Ramos et al., (1998) *J. Bacteriol.* 180: 3323–3329.
Sevrioukova et al., (1999) *PNAS* 96:1863–1868.
Stemmer (1994) *Nature* 370:389–391.
Stemmer (1994) *Proc. Natl. Acad. Sci. U.S.A.* 91:10747–10751.
Stemmer (1995) *Bio/Technology* 13:549–553.
Stemmer et al. *Gene* 164:49–53.
Stemmer (1995) *Science* 270:1510.
Sung (1997) *Genes Dev.* 11:1111–1121.
Van Beilen et al (1992) *Mol. Microbiol.* 6(21): 3121–3136.
Velasco, et al., (1998) *J. Bacteriol.* 180(5): 1063–1071.
Watanabe et al., (1995) *Gene* 163: 81–85.
White, et al. (1997) *J. Bacteriol.* 179: 6122–6126.
Wold (1997) *Annu. Rev. Biochem.* 66:61–92.

* cited by examiner

FATTY ACIDS

→(n=0-18, MO)→  →(MO)→ DIACIDS

→(n=0-18, MO)→ n-ALKANES

Fisher-Tropesh Waxe. n-alkanes C20-C60

→(n=0-18, MO)→

↓ MO

→(n=0-10, MO)→

AROMATICS II

TERPENOIDS

LINEAR OLEFINS

DNA SHUFFLING OF MONOOXYGENASE GENES FOR PRODUCTION OF INDUSTRIAL CHEMICALS

CROSS REFERENCE TO RELATED APPLICATIONS

This application claims priority under 35 U.S.C. §119(e) to U.S. Provisional Application Ser. No. 60/096,271, and U.S. Provisional Application Ser. No. 60/130,810, by Joseph A. Affholter, filed on Aug. 12, 1998 and Apr. 23, 1999, respectively. This application is related to the copending application titled DNA SHUFFLING OF DIOXYGENASE GENES FOR PRODUCTION OF INDUSTRIAL CHEMICALS by Sergey A. Selifonov, filed on an even day herewith. This application is also related to U.S. Provisional Application Ser. No. 60/096,280, filed Aug. 12, 1998, U.S. Provisional Application Ser. No. 60/111,146, filed Dec. 7, 1998, U.S. Provisional Application Ser. No. 60/112,746, filed Dec. 17, 1998. The disclosures of each the above-referenced applications are incorporated herein by reference in their entirety for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention pertains to the shuffling of nucleic acids to achieve or enhance industrial production of chemicals by monooxygenase genes.

BACKGROUND OF THE INVENTION

Organic acids, alcohols, aldehydes and epoxides are important classes of industrial chemicals. Typically, these products are generated by successive oxidation of inexpensive, high volume saturated and unsaturated hydrocarbons (ethane, propane, butane, etc. and ethene, propene, butene, etc.) and simple aromatics such as benzene, ethyl benzene, naphthalene, styrene and toluene.

Monooxygenases (MOs) such as the P450 oxygenases, heme-dependent peroxidases, iron-sulfur MOs and quinone-dependent MOs typically catalyze limited oxidation of these basic chemical building blocks. While potentially interesting from an industrial standpoint, these enzymes typically exhibit neither the physical robustness nor sufficient turnover numbers to make them usable as industrial catalysts. In addition, regeneration of a reduced heme is required following each catalytic turnover. Biologically, the necessary heme reduction is mediated in the P450 family of enzymes by NAD(P)H, an expensive and impractical redox partner for most industrial chemistries.

Surprisingly, the present invention provides a method for providing enzymes with higher activity, high physical stability and robustness. Also surprisingly, the present invention provides a means of generating NADPH-independent monooxygenase activity in the presence of peroxide co-substrates (as well as other inexpensive cofactors) thereby solving each of the problems outlined above, as well as providing a variety of other features which will be apparent upon review.

SUMMARY OF THE INVENTION

In the present invention, DNA shuffling is used to generate new or improved monooxygenase genes. These monooxygenase genes are used to provide monooxygenase enzymes, especially for industrial processes. These new or improved genes have surprisingly superior properties as compared to naturally occurring monooxygenase genes.

In the methods for obtaining monooxygenase genes, a plurality of parental forms (homologs) of a selected nucleic acid are recombined. The selected nucleic acid is derived either from one or more parental nucleic acid(s) which encodes a monooxygenase enzyme, or a fragment thereof, or from a parental nucleic acid which does not encode monooxygenase, but which is a candidate for DNA shuffling to develop monooxygenase activity. The plurality of forms of the selected nucleic acid differ from each other in at least one (and typically two or more) nucleotides, and, upon recombination, provide a library of recombinant monooxygenase nucleic acids. The library can be an in vitro set of molecules, or present in cells, phage or the like. The library is screened to identify at least one recombinant monooxygenase nucleic acid that exhibits distinct or improved monooxygenase activity compared to the parental nucleic acid or nucleic acids.

Many formats for libraries of nucleic acids are known in the art and each of these formats is generally applicable to the libraries of the present invention. For example, basic texts generally disclosing library formats of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

In a preferred embodiment, the starting DNA segments are first recombined by any of the formats described herein to generate a diverse library of recombinant DNA segments. Such a library can vary widely in size from having fewer than 10 to more than $10^5$, $10^7$, or $10^9$ members. In general, the starting segments and the recombinant libraries generated include full-length coding sequences and any essential regulatory sequences, such as a promoter and polyadenylation sequence, required for expression. However, if this is not the case, the recombinant DNA segments in the library can be inserted into a common vector providing the missing sequences before performing screening/selection.

If the sequence recombination format employed is an in vivo format, the library of recombinant DNA segments generated already exists in a cell, which is usually the cell type in which expression of the enzyme with altered substrate specificity is desired. If sequence recombination is performed in vitro, the recombinant library is preferably introduced into the desired cell type before screening/selection. The members of the recombinant library can be linked to an episome or virus before introduction or can be introduced directly. In some embodiments of the invention, the library is amplified in a first host, and is then recovered from that host and introduced to a second host more amenable to expression, selection, or screening, or any other desirable parameter.

The manner in which the library is introduced into the cell type depends on the DNA-uptake characteristics of the cell type (e.g., having viral receptors, being capable of conjugation, or being naturally competent). If the cell type is not susceptible to natural and chemical-induced competence, but is susceptible to electroporation, one preferably employs electroporation. If the cell type is not susceptible to electroporation as well, one can employ biolistics. The biolistic PDS-1000 Gene Gun (Biorad, Hercules, Calif.) uses helium pressure to accelerate DNA-coated gold or tungsten microcarriers toward target cells. The process is applicable to a wide range of tissues, including plants, bacteria, fungi, algae, intact animal tissues, tissue culture cells, and animal embryos. One can employ electronic pulse delivery, which is essentially a mild electroporation format for live tissues in animals and patients. Zhao, *Advanced Drug Delivery Reviews* 17:257–262 (1995). Novel methods for making cells competent are described in co-pending application U.S. patent application Ser. No. 08/621,430, filed Mar. 25, 1996. After introduction of the library of recombinant DNA genes, the cells are optionally propagated to allow expression of genes to occur.

In selecting for monooxygenase activity, a candidate shuffled DNA can be tested for encoded monooxygenase activity in essentially any synthetic process. Common processes that can be screened include screening for alkane oxidation (e.g., hydroxylation, formation of ketones, aldehydes, etc.), screening for alkene epoxidation, aromatic hydroxylation, N-dealkylation (e.g., of alkylamines), S-dealkylation (e.g., of reduced thio-organics), O-dealkylation (e.g., of alkyl ethers), oxidation of aryloxy phenols, conversion of aldehydes to acids, alcohols to aldehydes or ketones, dehydrogenation, decarbonylation, oxidative dehalogenation of haloaromatics and halohydrocarbons, Baeyer-Villiger monoxygenation, modification of cyclosporins, hydroxylation of mevastatin, hydroxylation of erythromycin, N-hydroxylation, sulfoxide formation, hydroxylation of fatty acids, hydroxylation of terpenes or oxygenation of sulfonylureas. Other oxidative transformations will be apparent to those of skill in the art.

Similarly, instead of, or in addition to, testing for an increase in monooxygenase specific activity, it is also desirable to screen for shuffled nucleic acids which produce higher levels of monooxygenase nucleic acid or enhanced or reduced recombinant monooxygenase polypeptide expression or stability encoded by the recombinant monooxygenase nucleic acid.

A variety of screening methods can be used to screen a library, depending on the monooxygenase activity for which the library is selected. By way of example, the library to be screened can be present in a population of cells. The library is selected by growing the cells in or on a medium comprising the chemical or compound to be oxidized or reduced and selecting for a detected physical difference between the oxidized or reduced form of the chemical or compound and the non-oxidized or reduced form of the chemical or compound, either in the cell, or the extracellular medium.

Iterative selection for monooxygenase nucleic acids is also a feature of the invention. In these methods, a selected nucleic acid identified as encoding monooxygenase activity can be shuffled, either with the parental nucleic acids, or with other nucleic acids (e.g., mutated forms of the selected nucleic acid) to produce a second shuffled library. The second shuffled library is then selected for one or more form of monooxygenase activity, which can be the same or different than the monooxygenase activity previously selected. This process can be iteratively repeated as many times as desired, until a nucleic acid with optimized properties is obtained. If desired, any monooxygenase nucleic acid identified by any of the methods herein can be cloned and, optionally, expressed.

The invention also provides methods of increasing monooxygenase activity by whole genome shuffling. In these methods, a plurality of genomic nucleic acids are shuffled in a cell (in whole cell shuffling, entire genomes are shuffled, rather than specific sequences). The resulting shuffled nucleic acids are selected for one or more monooxygenase traits. The genomic nucleic acids can be from a species or strain different from the cell in which monooxygenase activity is desired. Similarly, the shuffling reaction can be performed in cells using genomic DNA from the same or different species, or strains. Strains or enzymes exhibiting enhanced MO activity can be identified.

The distinct or improved monooxygenase activity encoded by a nucleic acid identified after shuffling can encode one or more of a variety of properties, including: an increased ability to chemically modify the monooxygenase target, an increase in the range of monooxygenase substrates which the distinct or improved nucleic acid operates on, an increase in the chemoselectivity of a polypeptide encoded by the nucleic acid, an increase in the regioselectivity of a polypeptide encoded by the nucleic acid, an increase in the stereoselectivity of a polypeptide encoded by the nucleic acid, an increased expression level of a polypeptide encoded by the nucleic acid, a decrease in susceptibility of a polypeptide encoded by the nucleic acid to protease cleavage, a decrease in susceptibility of a polypeptide encoded by the nucleic acid to high or low pH levels, a decrease in susceptibility of the protein encoded by the nucleic acid to high or low temperatures, a decrease in peroxide-mediated enzyme inactivation, a decrease in toxicity to a host cell of a polypeptide encoded by the selected nucleic acid, the ability to use low-cost reducing partners (rather than NAD(P)H), and a reduction in the sensitivity of the polypeptide and/or an organism expressing the polypeptide to inactivation by organic solvents and the feedstocks for and products of the enzymatic oxidations, and The selected nucleic acids to be shuffled can be from any of a variety of sources, including synthetic or cloned DNAs. Exemplary targets for recombination include nucleic acids encoding P450 monooxygenases, nucleic acids encoding heme-dependent peroxidases, nucleic acids encoding iron sulfur monooxygenases, nucleic acids encoding quinone-dependent monooxygenases, and the like. Typically, shuffled nucleic acids are cloned into expression vectors to achieve desired expression levels.

In addition to shuffling monooxygenase nucleic acids, it is occasionally desirable to produce shuffled nucleic acids which produce oxidizing/reducing equivalents in forms other than $O_2$, $H_2O_2$ and NADPH, such as peroxides. Shuffled monooxygenase and oxidase ($H_2O_2$) nucleic acids can be co-expressed in a single system to provide both monooxygenase activity and peroxide in a single system.

One feature of the invention is production of libraries and shuffling mixtures for use in the methods as set forth above. For example, a phage display library comprising shuffled forms of a nucleic acid is provided. Similarly, a shuffling mixture comprising at least three homologous DNAs, each of which is derived from a nucleic acid encoding a polypeptide or polypeptide fragment is provided. These polypeptides can be, for example, P450 monooxygenases, heme-dependent peroxidases, iron sulfur monooxygenases, quinone-dependent monooxygenases, and the like.

Isolated nucleic acids identified by selection of the libraries in the methods above are also a feature of the invention.

Figure 1:
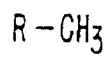
FIG. 1. Schematic showing functional group insertion and modification using a monooxygenase.
Figure 1:
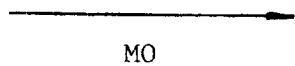
Figure 1:
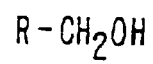
Figure 1:
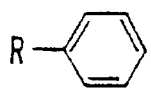
Figure 1:
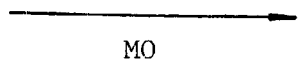
Figure 1:
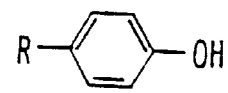
Figure 1:
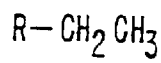
Figure 1:
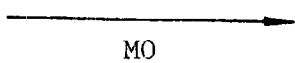
Figure 1:
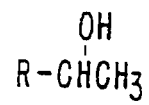
Figure 1:
Figure 1:
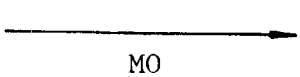
Figure 1:
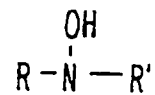
Figure 1:
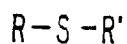
Figure 1:
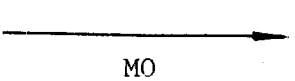
Figure 1:
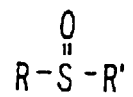
Figure 1:
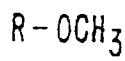
Figure 1:
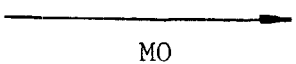
Figure 1:
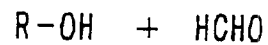

The absolute configuration of the chiral centers is not indicated in these Figures. The chiral centers of the chiral compounds can be R, S, or a mixture of these configurations.

DETAILED DESCRIPTION OF THE INVENTION AND THE PREFERRED EMBODIMENTS

Abbreviations

"AHA" refers to an α-hydroxycarboxylic acid.

"HCA" refers to a hydroxylated aromatic carboxylic acid

"MO" refers to a monooxygenase.

Definitions

Unless clearly indicated to the contrary, the following definitions supplement definitions of terms known in the art.

A "recombinant" nucleic acid is a nucleic acid produced by recombination between two or more nucleic acids, or any nucleic acid made by an in vitro or artificial process. The term "recombinant" when used with reference to a cell indicates that the cell includes (and optionally replicates) a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell where the genes are modified and re-introduced into the cell by artificial means. The term also encompasses cells that contain a nucleic acid endogenous to the cell that has been artificially modified without removing the nucleic acid from the cell; such modifications include those obtained by gene replacement, site-specific mutation, and related techniques.

A "recombinant dioxygenase nucleic acid" is a recombinant nucleic acid encoding a protein or RNA which confers dioxygenase activity to a cell when the nucleic acid is expressed in the cell.

A "plurality of forms" of a selected nucleic acid refers to a plurality of homologs of the nucleic acid. The homologs can be from naturally occurring homologs (e.g., two or more homologous genes) or by artificial synthesis of one or more nucleic acids having related sequences, or by modification of one or more nucleic acid to produce related nucleic acids. Nucleic acids are homologous when they are derived, naturally or artificially, from a common ancestor sequence. During natural evolution, this occurs when two or more descendent sequences diverge from a parent sequence over time, i.e., due to mutation and natural selection. Under artificial conditions, divergence occurs, e.g., in one of two ways. First, a given sequence can be artificially recombined with another sequence, as occurs, e.g., during typical cloning, to produce a descendent nucleic acid. Alternatively, a nucleic acid can be synthesized de novo, by synthesizing a nucleic acid which varies in sequence from a given parental nucleic acid sequence.

When there is no explicit knowledge about the ancestry of two nucleic acids, homology is typically inferred by sequence comparison between two sequences. Where two nucleic acid sequences show sequence similarity it is inferred that the two nucleic acids share a common ancestor. The precise level of sequence similarity required to establish homology varies in the art depending on a variety of factors. For purposes of this disclosure, two sequences are considered homologous where they share sufficient sequence identity to allow recombination to occur between two nucleic acid molecules. Typically, nucleic acids require regions of close similarity spaced roughly the same distance apart to permit recombination to occur.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a dioxygenase, or the amino acid sequence of the dioxygenase) refers to two or more sequences or subsequences that have at least about 60%, preferably 80%, most preferably 90–95% nucleotide or amino acid residue identity, when compared and aligned for maximum correspondence, as measured using one of the following sequence comparison algorithms or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al.,

*J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical/homologous is that the two molecules hybridize to each other under stringent conditions. The phrase "hybridizing specifically to," refers to the binding, duplexing, or hybridizing of a molecule only to a particular nucleotide sequence under stringent conditions, including when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen LABORATORY TECHNIQUES IN BIOCHEMISTRY AND MOLECULAR BIOLOGY—HYBRIDIZATION WITH NUCLEIC ACID PROBES part I chapter 2 (1993) "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to unrelated sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A further indication that two nucleic acid sequences or polypeptides are substantially identical/homologous is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two peptides differ only by conservative substitutions.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another:

Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations." Sequences that differ by conservative variations are generally homologous.

A "subsequence" refers to a sequence of nucleic acids or amino acids that comprise a part of a longer sequence of nucleic acids or amino acids (e.g., polypeptide) respectively.

The term "gene" is used broadly to refer to any segment of DNA associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have desired parameters.

The term "isolated", when applied to a nucleic acid or protein, denotes that the nucleic acid or protein is essentially free of other cellular components with which it is associated in the natural state.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Cassol et al. (1992); Rossolini et al., *Mol. Cell. Probes* 8:91–98 (1994)). The term nucleic acid is generic to the terms "gene", "DNA," "cDNA", "oligonucleotide," "RNA," "mRNA," "polynucleotide" and the like.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

A nucleic acid is "operably linked" when it is placed into a functional relationship with another nucleic acid sequence. For instance, a promoter or enhancer is operably linked to a coding sequence if it increases the transcription of the coding sequence.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "NAD(P)H" is used herein to refer to the reducing agents, NADH and NADPH.

"Regioselectivity" is used herein to refer to the ability to discriminate between different positions of the monooxygenase target.

"Chemoselectivity" is used herein to refer to the ability to discriminate between two or more potential sites of action in the monooxygenase target (e.g. alkyl hydroxylation in the presence of an epoxide and the like).

"Stereoselectivity" is used herein to refer to the ability to discriminate between enantiomeric sites in the monooxygenase target.

"Alkyl" refers to straight- and branched-chain, saturated and unsaturated hydrocarbons. "Lower alkyl", as used herein, refers to "alkyl" groups having from about 1 to about 6 carbon atoms.

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, napthyl, biphenyl, diphenylmethyl and benzophenone among others. The term "aryl" encompasses "arylalkyl."

The term "alkylarene" is used herein to refer to a subset of "aryl" in which the aryl group is substituted with an alkyl group as defined herein.

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "acyl" is used to describe a ketone substituent, —C(O)R, wherein R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to describe primary amines, R—$NH_2$, wherein R is alkyl or substituted alkyl, aryl or substituted aryl as defined herein.

The term "alkoxy" is used herein to refer to the —OR group, wherein R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and may consist of straight or branched, saturated or unsaturated hydrocarbons.

The term "unsaturated cyclic hydrocarbon" is used to describe a non-aromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Alkylheteroaryl" defines a subset of "heteroaryl" substituted with an alkyl group, as defined herein.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

The term "heterocyclic" is used herein to describe a saturated or unsaturated non-aromatic group having a single ring or multiple condensed rings from about 1 to about 12 carbon atoms and from about 1 to about 4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "alkylheterocyclyl" defines a subset of "heterocyclic" substituted with an alkyl group, as defined herein.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

Introduction

This invention describes the generation of evolved monooxygenases with enhanced performance for use in the production of chemicals of industrial interest using any of a variety of shuffling techniques, including, for example, gene, family and whole genome shuffling as described herein. In this invention, shuffling is used to enhance properties of monooxygenases, such as forward rate kinetics, substrate specificity, regioselectivity, chemoselectivity, stereoselectivity and affinity and also to decrease susceptibility of monooxygenases to reversible inhibitors and inactivation by solvents, starting materials and reaction products and intermediates generated during the catalytic cycle.

While much of the discussion below deals explicitly with P450 monooxygenases, this is for clarity of illustration. The discussion is representative of the chemistries and improvements which can be made to other useful monooxygenases, such as the structurally and functionally similar peroxidases and chlorperoxidases, as well as to the structurally unrelated iron-sulfur methane monooxygenases and other enzymes noted herein using the gene and family shuffling methodologies described.

In a first aspect, the present invention provides a method for obtaining a nucleic acid that encodes an improved polypeptide possessing monooxygenase activity. The improved polypeptide has at least one property improved over a naturally occurring monooxygenase polypeptide. The method includes: (a) creating a library of recombinant polynucleotides encoding a recombinant monooxygenase polypeptide; and (b) screening the library to identify a recombinant polynucleotide that encodes an improved recombinant monooxygenase polypeptide that has at least one property improved over the naturally occurring polypeptide. Also provided are nucleic acids produced by this method that encode a monooxygenase polypeptide having at least one property improved over a naturally occurring monooxygenase polypeptide.

In a preferred embodiment, the nucleic acid libraries of the invention are constructed by a method that includes shuffling a plurality of parental polynucleotides to produce one or more recombinant monooxygenase polynucleotide encoding the improved property. In another preferred embodiment, the polynucleotides are homologous. A detailed description of shuffling techniques is provided in Part A, hereinbelow.

In another embodiment, at least one of the parental polynucleotides is selected from polynucleotides that encode at least one monooxygenase activity and those that do not encode at least one monooxygenase activity. Typically, the parental monooxygenase polynucleotide encodes a complete polypeptide or a polypeptide fragment selected from an arene monooxygenase or fragments thereof.

In a preferred embodiment, the monooxygenase activity is a member selected from alkane oxidation (e.g., hydroxylation, formation of ketones, aldehydes, etc.), alkene epoxidation, aromatic hydroxylation, N-dealkylation (e.g., of alkylamines), S-dealkylation (e.g., of reduced thio-organics), O-dealkylation (e.g., of alkyl ethers), oxidation of aryloxy phenols, conversion of aldehydes to acids, alcohols to aldehydes or ketones, dehydrogenation, decarbonylation, oxidative dehalogenation of haloaromatics and halohydrocarbons, Baeyer-Villiger monooxygenation, modification of cyclosporins, hydroxylation of mevastatin, hydroxylation of erythromycin, hydroxylations of fatty acids, hydroxylation/epoxidation of terpenes, N-hydroxylation, sulfoxide formation, or oxygenation of sulfonylureas. Other oxidative transformations will be apparent to those of skill in the art.

The invention provides significant advantages over previously used methods for optimization of monooxygenase genes. For example, DNA shuffling can result in optimization of a desirable property even in the absence of a detailed understanding of the mechanism by which the particular property is mediated. In addition, entirely new properties can be obtained upon shuffling of DNAs, i.e., shuffled DNAs can encode polypeptides or RNAs with properties entirely absent in the parental DNAs which are shuffled.

The properties or characteristics that can be acquired or improved vary widely, and depend on the choice of substrate. For example, for monooxygenase genes, properties that one can improve include, but are not limited to, increased range of monooxygenases activity encoded by a particular gene, increased potency against a monooxygenase target, increased regioselectivity of action against a monooxygenase target, increased chemoselectivity of action against a monooxygenase target, increased stereoselectivity of action against a monooxygenase target, increased expression level of the monooxygenase gene, increased tolerance of the protein encoded by the monooxygenase gene to protease degradation (or other natural protein or RNA degradative processes), increased monooxygenase activity ranges for conditions such as heat, cold, low or high pH, reduced toxicity to the host cell, and increased resistance of the polypeptide and/or the organism expressing the polypeptide to organic solvents, and reaction feedstocks, intermediates and products.

The targets for modification vary in different applications, as does the property sought to be acquired or improved. Examples of candidate targets for acquisition of a property or improvement in a property include genes that encode proteins which have enzymatic or other activities useful in monooxygenase reactions.

The methods typically use at least two variant forms of a starting target. The variant forms of candidate substrates can show substantial sequence or secondary structural similarity with each other, but they should also differ in at least one and preferably at least two positions.

The initial diversity between forms can be the result of natural variation, e.g., the different variant forms (homologs) are obtained from different individuals or strains of an organism, or constitute related sequences from the same organism (e.g., allelic variations), or constitute homologs from different organisms (interspecific variants). Alternatively, initial diversity can be induced, e.g., the variant forms can be generated by error-prone transcription, such as an error-prone PCR or use of a polymerase which lacks proof-reading activity (see, Liao, Gene 88:107–111 (1990)), of the first variant form, or, by replication of the first form in a mutator strain (mutator host cells are discussed in further detail below, and are generally well known). Alternatively, initial diversity can be generated by the creation of chimeric nucleic acids. The initial diversity between substrates is greatly augmented in subsequent steps of recombination for library generation.

A mutator strain can include any mutants in any organism impaired in the functions of mismatch repair. These include mutant gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small molecule or an expressed antisense RNA, or other techniques. Impairment can be of the genes noted, or of homologous genes in any organism.

Therefore, in carrying out the practice of the present invention, at least two variant forms of a nucleic acid which can confer monooxygenase activity are recombined to produce a library of recombinant monooxygenase genes. The library is then screened to identify at least one recombinant monooxygenase gene that is optimized for the particular property or properties of interest.

The parental polynucleotides can be shuffled in substantially any cell type, including prokaryotes, eukaryotes, yeast, bacteria and fungi. In a preferred embodiment, the one or more recombinant monooxygenase nucleic acid is present in one or more bacterial, yeast, or fungal cells and the method includes: pooling multiple separate monooxygenase nucleic acids; screening the resulting pooled monooxygenase nucleic acids to identify a distinct or improved recombinant monooxygenase nucleic acids that exhibit distinct or improved monooxygenase activity compared to a non-recombinant monooxygenase activity nucleic acid; and cloning the distinct or improved recombinant nucleic acid.

Often, improvements are achieved after one round of recombination and selection. However, recursive sequence recombination can be employed to achieve still further improvements in a desired property, or to bring about new (or "distinct") properties. Recursive sequence recombination entails successive cycles of recombination to generate molecular diversity. That is, one creates a family of nucleic acid molecules showing some sequence identity to each other but differing in the presence of mutations. In any given cycle, recombination can occur in vivo or in vitro, intracellularly or extracellularly. Furthermore, diversity resulting from recombination can be augmented in any cycle by applying prior methods of mutagenesis (e.g., error-prone PCR or cassette mutagenesis) to either the substrates or products for recombination.

A recombination cycle is usually followed by at least one cycle of screening or selection for molecules having a desired property or characteristic. If a recombination cycle is performed in vitro, the products of recombination, i.e., recombinant segments, are sometimes introduced into cells before the screening step. Recombinant segments can also be linked to an appropriate vector or other regulatory sequences before screening. Alternatively, products of recombination generated in vitro are sometimes packaged in viruses (e.g., bacteriophage) before screening. If recombination is performed in vivo, recombination products can sometimes be screened in the cells in which recombination occurred. In other applications, recombinant segments are extracted from the cells, and optionally packaged as viruses, before screening.

The nature of screening or selection depends on what property or characteristic is to be acquired or the property or characteristic for which improvement is sought, and many examples are discussed below. It is not usually necessary to understand the molecular basis by which particular products of recombination (recombinant segments) have acquired new or improved properties or characteristics relative to the starting substrates. For example, a monooxygenase gene can have many component sequences each having a different intended role (e.g., coding sequence, regulatory sequences, targeting sequences, stability-conferring sequences, subunit sequences and sequences affecting integration). Each of these component sequences can be varied and recombined simultaneously. Screening/selection can then be performed, for example, for recombinant segments that have increased ability to confer monooxygenase activity upon a cell without the need to attribute such improvement to any of the individual component sequences of the vector.

Depending on the particular screening protocol used for a desired property, initial round(s) of screening can sometimes be performed using bacterial cells due to high transfection efficiencies and ease of culture. However, for eukaryotic monooxygenases such as eukaryotic arene monooxygenases, bacterial expression is often not practical, and yeast, fungal or other eukaryotic systems are used for library expression and screening. Similarly other types of screening which are not amenable to screening in bacterial or simple eukaryotic library cells, are performed in cells selected for use in an environment close to that of their intended use. Final rounds of screening can be performed in the precise cell type of intended use.

If further improvement in a property is desired, at least one and usually a collection of recombinant segments surviving a first round of screening/selection are subject to a further round of recombination. These recombinant segments can be recombined with each other or with exogenous segments representing the original substrates or further variants thereof. Again, recombination can proceed in vitro or in vivo. If the previous screening step identifies desired recombinant segments as components of cells, the components can be subjected to further recombination in vivo, or can be subjected to further recombination in vitro, or can be isolated before performing a round of in vitro recombination. Conversely, if the previous screening step identifies desired recombinant segments in naked form or as components of viruses, these segments can be introduced into cells to perform a round of in vivo recombination. The second round of recombination, irrespective how performed, generates further recombinant segments which encompass additional diversity than is present in recombinant segments resulting from previous rounds.

The second round of recombination can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired. Additional rounds of recombination and screening can then be performed until the recombinant segments have sufficiently evolved to acquire the desired new or improved property or function.

In a preferred embodiment, the invention provides a recursive method for making a nucleic acid encoding a specific monooxygenase activity. In this method, the parental nucleic acids are shuffled in a plurality of cells and the method optionally further includes one or more of: (a) recombining DNA from the plurality of cells that display monooxygenase activity with a library of DNA fragments, at least one of which undergoes recombination with a segment in a cellular DNA present in the cells to produce recombined cells, or recombining DNA between the plurality of cells that display monooxygenase activity to produce cells with modified monooxygenase activity; (b) recombining and screening the recombined or modified cells to produce further recombined cells that have evolved additionally modified monooxygenase activity; and, (c) repeating (a) or (b) until the further recombined cells have acquired a desired monooxygenase activity.

In another preferred embodiment, the invention provides a method for making a nucleic acid encoding a specific monooxygenase activity. This method includes: (a) recombining at least one distinct or improved recombinant nucleic acid with a further monooxygenase activity nucleic acid, which further nucleic acid is the same or different from one or more of the plurality of parental nucleic acids to produce a library of recombinant monooxygenase nucleic acids; (b) screening the library to identify at least one further distinct or improved recombinant monooxygenase nucleic acid that exhibits a further improvement or distinct property compared to the plurality of parental nucleic acids; and, optionally; (c) repeating (a) and (b) until the resulting further distinct or improved recombinant nucleic acid shows an additionally distinct or improved monooxygenase property.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. General texts which describe molecular biological techniques useful herein, including mutagenesis, include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1–3, Cold Spring Harbor Laboratory, Cold Spring Harbor, New York, 1989 ("Sambrook") and CURRENT PROTOCOLS IN MOLECULAR BIOLOGY, F. M. Ausubel et al., eds., Current Protocols, a joint venture between Greene Publishing Associates, Inc. and John Wiley & Sons, Inc., (supplemented through 1998) ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) *C&EN* 36–47; *The Journal Of NIH Research* 3:81–94 (1991); (Kwoh et al., *Proc. Natl. Acad. Sci. USA* 86:1173 (1989); Guatelli et al., *Proc. Natl. Acad. Sci. USA* 87:1874 (1990); Lomell et al., *J. Clin. Chem* 35:1826 (1989); Landegren et al., *Science* 241:1077–1080 (1988); Van Brunt, *Biotechnology* 8:291–294 (1990); Wu and Wallace, *Gene* 4:560 (1989); Barringer et al., *Gene* 89:117 (1990); and Sooknanan and Malek, *Biotechnology* 13:563–564 (1995). Improved methods of cloning in vitro amplified nucleic acids are described in Wallace et al., U.S. Pat. No. 5,426,039. Improved methods of amplifying large nucleic acids by PCR are summarized in Cheng et al., *Nature* 369:684–685 (1994) and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

In another aspect, the present invention provides a method of increasing monooxygenase activity in a cell. The method includes performing whole genome shuffling of a plurality of genomic nucleic acids in the cell and selecting for one or more monooxygenase activity. In this aspect of the invention, the genomic nucleic acids can be from substantially any source. In a preferred embodiment of this aspect of the invention, the genomic nucleic acids are from a species or strain different from the cell. In a further preferred embodiment, the cell is of prokaryotic or eukaryotic origin.

Substantially any monooxygenase property can be selected for using the methods of the invention. A preferred property is the activity of the polypeptide towards a particular class of substrates. In preferred embodiment, the monooxygenase property is its ability to effect alkene epoxidation, alkane oxidation (e.g., hydroxylation, conversion to carboxylic acid, etc.), aromatic hydroxylation, N-dealkylation of alkylamines, S-dealkylation of reduced thio-organics, O-Dealkylation of alkyl ethers, oxidation of aryloxy phenols, conversion of aldehydes to acids, dehydrogenation, decarbonylation, oxidative dehalogenation of haloaromatics and halohydrocarbons, Baeyer-Villiger monoxygenation, modification of cyclosporins, hydroxylation of mevastatin, hydroxylation of fatty acids, hydroxylation/epoxidation of terpenes, conversion of cholesterol to pregnenolone, or oxygenation of sulfonylureas.

In a third aspect, the invention provides a DNA shuffling mixture comprising: at least three homologous DNAs, each of which is derived from a nucleic acid encoding a polypeptide or polypeptide fragment which encodes monooxygenase activity. In a preferred embodiment of this aspect of the invention, the at least three homologous DNAs are present in cell culture or in vitro.

Oligonucleotides for use as probes, e.g., in in vitro amplification methods, for use as gene probes, or as shuffling targets (e.g., synthetic genes or gene segments) are typically synthesized chemically according to the solid phase phosphoramidite triester method described by Beaucage and Caruthers, *Tetrahedron Letts.* 22(20): 1859–1862, (1981) e.g., using an automated synthesizer, as described in Needham-VanDevanter et al., *Nucleic Acids Res.,* 12:6159–6168 (1984). Oligonucleotides can also be custom made and ordered from a variety of commercial sources known to persons of skill.

A. Formats for Sequence Recombination

The methods of the invention entail performing recombination ("shuffling") and screening or selection to "evolve" individual genes, whole plasmids or viruses, multigene clusters, or even whole genomes (Stemmer, *Bio/Technology* 13:549–553 (1995)). Reiterative cycles of recombination and screening/selection can be performed to further evolve the nucleic acids of interest. Such techniques do not require the extensive analysis and computation required by conventional methods for polypeptide engineering. Shuffling allows the recombination of large numbers of mutations in a minimum number of selection cycles, in contrast to natural pair-wise recombination events (e.g., as occur during sexual replication). Thus, the sequence recombination techniques described herein provide particular advantages in that they provide recombination between mutations in any or all of these, thereby providing a very fast way of exploring the manner in which different combinations of mutations can affect a desired result. In some instances, however, structural and/or functional information is available which, although not required for sequence recombination, provides opportunities for modification of the technique.

Sequence recombination can be achieved in many different formats and permutations of formats. Exemplary formats and examples for sequence recombination, referred to, e.g., as "DNA shuffling," "fast forced evolution," or "molecular breeding," have been described in the following patents and patent applications: U.S. patent application Ser. No. 08/198,431, filed Feb. 17, 1994, U.S. Pat. No. 5,605,793; PCT Application WO 95/22625 (Ser. No. PCT/US95/02126), filed Feb. 17, 1995; U.S. Ser. No. 08/425,684, filed Apr. 18, 1995; Ser. No. 08/537,874, filed Oct. 30, 1995, Ser. No. 08/564,955, filed Nov. 30, 1995, Ser. No. 08/621,859, filed Mar. 25, 1996, U.S. Ser. No. 08/621,430, filed Mar. 25, 1996; Ser. No. PCT/US96/05480, filed Apr. 18, 1996, Ser. No. 08/650,400, filed May 20, 1996, Ser. No. PCT/US97/17300, filed Sep. 26, 1997, Ser. No. PCT/US97/24239, filed Dec. 17, 1997; Ser. No. 98/354,922, filed Jul. 15, 1999, Ser. No. PCT/US98/05956, filed Mar. 25, 1998; PCT Application WO 97/20078 (Ser. No. PCT/US96/05480), filed Apr. 18, 1996; PCT Application WO 97/35966, filed Mar. 20, 1997; U.S. Ser. No. 08/675,502, filed Jul. 3, 1996; U.S. Ser. No. 08/721,824, filed Sep. 27, 1996; PCT Application WO 98/13487, filed Sep. 26, 1997; "Evolution of Whole Cells and Organisms by Recursive Sequence Recombination" Attorney Docket No. 018097-020720US filed Jul. 15, 1998 by del Cardayre et al. (U.S. Ser. No. 09/161,188); Stemmer, *Science* 270:1510 (1995); Stemmer et al., *Gene* 164:49–53 (1995); Stemmer, *Bio/Technology* 13:549–553 (1995); Stemmer, *Proc. Natl. Acad. Sci. U.S.A.* 91:10747–10751 (1994); Stemmer, *Nature* 370:389–391 (1994); Crameri et al., *Nature Medicine* 2(1):1–3 (1996); Crameri et al., *Nature Biotechnology* 14:315–319 (1996), and PCT Application WO 98/42832 (Ser. No. PCT/US98/05956), filed Mar. 25, 1998, each of which is incorporated by reference in its entirety for all purposes.

Gene shuffling and family shuffling provide two of the most powerful methods available for improving and "migrating" (gradually changing the type of reaction, substrate or activity of a selected enzyme) the functions of biocatalysts. In family shuffling, homologous sequences, e.g., from different species or chromosomal positions, are recombined. In gene shuffling, a single sequence is mutated or otherwise altered and then recombined. These formats share some common principles.

The breeding procedure starts with at least two substrates that generally show substantial sequence identity to each other (i.e., at least about 30%, 50%, 70%, 80% or 90% sequence identity), but differ from each other at certain positions. The difference can be any type of mutation, for example, substitutions, insertions and deletions. Often, different segments differ from each other in about 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second at a single position, and the second can differ from the third at a different single position. The starting DNA segments can be natural variants of each other, for example, allelic or species variants. The segments can also be from nonallelic genes showing some degree of structural and usually functional relatedness (e.g., different genes within a superfamily, such as the arene monooxygenase super family). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The starting DNA segments are recombined by any of the sequence recombination formats provided herein to generate a diverse library of recombinant DNA segments. Such a library can vary widely in size from having fewer than 10 to more than $10^5$, $10^9$, $10^{12}$ or more members. In some embodiments, the starting segments and the recombinant libraries generated will include full-length coding sequences and any essential regulatory sequences, such as a promoter and polyadenylation sequence, required for expression. In other embodiments, the recombinant DNA segments in the library can be inserted into a common vector providing sequences necessary for expression before performing screening/selection.

1. Use of Restriction Enzyme Sites to Recombine Mutations

In some situations it is advantageous to use restriction enzyme sites in nucleic acids to direct the recombination of mutations in a nucleic acid sequence of interest. These techniques are particularly preferred in the evolution of fragments that cannot readily be shuffled by existing methods due to the presence of repeated DNA or other problematic primary sequence motifs. These situations also include recombination formats in which it is preferred to retain certain sequences unmutated. The use of restriction enzyme sites is also preferred for shuffling large fragments (typically greater than 10 kb), such as gene clusters that cannot be readily shuffled and "PCR-amplified" because of their size. Although fragments up to 50 kb have been reported to be amplified by PCR (Barnes, *Proc. Natl. Acad. Sci. U.S.A.* 91:2216–2220 (1994)), it can be problematic for fragments over 10 kb, and thus alternative methods for shuffling in the range of 10–50 kb and beyond are preferred. Preferably, the restriction endonucleases used are of the Class II type (Sambrook, Ausubel and Berger, supra) and of these, preferably those which generate nonpalindromic sticky end overhangs such as Alwn I, Sfi I or BstX1. These enzymes generate nonpalindromic ends that allow for efficient ordered reassembly with DNA ligase. Typically, restriction enzyme (or endonuclease) sites are identified by conventional restriction enzyme mapping techniques (Sambrook, Ausubel, and Berger, supra.), by analysis of sequence information for that gene, or by introduction of desired restriction sites into a nucleic acid sequence by synthesis (i.e. by incorporation of silent mutations).

The DNA substrate molecules to be digested can either be from in vivo replicated DNA, such as a plasmid preparation, or from PCR amplified nucleic acid fragments harboring the restriction enzyme recognition sites of interest, preferably near the ends of the fragment. Typically, at least two variants of a gene of interest, each having one or more mutations, are digested with at least one restriction enzyme determined to cut within the nucleic acid sequence of interest. The restriction fragments are then joined with DNA ligase to generate full length genes having shuffled regions. The number of regions shuffled will depend on the number of cuts within the nucleic acid sequence of interest. The shuffled molecules can be introduced into cells as described above and screened or selected for a desired property as described herein. Nucleic acid can then be isolated from pools (libraries), or clones having desired properties and subjected to the same procedure until a desired degree of improvement is obtained.

In some embodiments, at least one DNA substrate molecule or fragment thereof is isolated and subjected to mutagenesis. In some embodiments, the pool or library of religated restriction fragments are subjected to mutagenesis before the digestion-ligation process is repeated. "Mutagenesis" as used herein includes such techniques known in the art as PCR mutagenesis, oligonucleotide-directed mutagenesis, site-directed mutagenesis, etc., and recursive sequence recombination by any of the techniques described herein.

2. Reassembly PCR

A further technique for recombining mutations in a nucleic acid sequence utilizes "reassembly PCR." This method can be used to assemble multiple segments that have been separately evolved into a full length nucleic acid template such as a gene. This technique is performed when a pool of advantageous mutants is known from previous work or has been identified by screening mutants that may have been created by any mutagenesis technique known in the art, such as PCR mutagenesis, cassette mutagenesis, doped oligo mutagenesis, chemical mutagenesis, or propagation of the DNA template in vivo in mutator strains. Boundaries defining segments of a nucleic acid sequence of interest preferably lie in intergenic regions, introns, or areas of a gene not likely to have mutations of interest. Preferably, oligonucleotide primers (oligos) are synthesized for PCR amplification of segments of the nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols such as those discussed herein to assemble randomly fragmented genes. In brief, in an assembly protocol the PCR products are first purified away from the primers, by, for example, gel electrophoresis or size exclusion chromatography. Purified products are mixed together and subjected to about 1–10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments, the resulting reassembled genes are subjected to mutagenesis before the process is repeated.

In a further embodiment, the PCR primers for amplification of segments of the nucleic acid sequence of interest are used to introduce variation into the gene of interest as follows. Mutations at sites of interest in a nucleic acid sequence are identified by screening or selection, by sequencing homologues of the nucleic acid sequence, and so on. Oligonucleotide PCR primers are then synthesized which encode wild type or mutant information at sites of interest. These primers are then used in PCR mutagenesis to generate libraries of full length genes encoding permutations of wild type and mutant information at the designated positions. This technique is typically advantageous in cases where the screening or selection process is expensive, cumbersome, or impractical relative to the cost of sequencing the genes of mutants of interest and synthesizing mutagenic oligonucleotides.

3. Site Directed Mutagenesis (SDM) with Oligonucleotides Encoding Homologue Mutations Followed by Shuffling In some embodiments of the invention, sequence information from one or more substrate sequences is added to a given "parental" sequence of interest, with subsequent recombination between rounds of screening or selection. Typically, this is done with site-directed mutagenesis performed by techniques well known in the art (e.g., Berger, Ausubel and Sambrook, supra.) with one substrate as template and oligonucleotides encoding single or multiple mutations from other substrate sequences, e.g. homologous genes. After screening or selection for an improved phenotype of interest, the selected recombinant(s) can be further evolved using RSR techniques described herein. After screening or selection, site-directed mutagenesis can be done again with another collection of oligonucleotides encoding homologue mutations, and the above process repeated until the desired properties are obtained.

When the difference between two homologues is one or more single point mutations in a codon, degenerate oligonucleotides can be used that encode the sequences in both homologues. One oligonucleotide can include many such degenerate codons and still allow one to exhaustively search all permutations over that block of sequence.

When the homologue sequence space is very large, it can be advantageous to restrict the search to certain variants. Thus, for example, computer modeling tools (Lathrop et al., *J. Mol. Biol.* 255:641–665 (1996)) can be used to model each homologue mutation onto the target protein and discard any mutations that are predicted to grossly disrupt structure and function.

4. In vitro DNA Shuffling Formats

In one embodiment for shuffling DNA sequences in vitro, the initial substrates for recombination are a pool of related sequences, e.g., different variant forms, as homologs from different individuals, strains, or species of an organism, or related sequences from the same organism, as allelic variations. The sequences can be DNA or RNA and can be of various lengths depending on the size of the gene or DNA fragment to be recombined or reassembled. Preferably the sequences are from 50 base pairs (bp) to 50 kilobases (kb).

The pool of related substrates are converted into overlapping fragments, e.g., from about 5 bp to 5 kb or more. Often, for example, the size of the fragments is from about 10 bp to 1000 bp, and sometimes the size of the DNA fragments is from about 100 bp to 500 bp. The conversion can be effected by a number of different methods, such as DNase I or RNase digestion, random shearing or partial restriction enzyme digestion. For discussions of protocols for the isolation, manipulation, enzymatic digestion, and the like of nucleic acids, see, for example, Sambrook et al. and Ausubel, both supra. The concentration of nucleic acid fragments of a particular length and sequence is often less than 0.1% or 1% by weight of the total nucleic acid. The number of different specific nucleic acid fragments in the mixture is usually at least about 100, 500 or 1000.

The mixed population of nucleic acid fragments are converted to at least partially single-stranded form using a variety of techniques, including, for example, heating, chemical denaturation, use of DNA binding proteins, and the like. Conversion can be effected by heating to about 80° C. to 100° C., more preferably from 90° C. to 96° C., to form single-stranded nucleic acid fragments and then reannealing. Conversion can also be effected by treatment with single-stranded DNA binding protein (see Wold, *Annu. Rev. Biochem.* 66:61–92 (1997)) or recA protein (see, e.g., Kiianitsa, *Proc. Natl. Acad. Sci. USA* 94:7837–7840 (1997)). Single-stranded nucleic acid fragments having regions of sequence identity with other single-stranded nucleic acid fragments can then be reannealed by cooling to 20° C. to 75° C., and preferably from 40° C. to 65° C. Renaturation can be accelerated by the addition of polyethylene glycol (PEG), other volume-excluding reagents or salt. The salt concentration is preferably from 0 mM to 200 mM, more preferably the salt concentration is from 10 mM to 100 mM. The salt may be KCl or NaCl. The concentration of PEG is preferably from 0% to 20%, more preferably from 5% to 10%. The fragments that reanneal can be from different substrates. The annealed nucleic acid fragments are incubated in the presence of a nucleic acid polymerase, such as Taq or Klenow, and dNTP's (i.e. dATP, dCTP, dGTP and dTTP). If regions of sequence identity are large, Taq polymerase can be used with an annealing temperature of between 45–65° C. If the areas of identity are small, Klenow polymerase can be used with an annealing temperature of between 20–30° C. The polymerase can be added to the random nucleic acid fragments prior to annealing, simultaneously with annealing or after annealing.

The process of denaturation, renaturation and incubation in the presence of polymerase of overlapping fragments to generate a collection of polynucleotides containing different permutations of fragments is sometimes referred to as shuffling of the nucleic acid in vitro. This cycle is repeated for a desired number of times. Preferably the cycle is repeated from 2 to 100 times, more preferably the sequence is repeated from 10 to 40 times. The resulting nucleic acids are a family of double-stranded polynucleotides of from about 50 bp to about 100 kb, preferably from 500 bp to 50 kb. The population represents variants of the starting substrates showing substantial sequence identity thereto but also diverging at several positions. The population has many more members than the starting substrates. The population of fragments resulting from shuffling is used to transform host cells, optionally after cloning into a vector.

In one embodiment utilizing in vitro shuffling, subsequences of recombination substrates can be generated by amplifying the full-length sequences under conditions which produce a substantial fraction, typically at least 20 percent or more, of incompletely extended amplification products. Another embodiment uses random primers to prime the entire template DNA to generate less than full length amplification products. The amplification products, including the incompletely extended amplification products are denatured and subjected to at least one additional cycle of reannealing and amplification. This variation, in which at least one cycle of reannealing and amplification provides a substantial fraction of incompletely extended products, is termed "stuttering." In the subsequent amplification round, the partially extended (less than full length) products reanneal to and prime extension on different sequence-related template species. In another embodiment, the conversion of substrates to fragments can be effected by partial PCR amplification of substrates.

In another embodiment, a mixture of fragments is spiked with one or more oligonucleotides. The oligonucleotides can be designed to include precharacterized mutations of a wildtype sequence, or sites of natural variations between individuals or species. The oligonucleotides also include sufficient sequence or structural homology flanking such mutations or variations to allow annealing with the wildtype fragments. Annealing temperatures can be adjusted depending on the length of homology.

In a further embodiment, recombination occurs in at least one cycle by template switching, such as when a DNA fragment derived from one template primes on the homologous position of a related but different template. Template switching can be induced by addition of recA (see, Kiianitsa supra (1997)), rad51 (see, Namsaraev, *Mol. Cell. Biol.*

17:5359–5368 (1997)), rad55 (see, Clever, *EMBO J.* 16:2535–2544 (1997)), rad57 (see, Sung, *Genes Dev.* 11:1111–1121 (1997)) or other polymerases (e.g., viral polymerases, reverse transcriptase) to the amplification mixture. Template switching can also be increased by increasing the DNA template concentration.

Another embodiment utilizes at least one cycle of amplification, which can be conducted using a collection of overlapping single-stranded DNA fragments of related sequence, and different lengths. Fragments can be prepared using a single stranded DNA phage, such as M13 (see, Wang, *Biochemistry* 36:9486–9492 (1997)). Each fragment can hybridize to and prime polynucleotide chain extension of a second fragment from the collection, thus forming sequence-recombined polynucleotides. In a further variation, ssDNA fragments of variable length can be generated from a single primer by Pfu, Taq, Vent, Deep Vent, UlTma DNA polymerase or other DNA polymerases on a first DNA template (see, Cline, *Nucleic Acids Res.* 24:3546–3551 (1996)). The single stranded DNA fragments are used as primers for a second, Kunkel-type template, consisting of a uracil-containing circular ssDNA. This results in multiple substitutions of the first template into the second. See, Levichkin, *Mol. Biology* 29:572–577 (1995); Jung, *Gene* 121:17–24 (1992).

In some embodiments of the invention, shuffled nucleic acids obtained by use of the recursive recombination methods of the invention, are put into a cell and/or organism for screening. Shuffled monooxygenase genes can be introduced into, for example, bacterial cells, yeast cells, fungal cells vertebrate cells, invertebrate cells or plant cells for initial screening. Bacillus species (such as *B. subtilis* and *E. coli* are two examples of suitable bacterial cells into which one can insert and express shuffled monooxygenase genes which provide for convenient shuttling to other cell types (a variety of vectors for shuttling material between these bacterial cells and eukaryotic cells are available; see, Sambrook, Ausubel and Berger, all supra). The shuffled genes can be introduced into bacterial, fungal or yeast cells either by integration into the chromosomal DNA or as plasmids.

Although bacterial and yeast systems are most preferred in the present invention, in one embodiment, shuffled genes can also be introduced into plant cells for production purposes (it will be appreciated that transgenic plants are, increasingly, an important source of industrial enzymes). Thus, a transgene of interest can be modified using the recursive sequence recombination methods of the invention in vitro and reinserted into the cell for in vivo/in situ selection for the new or improved monooxygenase property, in bacteria, eukaryotic cells, or whole eukaryotic organisms.

5. In vivo DNA Shuffling Formats

In some embodiments of the invention, DNA substrate molecules are introduced into cells, wherein the cellular machinery directs their recombination. For example, a library of mutants is constructed and screened or selected for mutants with improved phenotypes by any of the techniques described herein. The DNA substrate molecules encoding the best candidates are recovered by any of the techniques described herein, then fragmented and used to transfect a plant host and screened or selected for improved function. If further improvement is desired, the DNA substrate molecules are recovered from the host cell, such as by PCR, and the process is repeated until a desired level of improvement is obtained. In some embodiments, the fragments are denatured and reannealed prior to transfection, coated with recombination stimulating proteins such as recA, or co-transfected with a selectable marker such as $Neo^R$ to allow the positive selection for cells receiving recombined versions of the gene of interest. Methods for in vivo shuffling are described in, for example, PCT application WO 98/13487 and WO 97/20078.

The efficiency of in vivo shuffling can be enhanced by increasing the copy number of a gene of interest in the host cells. For example, the majority of bacterial cells in stationary phase cultures grown in rich media contain two, four or eight genomes. In minimal medium the cells contain one or two genomes. The number of genomes per bacterial cell thus depends on the growth rate of the cell as it enters stationary phase. This is because rapidly growing cells contain multiple replication forks, resulting in several genomes in the cells after termination. The number of genomes is strain dependent, although all strains tested have more than one chromosome in stationary phase. The number of genomes in stationary phase cells decreases with time. This appears to be due to fragmentation and degradation of entire chromosomes, similar to apoptosis in mammalian cells. This fragmentation of genomes in cells containing multiple genome copies results in massive recombination and mutagenesis. The presence of multiple genome copies in such cells results in a higher frequency of homologous recombination in these cells, both between copies of a gene in different genomes within the cell, and between a genome within the cell and a transfected fragment. The increased frequency of recombination allows one to evolve a gene evolved more quickly to acquire optimized characteristics.

In nature, the existence of multiple genomic copies in a cell type would usually not be advantageous due to the greater nutritional requirements needed to maintain this copy number. However, artificial conditions can be devised to select for high copy number. Odified cells having recombinant genomes are grown in rich media (in which conditions, multicopy number should not be a disadvantage) and exposed to a mutagen, such as ultraviolet or gamma irradiation or a chemical mutagen, e.g., mitomycin, nitrous acid, photoactivated psoralens, alone or in combination, which induces DNA breaks amenable to repair by recombination. These conditions select for cells having multicopy number due to the greater efficiency with which mutations can be excised. Modified cells surviving exposure to mutagen are enriched for cells with multiple genome copies. If desired, selected cells can be individually analyzed for genome copy number (e.g., by quantitative hybridization with appropriate controls). For example, individual cells can be sorted using a cell sorter for those cells containing more DNA, e.g., using DNA specific fluorescent compounds or sorting for increased size using light dispersion. Some or all of the collection of cells surviving selection are tested for the presence of a gene that is optimized for the desired property.

In one embodiment, phage libraries are made and recombined in mutator strains such as cells with mutant or impaired gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. High multiplicity of infection (MOI) libraries are used to infect the cells to increase recombination frequency.

Additional strategies for making phage libraries and or for recombining DNA from donor and recipient cells are set forth in U.S. Pat. No. 5,521,077. Additional recombination strategies for recombining plasmids in yeast are set forth in WO 97 07205.

6. Whole Genome Shuffling

In one embodiment, the selection methods herein are utilized in a "whole genome shuffling" format. An extensive guide to the many forms of whole genome shuffling is found in the pioneering application to the inventors and their co-workers entitled "Evolution of Whole Cells and Organisms by Recursive Sequence Recombination," Attorney Docket No. 018097-020720US filed Jul, 15, 1998 by del Cardayre et al. (U.S. Ser. No. 09/161,188).

In brief, whole genome shuffling makes no presuppositions at all regarding what nucleic acids may confer a desired property. Instead, entire genomes (e.g., from a genomic library, or isolated from an organism) are shuffled in cells and selection protocols applied to the cells.

The fermentation of microorganisms for the production of natural products is the oldest and most sophisticated application of biocatalysis.

The methods herein allow monooxygenase biocatalysts to be improved at a faster pace than conventional methods. Whole genome shuffling can at least double the rate of strain improvement for microorganisms used in fermentation as compared to traditional methods. This provides for a relative decrease in the cost of fermentation processes. New products can enter the market sooner, producers can increase profits as well as market share, and consumers gain access to more products of higher quality and at lower prices. Further, increased efficiency of production processes translates to less waste production and more frugal use of resources. Whole genome shuffling provides a means of accumulating multiple useful mutation per cycle and thus eliminate the inherent limitation of current strain improvement programs (SIPs).

DNA shuffling provides recursive mutagenesis, recombination, and selection of DNA sequences. A key difference between DNA shuffling-mediated recombination and natural sexual recombination is that DNA shuffling effects both the pairwise (two parents) and the poolwise (multiple parents) recombination of parent molecules. Natural recombination is more conservative and is limited to pairwise recombination. In nature, pairwise recombination provides stability within a population by preventing large leaps in sequences or genomic structure that can result from poolwise recombination. However, for the purposes of directed evolution, poolwise recombination is appealing since the beneficial mutations of multiple parents can be combined during a single cross to produce a superior offspring. Poolwise recombination is analogous to the cross-breeding of inbred strains in classic strain improvement, except that the crosses occur between many strains at once. In essence, poolwise recombination is a sequence of events that effects the recombination of a population of nucleic acid sequences that results in the generation of new nucleic acids that contains genetic information from more than two of the original nucleic acids.

There are a few general methods for effecting efficient recombination in prokaryotes. Bacteria have no known sexual cycle per se, but there are natural mechanisms by which the genomes of these organisms undergo recombination. These mechanisms include natural competence, phage-mediated transduction, and cell-cell conjugation. Bacteria that are naturally competent are capable of efficiently taking up naked DNA from the environment. If homologous, this DNA undergoes recombination with the genome of the cell, resulting in genetic exchange. *Bacillus subtilis*, the primary production organism of the enzyme industry, is known for the efficiency with which it carries out this process.

In generalized transduction, a bacteriophage mediates genetic exchange. A transducing phage will often package headfulls of the host genome. These phage can infect a new host and deliver a fragment of the former host genome which is frequently integrated via homologous recombination. Cells can also transfer DNA between themselves by conjugation. Cells containing the appropriate mating factors transfer episomes as well as entire chromosomes to an appropriate acceptor cell where it can recombine with the acceptor genome. Conjugation resembles sexual recombination for microbes and can be intraspecific, interspecific, and intergeneric. For example, an efficient means of transforming Streptomyces sp., a genera responsible for producing many commercial antibiotics, is by the conjugal transfer of plasmids from *Echerichia coli*.

For many industrial microorganisms, knowledge of competence, transducing phage, or fertility factors is lacking. Protoplast fusion has been developed as a versatile and general alternative to these natural methods of recombination. Protoplasts are prepared by removing the cell wall by treating cells with lytic enzymes in the presence of osmotic stabilizers. In the presence of a fusogenic agent, such as polyethylene glycol (PEG), protoplasts are induced to fuse and form transient hybrids or "fusants." During this hybrid state, genetic recombination occurs at high frequency allowing the genomes to reassort. The final step is the successful segregation and regeneration of viable cells from the fused protoplasts. Protoplast fusion can be intraspecific, interspecific, and intergeneric and has been applied to both prokaryotes and eukaryotes. In addition, it is possible to fuse more than two cells, thus providing a mechanism for effecting poolwise recombination. While no fertility factors, transducing phages or competency development is needed for protoplast fusion, a method for the formation, fusing, and regeneration of protoplasts is typically optimized for each organism.

Modifications can be made to the method and materials as hereinbefore described without departing from the spirit or scope of the invention as claimed, and the invention can be put to a number of different uses, including:

The use of an integrated system to test monooxygenase in shuffled DNAs, including in an iterative process.

7. Family Shuffling P450s

For identification of homologous genes used in family shuffling strategies, representative alignments of P450 enzymes can be found in the Appendices of the volume CYTOCHROME P450: STRUCTURE, MECHANISM, AND BIOCHEMISTRY, $2^{nd}$ Addition (ed. by Paul R. Ortiz de Montellano) Plenum Press, New York, 1995) ("Ortiz de Montellano"). An up-to-date list of P450s can be found electronically on the World Wide Web (http://drnelson.utmem.edu/homepage.html).

To illustrate the family shuffling approach to improving P450 enzymes, one or more of the more than 1000 members of this superfamily is selected, aligned with similar homologous sequences, and shuffled against these homologous sequences.

For example, the gene for the bovine $P450_{scc}$ enzyme, CYP11A1, belongs to a family of closely related P450 genes. DNA family shuffling (Crameri et al., *Nature* 391:288) can be used to create hybrid variants from these genes, variants of which can be screened for enhanced conversion of cholesterol to pregnenolone.

The screening is done most easily in yeast, but a bacterial system could also be constructed by co-expressing the accessory electron transport proteins adrenodoxin and adrenodoxin reductase. DNA from clones with improved activity can be shuffled together in subsequent rounds of DNA shuffling and screened for further improvement.

Subsequent steps in the biosynthesis of steroids such as cortisone and estradiol are also catalyzed by cytochrome P450 enzymes (see, Ortiz de Montellano, chapter 12.) For example, conversion of pregnenolone to cortisol involves four enzymatic steps, three of which are catalyzed by cytochrome P450 enzymes. Each of these enzymes belongs to P450 gene families, which also are amenable to DNA family shuffling.

One model P450 system has been developed by Pompon and co-workers (e.g., Duport et al., *Nature Biotechnol.* 16:186; Pompon et al., *Methods Enzymol.* 272:51). In particular, they have developed a yeast strain that produces pregnenolone from galactose, and an additional strain that further converts pregnenolone to progesterone. One of the enzymes expressed in these strains is the bovine $P450_{scc}$. Optimization of this strain, or of related processes useful for steroid production can be assisted by DNA shuffling of $P450_{scc}$. Numerous other microbial expression systems for P450-type enzymes are known in the literature.

8. Codon Modification Shuffling

Procedures for codon modification shuffling are described in detail in SHUFFLING OF CODON ALTERED GENES, Phillip A. Patten and Willem P. C. Stemmer, filed Sep. 29, 1998, U.S. Ser. No. 60/102362 and in SHUFFLING OF CODON ALTERED GENES, Phillip A. Patten and Willem P. C. Stemmer, filed Jan. 29, 1999, U.S. Ser. No. 60/117729. In brief, by synthesizing nucleic acids in which the codons encoding polypeptides are altered, it is possible to access a completely different mutational cloud upon subsequent mutation of the nucleic acid. This increases the sequence diversity of the starting nucleic acids for shuffling protocols, which alters the rate and results of forced evolution procedures. Codon modification procedures can be used to modify any nucleic acid described herein, e.g., prior to performing DNA shuffling, or codon modification approaches can be used in conjunction with oligonucleotide shuffling procedures as described supra.

In these methods, a first nucleic acid sequence encoding a first polypeptide sequence is selected. A plurality of codon altered nucleic acid sequences, each of which encode the first polypeptide, or a modified or related polypeptide, is then selected (e.g., a library of codon altered nucleic acids can be selected in a biological assay which recognizes library components or activities), and the plurality of codon-altered nucleic acid sequences is recombined to produce a target codon altered nucleic acid encoding a second protein. The target codon altered nucleic acid is then screened for a detectable functional or structural property, optionally including comparison to the properties of the first polypeptide and/or related polypeptides. The goal of such screening is to identify a polypeptide that has a structural or functional property equivalent or superior to the first polypeptide or related polypeptide. A nucleic acid encoding such a polypeptide can be used in essentially any procedure desired, including introducing the target codon altered nucleic acid into a cell, vector, virus, attenuated virus (e.g., as a component of a vaccine or immunogenic composition), transgenic organism, or the like.

9. Oligonucleotide and in silico shuffling formats

In addition to the formats for shuffling noted above, at least two additional related formats are useful in the practice of the present invention. The first, referred to as "in silico" shuffling utilizes computer algorithms to perform "virtual" shuffling using genetic operators in a computer. As applied to the present invention, gene sequence strings are recombined in a computer system and desirable products are made, e.g., by reassembly PCR of synthetic oligonucleotides. In silico shuffling is described in detail in Selifonov and Stemmer in "METHODS FOR MAKING CHARACTER STRINGS, POLYNUCLEOTIDES & POLYPEPTIDES HAVING DESIRED CHARACTERISTICS" filed Feb. 5, 1999, U.S. Ser. No. 60/118854. In brief, genetic operators (algorithms which represent given genetic events such as point mutations, recombination of two strands of homologous nucleic acids, etc.) are used to model recombinational or mutational events which can occur in one or more nucleic acid, e.g., by aligning nucleic acid sequence strings (using standard alignment software, or by manual inspection and alignment) and predicting recombinational outcomes. The predicted recombinational outcomes are used to produce corresponding molecules, e.g., by oligonucleotide synthesis and reassembly PCR.

The second useful format is referred to as "oligonucleotide mediated shuffling" in which oligonucleotides corresponding to a family of related homologous nucleic acids (e.g., as applied to the present invention, interspecific or allelic variants of a dioxygenase nucleic acid) which are recombined to produce selectable nucleic acids. This format is described in detail in Crameri et al. "OLIGONUCLEOTIDE MEDIATED NUCLEIC ACID RECOMBINATION" filed Feb. 5, 1999, U.S. Ser. No. 60/118,813 and Crameri et al. "OLIGONUCLEOTIDE MEDIATED NUCLEIC ACID RECOMBINATION" filed Jun. 24, 1999, U.S. Ser. No. 60/141,049. The technique can be used to recombine homologous or even non-homologous nucleic acid sequences.

One advantage of the oligonucleotide-mediated recombination is the ability to recombine homologous nucleic acids with low sequence similarity, or even non-homologous nucleic acids. In these low-homology oligonucleotide shuffling methods, one or more set of fragmented nucleic acids are recombined, e.g., with a with a set of crossover family diversity oligonucleotides. Each of these crossover oligonucleotides have a plurality of sequence diversity domains corresponding to a plurality of sequence diversity domains from homologous or non-homologous nucleic acids with low sequence similarity. The fragmented oligonucleotides, which are derived by comparison to one or more homologous or non-homologous nucleic acids, can hybridize to one or more region of the crossover oligos, facilitating recombination.

When recombining homologous nucleic acids, sets of overlapping family gene shuffling oligonucleotides (which are derived by comparison of homologous nucleic acids and synthesis of oligonucleotide fragments) are hybridized and elongated (e.g., by reassembly PCR), providing a population of recombined nucleic acids, which can be selected for a desired trait or property. Typically, the set of overlapping family shuffling gene oligonucleotides include a plurality of oligonucleotide member types which have consensus region subsequences derived from a plurality of homologous target nucleic acids.

Typically, family gene shuffling oligonucleotide are provided by aligning homologous nucleic acid sequences to select conserved regions of sequence identity and regions of sequence diversity. A plurality of family gene shuffling oligonucleotides are synthesized (serially or in parallel) which correspond to at least one region of sequence diversity.

Sets of fragments, or subsets of fragments used in oligonucleotide shuffling approaches can be provided by cleaving one or more homologous nucleic acids (e.g., with a DNase), or, more commonly, by synthesizing a set of oligonucleotides corresponding to a plurality of regions of at least one nucleic acid (typically oligonucleotides corresponding to a full-length nucleic acid are provided as members of a set of nucleic acid fragments). In the shuffling procedures herein, these cleavage fragments (e.g., fragments of monooxygenases) can be used in conjunction with family gene shuffling oligonucleotides, e.g., in one or more recombination reaction to produce recombinant monooxygenase nucleic acids.

10. Chimeric shuffling templates

In addition to the naturally occurring, mutated and synthetic oligonucleotides discussed above, polynucleotides encoding chimeric polypeptide can be used as substrates for shuffling in any of the above-described shuffling formats. Nucleic acids encoding chimeras prepared by art-recognized are encompassed herein. Art-recognized methods for preparing chimeras are applicable to the methods described herein (see, for example, Shimoji et al., *Biochemistry* 37: 8848–8852 (1998)).

Thus, in another embodiment, the invention provides a chimeric monooxygenase polynucleotide shuffling template. Preferred templates are derived from the P-450 superfamily of monooxygenases.

Cytochrome P450 constitutes a super family of over 1000 members. These proteins are grouped based on their heme prosthetic group and alignments. The sequence identity between the various P450 families is quite low, but the protein three dimensional folds are very similar. Hence alignments can easily be made between P450's using multiple sequence alignment tools such as clustal, DIALIGN, FASTA, MEME, and Block Maker. If a number of programs are used, a consensus alignment is evident, especially around critical residues such as the cysteine bound to the heme.

There are four P450 crystal structures known, P450 -cam, -terp, -eryF and -BM-P, and they all show similar architecture. Although all of the known crystal structures are for bacterial P450, when alignments are done to mammalian enzymes, predictions about the active site pockets and residues can be made. Site directed mutation studies based upon this scheme have experimentally verified the importance of the predicted residues in substrate binding (Gotoh, *J. Biol. Chem.* 267:83–90) describes a model of CYP 2C9, based on P450cam, which others have used and verified. For use of the BM-P structure to model/mutate CYP 4A proteins, see, *J. Biol. Chem. Sep* 4; 273(36):23055–61 (1998).

In another aspect, the invention provides a method of obtaining a polynucleotide that encodes a recombinant P450 polypeptide comprising a backbone domain and an active site domain. The method involves: (a) recombining at least first and second forms of a nucleic acid that encodes a P450 active site domain, wherein the first and second forms differ from each other in two or more nucleotides to produce a library of recombinant active site domain encoding polynucleotides; and (b) linking the recombinant active site domain-encoding polynucleotide to a backbone-encoding polynucleotide so that the active site-encoding domain and the backbone-encoding domain are in-frame.

In yet another aspect, the invention provides a method of obtaining a polynucleotide that encodes a recombinant P450 polypeptide comprising a backbone domain and an active site domain. The method involves: (a) recombining at least first and second forms of a nucleic acid that encodes a P450 backbone domain, wherein the first and second forms differ from each other in two or more nucleotides to produce a library of recombinant backbone domain encoding polynucleotides; and (b) linking the recombinant backbone domain-encoding polynucleotide to a active site-encoding polynucleotide so that the backbone-encoding domain and the active site-encoding domain are in-frame.

In a still further aspect, the invention provides a method of obtaining a polynucleotide that encodes a recombinant P450 polypeptide comprising a backbone domain and an active site domain. The method involves: (a) recombining at least first and second forms of a nucleic acid that encodes a P450 active site domain, wherein the first and second forms differ from each other in two or more nucleotides to produce a library of recombinant active site domain encoding polynucleotides; (b) recombining at least first and second forms of a nucleic acid that encodes a P450 backbone domain, wherein the first and second forms differ from each other in two or more nucleotides to produce a library of recombinant backbone domain encoding polynucleotides; and (c) linking the recombinant active site domain-encoding polynucleotide to the recombinant backbone-encoding polynucleotide so that the recombinant active site-encoding domain and the recombinant backbone-encoding domain are in-frame.

The linking of the various nucleic acids in each of the above aspects can be accomplished by methods well-known in the art. Moreover, in each of the above aspects, certain embodiments are presently preferred. For example, in a preferred embodiment, the backbone P450 (BM-P in this example) refers to the C-terminus of the protein which contains the proximal cysteine (residue 400) ligand to the prosthetic heme. The N terminus of the desired P450 isozyme is transferred onto this structure. In a preferred embodiment the junction between the two sequences occurs at an end of the I helix (e.g., residue 282). In another preferred embodiment the junction between the two proteins occurs in the G-H loop (residues 227–232 preferably). In another preferred embodiment solely the F and G helices (residues 171–226) are transferred into the backbone P450 with the remaining sequence being from the backbone P450.

Using the above methods, chimeric monooxygenases having optimized activities can be obtained. The activities that are optimized include any of the activities towards any of the substrates described herein.

Generating a focused P450 library of chimeras, steroid hydroxylases for example, typically begins with an investigation of the literature, especially the drug metabolism area, for isozymes known to catalyze the desired chemistry. Once identified, these isozymes are aligned, using the relevant programs, to one of the P450's with a known x-ray structure (P450 -cam, -terp, -eryF and -BM-P), preferably BM-P. Once the alignment is achieved, the putative active site regions are generated and isolated for further study.

Inspection of the published structures for P450's (see, for example *P.N.A.S.* 96: 1863–1868 (1999); *Nature Struct. Biol.* 4: 140–146 (1997)) and structure function studies (see, for example, *Drug Metab. Dispos.* 26: 1223–1231 (1998), for a review) and are used to highlight the sites at which chimeras are preferably constructed. For the purpose of clarity, all residue numbers refer to an exemplary sequence, CYP 102 P450 BM-P. This focus is not intended to limit the invention as it is apparent that it is the positions in the structural motif of the protein that are relevant not the absolute residue number. The positions of the structural motifs may be determined by methods including crystal structure determination, sequence alignment and homology modeling. Indeed a small extension of the sequence beyond the chosen region may be transferred into the chimera.

The method provides a series of chimeric nucleic acids which include sequences, chosen as described above, from the P450 isozymes known to catalyse the desired chemistry and the remainder of a soluble bacterial P450, preferably one of the structurally defined P450s, most preferably P450BM-P, most preferably still an already improved chimeric monooxygenase nucleic acid. These chimeric nucleic acids can be used as substrates for shuffling in any of the above-described shuffling formats.

In one embodiment the entire polynucleotide is improved by shuffling. In a preferred embodiment, the heme domain of the P450 component of the chimera is shuffled. In another preferred embodiment the active site region of the P450 isozymes is shuffled. In yet another preferred format the active site sequences described above are shuffled before chimera formation. In this format the improved nucleic acids are cloned into the P450 backbone to create a library of improved monooxygenases In another preferred format, one or more of the desired P450 isozyme active sites are not transformed into a chimeric nucleic acid. The diversity encoded by these sequences are captured by the inclusion of oligonucleotides encoding the sequence of interest as described in the above-described shuffling format.

One advantage of this process is that the formation of chimeric P450 nucleotides allows the production of polypeptide encoding any P450 activity in the same system. Thus the creation of an improved nucleic acid with one activity may start from a previously improved chimeric nucleic acid encoding a different activity. This recursive synergy leads to rapid improvement of the monooxygenase nucleic acid for any and all of the desired properties.

Another advantage of this process is the improvement in stability and ease of expression of polypeptides with the activity of a eukaryotic, membrane associated, P450 as a soluble bacterial protein. This leads to significant improvement in the expression level, stability, and ease of handling of any polypeptide encoded by the improved nucleic acid.

A third advantage of this process is the ability to create improved nucleic acids for a particular activity without isolation of the nucleic acid encoding that activity. Each chimeric nucleic acid will be expressed and screened in substantially similar fashion for any of the reactions described herein.

Thus any reaction described in the literature of biotransformation and drug metabolism and known to those skilled in the art, such as those described herein, encoded by a P450 nucleic acid can be performed by a chimeric nucleic acid of the type described.

B. Reactions of Improved Monooxygenases

In another aspect, the invention provides a method for obtaining a polynucleotide encoding an improved polypeptide acting on a substrate comprising a target group selected from an olefin, a terminal methyl group, a methylene group, an aryl group and combinations thereof. The improved polypeptide exhibits one or more improved properties compared to a naturally occurring polypeptide acting on said substrate. The method includes: (a) creating a library of recombinant polynucleotides encoding a monooxygenase polypeptide acting on said substrate; and (b) screening said library to identify a recombinant polynucleotide encoding an improved polypeptide that exhibits one or more improved properties compared to a naturally occurring monooxygenase polypeptide.

In a preferred embodiment, the library of recombinant polynucleotides is created by recombining at least a first form and a second form of a nucleic acid. At least one of these forms encodes the naturally occurring polypeptide or a fragment thereof. Preferably, the first form and said second form differ from each other in two or more nucleotides. In a further preferred embodiment, the first and second forms of the nucleic acid are homologous.

In addition to the methods described above for producing the encoding polynucleotides, the present invention also provides the polypeptides encoded by these polynucleotides and methods using these peptides for synthesizing valuable organic compounds. Some of these polypeptides and methods of using them are set forth below.

It is noted that the basic chemistry described below with reference to monooxygenases is known. In addition to Ortiz de Montellano, supra, a general guide to the various chemistries involved is found in Stryer (1988) BIOCHEMISTRY, third edition (or later editions) Freeman and Co., New York, N.Y.; Pine et al. ORGANIC CHEMISTRY, FOURTH EDITION (1980) McGraw-Hill, Inc. (USA) (or later editions); March, ADVANCED ORGANIC CHEMISTRY REACTIONS, MECHANISMS and Structure, 4th ed, J. Wiley and Sons (New York, N.Y., 1992) (or later editions); Greene, et al., PROTECTIVE GROUPS IN ORGANIC CHEMISTRY, 2nd Ed., John Wiley & Sons, New York, N.Y., 1991 (or later editions); Lide (ed) THE CRC HANDBOOK OF CHEMISTRY AND PHYSICS 75TH EDITION (1995)(or later editions); and in the references cited in the foregoing. Furthermore, an extensive guide to many chemical and industrial processes applicable to the present invention is found in the KIRK-OTHMER ENCYCLOPEDIA OF CHEMICAL TECHNOLOGY (third edition and fourth edition, through year 1998), Martin Grayson, Executive Editor, Wiley-Interscience, John Wiley and Sons, NY, and in the references cited therein ("Kirk-Othmer").

The following chemistries illustrate those generally accessible through the heme-dependent P450 monooxygenase/peroxidase superfamily. Certain useful reaction types are set forth in FIG. 1.

Family shuffling approaches apply to enhancing performance of monooxygenase polypeptides useful in each of the following classes of industrial chemical transformation. Other monooxygenase enzyme classes are also useful in practicing the present invention. Moreover, other polypeptides accessible through the present invention, and method of using these polypeptides will be apparent to those of skill in the art.

1. Oxidation of π-bonds to epoxides

Among the most high-value classes of commodity chemical transformations is the catalytic epoxidation of terminal olefins to corresponding epoxides. Indeed, ethylene oxide, propylene oxide, epichlorohydrin, glycidol, butylene oxide and bis-A-diglycidyl ethers and their immediate downstream derivatives account for a significant fraction of the entire $350 B/yr global chemical industry. Typically, prior art P450 activities are limited by low turnover number, low affinity, low stability under the conditions of interest and/or enzyme inactivation by alkylation or free-radical-dependent mechanisms. Moreover, such chemistry is often associated with rapid inactivation of the heme-dependent enzyme. Family shuffling approaches to enzyme improvement are used to markedly reduce the sensitivity of the monooxygenases to this mode of inactivation.

In a preferred embodiment, the present invention provides an improved polypeptide that is capable of converting an olefin into an epoxide. Moreover, there is provided a method for converting an olefin to an epoxide. The method includes contacting the olefin substrate with the polypeptide. In a still further preferred embodiment, the substrate is contacted with an organism that expresses the polypeptide.

In another preferred embodiment, the polypeptides are those encoded by monooxygenase genes that can be recruited and optimized by DNA shuffling. A range of monooxygenases known in the art provide appropriate starting points for determining a polypeptide useful in this aspect of the invention. One useful class of monooxygenases is exemplified by the heme-dependent eukaryotic and bacterial cytochrome P-450.

Heme-containing enzymes of the P450 family exhibit a wide array of catalytic activities of interest in the context of metabolizing xenobiotics and environmental and biochemical waste products. Of the diverse chemistries catalyzed by this class of enzymes, a number are of industrial chemical interest.

As an enzyme class, the P450 family exhibits notable activities toward many classes of compounds. For example, in the presence of oxygen and an intact redox recycle system, P450s exhibit monooxygenase activity. Addition of hydrogen peroxide or other peroxides, however, can be used to circumvent the NAD(P)H requirement (i.e. allowing for peroxidase activity) toward many of the same substrates.

In a further preferred embodiment, polypeptides based on, or analogous to, non-heme-dependent monooxygenases are used to effect epoxidation of olefins. Such monooxygenases include, but are not limited to, non-heme monooxygenases involved in the bacterial degradation of styrene by bacteria (as exemplified by the genes and enzymes described by Marconi et al., *Appl. Environ. Microbiol.* 62(1): 121–127 (1996); Beltrametti et al., *Appl Environ. Microbiol.* 63(6): 2232–2239 (1997); O'Connor et al., *Appl. Environ. Microbiol.* 63(11):4287–4291 (1997); Velasco et al., *J. Bacteriol.* 180(5):1063–1071 (1998); Itoh et al., *Biosc. Biotechnol. Biochem.* 60(11):1826–1830 (1996)), or in the degradation of methyl-substituted aromatic compounds such as toluene, xylenes, p-cymene (exemplified by xylene monooxygenase, Wubbolts et al., *Enzyme Microb. Technol.* 16(7):608–615 (1994)).

The following is a non-limiting list of exemplary monooxygenase genes which can be recruited and optimized by DNA shuffling for the purpose of epoxidizing olefins:

[AF031161] styrene monooxygenase (epoxide-forming) of Pseudomonas sp. VLB120, stdA, stdB; [PFSTYABCD] styrene monooxygenase of *P. fluorescens* (styA, styB); [PSSTYCATA] styrene monooxygenase of Pseudomonas sp.; [PSEXYLMA, AF019635, D63341, E02361] xylene/toluene monooxygenase of *Pseudomonas putida* TOL plasmid (xyl M, xylA); [PPU24215] p-cymene monooxygenase of *P. putida*; [PSETBMAF] toluene/benzene-2-monooxygenase (tbmA-tmmF) of Pseudomonas sp.; [PPU04052] toluene-3-monooxygenase of *seudomonas. pickettii* PKO1; [AF001356] toluene-3-monooxygenase of *Burkholderia cepacia*; and [AF043544] nitrotoluene monooxygenase of Pseudomonas sp. TW3, NtnMA (ntnM, ntnA).

A variety of strains known to contain monooxygenases capable of epoxide formation are known. For example, *Pseudomonas aeruginosa* is known to have a monooxygenase capable of epoxidizing 1-octene to 1,2-epoxyoctane. The most comprehensive studies on bacterial alkene epoxidation have been done on *Pseudomonas oleovorans*. Work on *P. oleovorans* by May and coworkers (*J. Biol. Chem.* 248:1725–1730, 1973) shows that the monooxygenase contained in the cells is capable of epoxidizing octene to 1,2-epoxy-octane in 70% enantiomeric purity. In addition, this enzyme is capable of converting 1,7-octadiene to the diepoxide (May et al., *J. Am. Chem. Soc.* 98:7856–7858) and 1,5-hexadiene and 1,11-dodecadiene to epoxides. However, smaller alkenes are often converted to alcohols. Cells grown up overnight under standard conditions can be used intact or as lysates—and, in both cases, have been observed to give yields of ~1 g/L. Increasing the rate of accumulation of the reactive epoxide is clearly one of the preferred objectives of gene shuffling as set forth herein.

This enzyme system is also capable of mediating hydroxylation of longer chain alkanes (octanes, etc.) and fatty acids. The enzyme has been cloned and sequenced and is included of three protein components: rubredoxin (mw 19,000), NADH-rubredoxin reductase, and the hydroxylase (a non-heme iron protein). Whereas there are scenarios (such as when overall stability of the system is an issue) in which shuffling of the genes for all three protein components is preferred, when the primary improvement is related to the kinetics, affinity or inhibition profile of the monooxygenase, the preferred shuffling strategy will be to shuffle homologs of the hydroxylase (epoxygenase) component.

Microorganisms having MO enzyme activities with similar properties include the genera Rhodoccous, Mycobacterium, Nocardia (*Nocardia carollina* B-276) and *Pseudomonas Corynebacterium* equi (IFO 3730), which can be grown on n-octane and which exhibit the capacity to oxidize 1-hexene to optically pure (R)-(+)-epoxide. This strain also assimilates other terminal olefins and converts them to epoxides. Yields decrease to <1% with carbon chains of >14. Increasing the activity of the enzyme toward longer chain length alkenes is a target for evolving additional catalysts for chirally selective epoxidations. Such monomers have high value as pharmaceutical and agricultural intermediates.

Experiments with *Pseudomonas putida*, *Nocardia corallina* B-276 and *Bacillus megaterium*, suggest that the monooxygenase activity of these organisms derives from a soluble P450-dependent system. All of these strains are available from ATCC and serve as exemplary sources for the genes which can be isolated by hybridization and gene amplification methods.

Mycobacterium sp (E20) and Mycobacterium sp. (Py 1) show activity even toward short-chain, gaseous olefins such as ethylene. In the case of both ethylene and propylene, the epoxide products are formed almost exclusively. Catalyst performance experiments are performed in a gas-solid reactor to prevent accumulation of toxic ethylene oxide in the immediate vicinity of the biocatalyst. An experimental set-up which allows for automatic gas chromatography analysis of circulation gas in a batch reactor system and allows for online monitoring of the microbial (or enzymatic) oxidation of gaseous alkenes (ethylene, propylene and butylene). Optimization of the process is achieved by studying the influence of various organic solvents and physical conditions on retention of immobilized cell/enzyme activity.

High activity retention is favored by low polarity, high molecular weight solvents; although this is also selectable following DNA shuffling as well. Using chiral gas chromatography, wild type (wt) strains and strains containing candidate evolved polypeptides are screened with respect to the stereospecificity of the epoxidation of propene, 1-butene and 3-chloro-1-propene. Results show that a wide range of chiral selectivity or nonselectivity emerge from a typical series of family shuffling and screening experiments. Novel polypeptides, favoring the S, rather than the R stereoisomer can also be shuffled and selected. Inactivation of the alkene epoxidation system by the produced epoxide has been one of the key historical limitations of the system. Again, gene and family shuffling combined with appropriate selection methods and screens are used to identify polypeptides with improved stability in the presence of epoxide products.

A number of other methane-grown methylotrophic bacteria (*Methylosinus trichosporium, Methylobacterium capsulatus* and *Methylobacterium organophilum*) have all been shown to contain a methane monooxygenase (MMO) system analogous to the well-characterized *Pseudomonas oleovorans* system. Again, standard hybridization and gene amplification methods provide a straightforward approach to isolate those genes which are not yet reported in the literature. Sequences of MMOs from some of these organisms are known and can be obtained from the public sequence Databases such as Genbank, Entrez®, and others.

Moreover, one species of *Rhodococcus rhodochrous* has been shown to be capable of oxidizing propane and propene to epoxide and hydroxylated products without inhibition by the products. The unique monooxygenase from this organism provides an important material to incorporate in family shuffling formats to expand activity of shuffled nucleic acids.

2. Hydroxylation of organic substrates

In another embodiment, the present invention provides a monooxygenase polypeptide capable of hydroxylating organic substrates. In an exemplary embodiment, the polypeptide oxidizes a methyl or a methylene group. In a preferred embodiment, the polypeptide oxidizes a terminal methyl group to a hydroxymethyl group. In yet another preferred embodiment, the invention provides an improved monooxygenase polypeptide that acts on a methylene group to form a secondary alcohol. Preferred organic substrates include a target group selected from arylmethyl, substituted arylmethyl, arylmethylene, substituted arylmethylene, heteroarylmethyl, substituted heteroarylmethyl, alkylterminal methyl, fatty acid, terpenes and combinations thereof. The improved polypeptide is prepared using the methods of the invention and exhibits one or more improved properties compared to a naturally occurring polypeptide.

In addition to the polypeptide, there is provided a method for converting a terminal methyl or internal methylene into the corresponding alkyl hydroxy group. The method includes contacting the substrate with the polypeptide. In a still further preferred embodiment, the substrate is contacted with an organism that expresses the polypeptide.

P450s mediate the conversion of many of the molecular species listed above, including oxidation of toluene to form benzyl alcohol and oxidation of 2-phenyl-propane to 2-pheny-1-propanol. Monooxygenase enzymes from *Pseudomonas gladioli*, *Aspergillis niger* and other species are known to oxidize monoterpenes as well as higher terpenes. Conversion of monoterpenes to terminal unsaturated alcohols (without disruption of alkene functionalities) is a remarkable aspect of monooxygenase mediated conversions (see, ENZYME CATALYSIS IN ORGANIC SYNTHESIS, VOL. II, Chapter B.6.1.4 (ed. By K. Drauz and H. Waldmann, VCH Publishers, Inc., 1995). The powerful monooxygenase system of *Pseudomonas oleovorans* is also known to transform linear and branched-chain alkanes to alcohols, aldehydes, acids and hydroxy acids.

Members of the P450 superfamily typically favor formation of primary alcohols. An example of a P450-mediated hydroxylation of interest is the ω and ω-1 hydroxylation of fatty acids, such as lauric acid. P450s such as CYP2B4, CYP2B1 and related sequences demonstrate this activity toward a number of hydrocarbon substrates. Shuffling members of this subfamily leads to polypeptides with altered specificity and enhanced stability.

Many polypeptides capable of arylmethyl group oxidation are well known in the art. For example, the introduction of oxygen into methyl groups and methylene groups is mediated by non-heme multicomponent monooxygenases of toluene, xylenes and p-cymene.

While much of the discussion above focuses on constructing polypeptides and pathways for oxidation of arylmethyl compounds, this discussion is also directly applicable to polypeptides and pathways for oxidizing terminal methyl and internal methylene groups of both alkyl and aryl-substituted alkyl groups. In a preferred embodiment, the substrate is an aryl-substituted alkyl group (see, FIG. 2).

This step is accomplished by recruiting one or more genes encoding an appropriate monooxygenase activity. In a preferred embodiment, this is accomplished by shuffling and expressing a suitable cytochrome P450 type enzyme system. The enzymes of this class are ubiquitous in nature, and they can be found in a variety of organisms. For example, n-propylbenzene is known to undergo α-oxidation in strains of *Pseudomonas desmolytica* S449B1 and *Pseudomonas convexa* S107B1 (Jigami et al., *Appl. Environ. Microbiol.* 1979 38(5):783–788).

Similarly, alkane monooxygenases of bacterial origin, or cytochromes P450 for camphor oxidation, whether wild-type or mutant, can be recruited for the purpose of introducing the oxygen into the terminal methyl group of alkylaryl compounds, wherein the alkyl group is generally other than a methyl group (Lee et al., *Biochem. Biophys. Res. Commun.*; 218(1):17–21 (1996); van Beilen et al., *Mol. Microbiol.*; 6(21):3121–3136 (1992); Kok et al., *J. Biol. Chem.* 264(10):5435–5441 (1989); Kok et al.,*J. Biol. Chem.* 264(10):5442–5451 (1989); Loida and Sligar, *Protein Eng.* 6(2):207–212 (1993)). Furthermore, the mammalian metabolic pathways for these and structurally related alkylaromatic hydrocarbons indicate a cytochrome P450 dependent chiral oxidation of the terminal methyl group and subsequent oxidation to corresponding 2-arylpropanoic or 2-arylacetic acids, indicating that these P450s are excellent shrffling substrates (Matsumoto et al., *Chem. Pharm. Bull. (Tokyo)* 40(7):1721–1726 (1992); Matsumoto et al., *Biol. Pharm. Bull.* 17(11):1441–1445 (November 1994); Matsumoto et al., *Chem. Pharm. Bull. (Tokyo)* 43(2):216–222 (1995); Ishida and Matsumoto, *Xenobiotica* 22(11): 1291–1298 (1992)).

Examples of monooxygenase genes suitable for use in the construction of strains for oxidation of the methylarenes include:

[PSEXYLMA, AF019635, D63341, E02361] xylene/toluene monooxygenase of *Pseudomonas putida* TOL plasmid (xyl M, xylA); [PPU24215] p-cymene monooxygenase of *P. putida*; [AF043544] nitrotoluene monooxygenase of Pseudomonas sp. TW3, NtnMA (ntnM, ntnA); [SMU40233 and SMU40234] alkane monooxygenase of *Stenotrophomonas maltophilia*; [POOCT] alkane monooxygenase of *Pseudomonas oleovorans* TF4-1L (+OCT) plasmid, alk genes; and camphor 5-monohydroxylase of *P.putida* (CAM plasmid)

Alternatively, for the purpose of using of non-heme-dependent oxidation of the arylalkyl compounds, useful monooxygenases are exemplified by a variety of non-heme monooxygenases involved in the bacterial degradation of styrene by bacteria (as exemplified by the corresponding genes and enzymes described by Marconi, et al., *App.l Environ. Microbiol.* 62(1):121–127 (1996); Beltrametti, et al., *Appl. Environ. Microbiol.* 63(6):2232–2239 (1997); O'Connor, et al., *Appl. Environ. Microbiol.* 63(11): 4287–4291 (1997); Velasco, et al., *J. Bacteriol.* 180(5): 1063–1071 (1998); Itoh, et al., *Biosc.i Biotechnol. Biochem.* 60(11):1826–1830 (1996)); or in the degradation of methyl-substituted aromatic compounds such as toluene, xylenes, p-cymene (exemplified by xylene monooxygenase, Wubbolts, et al., *Enzyme. Microb. Technol.* 16(7):608–615 (1994)).

Exemplary non-heme monooxygenases useful in practicing the present invention include:

[AF031161] styrene monooxygenase (epoxide-forming) of Pseudomonas sp. VLB 120, stdA, stdB, [PFSTYABCD] styrene monooxygenase (epoxide-forming) of *P. fluorescens* (styA, styB); [PSSTYCATA] styrene monooxygenase (epoxide-forming) of Pseudomonas sp; [PSEXYLMA, AF019635, D63341, E02361] xylene/toluene monooxygenase of *Pseudomonas putida* TOL plasmid (xyl M, xylA); [PPU24215] p-cymene monooxygenase of *P. putida*; [PSETBMAF] toluene/benzene-2-monooxygenase (tbmA-tmmF) of Pseudomonas sp.; [PPU04052] toluene-3-monooxygenase of *Pseudomonas pickettii* PKO1; [AF001356]; toluene-3-monooxygenase of *Burkholderia cepacia*; [AF043544] nitrotoluene monooxygenase, of Pseudomonas sp. TW3, NtnMA (ntnM, ntnA).

3. Aromatic hydroxylation

Hydroxylated aromatic compounds are an important group of industrial chemicals. Carboxylic acids, esters and lactones of hydroxylated aromatic compounds are of particular value and interest. Thus, in another preferred embodiment, the invention provides an improved monooxygenase polypeptide that can oxidize an aryl compound to a hydroxyaryl compound (FIG. 1). Additionally, there is provided a method utilizing an improved monooxygenase polypeptide to effect the transformation of an aryl group to a heteroaryl group. The method includes contacting a substrate comprising an aryl group with the polypeptide. In yet another preferred embodiment, the substrate is contacted with an organism that expresses the polypeptide.

Presently preferred substrates include, for example, aryl groups, substituted aryl groups, heteroaryl groups and substituted heteroaryl groups. Compounds representative of these generic groups include industrially significant substrates such as biphenyl, benz-[a]-pyrene, aniline, toluene, naphthalene, cumene, haloaromatics and phenanthrene.

Many monohydroxy aromatic compounds can be generated by using heme- and/or non-heme-containing type monooxygenases. To be useful in the biotransformation pathway, preferred polypeptides will have a sufficiently high turnover rate and they will not be readily deactivated in the presence of the substrates, intermediates or products of the oxidation reaction. This characteristic is an ideal candidate for improvement by the shuffling process disclosed herein.

This class of reactions includes, for example, the modification of such industrially significant substrates as benzene, biphenyl, benz-[a]-pyrene, aniline, toluene, naphthalene, cumene, haloaromatics and phenanthrene are all of considerable industrial chemical importance and are all carried out by members of the P450 superfamily.

4. S-dealkylation of alkylsulfur compounds

S-Dealkylation of reduced thio-organics, such as oxidation of parathion can be mediated by the use of improved monooxygenases. Sulfoxidation of numerous organosulfur compounds is also observed and can be enhanced by shuffling monooxygenases. Thus, in another preferred embodiment, the invention provides an improved monooxygenase polypeptide that can oxidize a penicillin G to penicillin G S-oxide, a key intermediate in the synthesis of cephalosporins.

5. O-Dealkylation of alkyl ethers

Whereas S and N-alkyl groups are oxidized by monooxygenases to the corresponding oxides, the electronegativity of oxygen dictates a different mechanistic pathway, namely rearrangement of the O-alkyl bond. Synthetic pathways utilizing this reaction motif can be improved by shuffling monooxygenases.

6. Oxidation of aryloxy phenols

Monooxygenase mediated reactions such as the conversion of p(p-nitrophenoxy)phenol to quinone can be enhanced by shuffling monooxygenases.

7. Dehydrogenation

In some cases, the monooxygenase polypeptides of the invention operate as dehydrogenases rather than as oxygenases or peroxidases. For example, conversion of saturated hydrocarbons to unsaturated, conversion of alcohols to aldehydes, carboxylic acids and ketones, conversion of aldehydes to carboxylic acids and the desaturation of nitrogen compounds has been observed. A classic example of this is the conversion of dihydronaphthalene to naphthalene. Conversion of valproic acid to 2-n-propyl-pentenoic acid also illustrates this chemistry as does conversion of lindane (1,2,3,4,5,6-hexachlorocyclohexane) to hexachlorocyclohexene. Numerous other examples of this classic P450 chemical transformation exist, such as conversion of acetaldehyde or propionaldehyde to acetic and propionic acid, respectively. The CYP2C29 enzyme, for example, converts aliphatic alpha-beta unsaturated aldehydes (and anthraldehyde) to the corresponding acids. Shuffling of these and related P450s provides improved properties, such as enhanced activity, specificity and/or P450 stability.

Moreover, P450-based dehydrogenation chemistry also plays an important role in the biosynthesis of various steroids, and is, therefore, of considerable commercial interest in synthesizing steroid-based pharmaceuticals such as cortisol and other steroidal anti-inflammatory agents.

Thus, in another embodiment, the present invention provides a method for obtaining a nucleic acid encoding an improved monooxygenase polypeptide having dehydrogenase activity. In a preferred embodiment, the improved polypeptide acts on a substrate to dehydrogenate a hydroxyalkyl group to a member selected from:

—COOH, and —C(O)H.

Preferred substrates include members selected from the group of arylmethyl, substituted arylmethyl, heteroarylmethyl, substituted heteroarylmethyl, alkyl-terminal methyl, substituted alkyl-terminal methyl, and the like, as well as combinations thereof.

The improved polypeptide of the invention exhibits one or more improved properties compared to a naturally occurring polypeptide. Producing the polypeptide by the method of the invention involves creating a library of recombinant polynucleotides encoding a polypeptide acting on the substrate; and screening the library to identify a recombinant polynucleotide encoding the improved polypeptide.

Moreover, there is provided a dehydrogenase polypeptide prepared by the method of the invention. A method for utilizing this polypeptide to oxidize a hydroxyalkyl group using the polypeptide is also provided. The method involves contacting a substrate having a hydroxyalkyl group with a polypeptide of the invention, more preferably with an organism expressing a polypeptide of the invention.

8. Decarbonylation

Examples of this important chemistry include conversion of cyclohexanecarboxaldehyde to cyclohexane and formic acid. Conversion of isobutyraldehyde, trimethylacetaldehyde, isovaleraldehyde, 2-methyl-butyraldehyde, citronellel and 2-phenyl-propionaldehyde to their corresponding decarbonylated products are also observed. This chemistry is not observed with unbranched aldehydes such as propionaldehyde and valeraldehyde. This is an important class of catalytic chemistry not easily duplicated abiotically. CYP2B4 is a preferred target for shuffling to improve the native activity of this P450. Shuffling of this family of P450 MOs results in polypeptides with activity toward unbranched aldehydes such as adipaldehyde, valeraldehyde and/or propionaldehyde.

10. Oxidative dehalogenation of haloaromatics and halohydrocarbons

Exemplary substrates for these reaction include, polychlorobenzenes, trichloroethylene, di and trichloro propane, 1,2 dichloroethane and 1,2 1,3 and 1,4 dihydroketones.

11. Baeyer-Villiger monoxygenation

This reaction involves the oxidation of aromatic, open-chain and cyclic ketones to esters and lactones.

12. Exemplary embodiments utilizing monooxygenases a. Cyclosporin

Cyclosporin A is a nonribosomal peptide drug with antifungal and immunosuppressive properties that is widely used as an immunosuppressant after transplant surgery. There currently exist at least 25 cyclosporin derivatives with various properties, and there is a great demand for new cyclosporin molecules. The creation of new derivatives, however, has been hampered by the difficult synthetic chemistry of these large natural product molecules (MW ~1200). Therefore, a means of overcoming this limitation of traditional chemistry is of great value.

Cytochrome P450 and other monooxygenase enzymes provide an alternative method of making modified cyclosporins. The P450 3A subfamily contains members with various activities on cyclosporin A; for example, the 3A5 enzyme can hydroxylate the amino acid at position 1, and 3A4 can hydroxylate amino acids 1 and 9 as well as demethylate position 4 (Aoyama et al., JBC 264:10388). Other activities exist among the large 3A subfamily, consisting of at least 30 members (see, http://drnelson.utmem.edu/homepage.html).

Alignment of 14 of these 3A genes shows homologies of 67–99%. Such diversity is ideal for shuffling, and provides a means of creating additional genetic diversity in the form of P450 libraries, with concomitant enzymatic diversity. Initial screening for new or improved activities can be done in bacteria, as the human 3A4 enzyme and its accessory reductase are functional in *E. coli* (Parikh et al., *Nature Biotechnol.* 15:784). Activity of clones in libraries can be measured by high throughput mass spectroscopy detection of product molecules, for example. DNA from clones with improved activity can be isolated and shuffled to recombine beneficial mutations, followed by screening for even better activity.

b. Pravastatin

Pravastatin is a steroid drug which lowers serum cholesterol by competitive inhibition of the cholesterol biosynthetic enzyme HMG-CoA reductase. Pravastatin (marketed as Pravachol™ by Bristol-Myers Squibb) is produced by a two-step fermentation (Serizawa et al IN BIOTECHNOLOGY OF ANTIBIOTICS 2ND EDITION, W. R. Stfohl (ed.) (1997) New York: Mascel-Dekker, pp. 777–805): production of the precursor mevastatin by *Penicillium citrinum*, and then hydroxylation of mevastatin to pravastatin by a cytochrome P450 enzyme in *Streptomyces carbophilus*.

This invention provides a method to make the second step of this synthesis more efficient by increasing the ability of the *S. carbophilus* P450 to hydroxylate mevastatin. The value of this improvement is in decreasing the cost of drug synthesis; much work has already gone into optimizing culture conditions (Serizawa et al., 1997), an indication that it is an expensive process.

The P450 that converts mevastatin to pravastatin has been characterized in some detail (Watanabe et al, *Gene* 163:81–85. (1995)). The gene cytP-450$_{sca-2}$ has been cloned and shows homology to other bacterial P450 genes, including 78% identity with the *S. griseolus* gene suaC, whose product is involved in herbicide detoxification (Omer et al., *Nature* 288–291 (1998)), and over 50% identity with several other P450 genes (see below). CytP-450$_{sca-2}$ is functional when overexpressed in the laboratory strain *S. lividans*.

TABLE 1

DNA homology between selected cytochrome P450 genes.

| CYP105A1 suaC | CYP105D1 soyC | CYP105B1 subC | CYP105A2 | Sca2 | |
|---|---|---|---|---|---|
| — | 58% | 51 | 56 | 78 | 105A1 |
| | — | 51 | 48 | 57 | 105D1 |
| | | — | 56 | 52 | 105B1 |
| | | | — | 53 | 105A2 |
| | | | | — | Sca2 |

Improvement of the ability of CytP-450$_{sca-2}$ to convert mevastatin to pravastatin can be accomplished by DNA shuffling. The known sequences provide an ideal platform for the family shuffling technique, wherein related, functional genes are shuffled together to create the initial library for screening/selection. Some of these genes can be obtained directly from the microbe in which they were identified (e.g., CYP105A1 and CYP105B1 from *S. griseolus* strain ATCC11796, see Omer et al., 1990). Others genes such as CytP-450$_{sca-2}$ can be assembled from synthetic oligonucleotides. The initial family shuffling can be done as described (Crameri et al., 1998). The initial screen for improved clones can be done in a surrogate host, such as *E. coli* or *S. lividans*; cells can be cultured in mevastatin (or the related compound ML-236B•Na; see Watanabe et al., 1995, above) and the production of pravastatin detected by high throughput techniques, probably mass spectroscopy. The hydroxy group will easily differentiate the product from the substrate. The genes can be rescued from the best clones and shuffled together in subsequent cycles. The final test would be in an environment resembling actual fermentation conditions as much as possible.

c. Herbicide Resistance and Bioremediation

One set of P450 gene products with activity against herbicides consists of SuaC (CYP105A1) and SubC (CYP105B1) from *Streptomyces griseolus* (Omer et al., *J. Bacteriol.* 172:3335) and related genes from other bacteria. These enzymes are active against sulfonylurea herbicides such as chlorimuron ethyl, chlorsulfuron, and sulfomethuron methyl (Harder et al., *Mol. Gen. Genet.* 227:238). Related bacterial P450 genes have been identified, with DNA sequence homologies of 48–78% (see, Table 2 below). Because these genes are of bacterial origin, they are best suited to bioremediation uses but may also be useful for creating herbicide-resistant plants.

Another set of P450 genes can be isolated from plants with herbicide detoxification activities. Such activities are known to be due to plant cytochrome P450s (Lau and O'Keefe, *Methods Enzymol.* 272:235). It is possible to identify the genes, or at least portions of them, by using PCR primers targeted to conserved regions of P450s (Holton and Lester, *Methods Enzymol.* 272:275) which are responsible for this activity.

DNA family shuffling (Crameri et al., *Nature* 391:288) can be used to create hybrid variants from these genes, variants which can be screened for increased herbicide metabolism (detoxification). One way to screen for such activity in large numbers of samples is by measuring loss of fluorescence due to metabolism of the fluorescent sulfonylurea W5822 (DuPont) (see, Harder et al., *Mol. Gen. Genet.* 227:238). Other suitable screening systems employ mass spectroscopy, HPLC and other well-known analytical methods. Improved clones can be shuffled together in the next cycle of DNA shuffling for further improvement. The best genes can then be transferred to plants and tested for conferral of herbicide resistance; further optimization may be necessary to account for plant-specific factors. Likewise, for bioremediation uses, final improvement may be necessary in the ultimate host. Many additional herbicide applications of P450 shuffling are found in the U.S. Patent Application entitled "DNA Shuffling to Produce Herbicide Selective Crops" Attorney Docket Number 018097-025600US and assigned U.S. Ser. No. 60/096,288 filed Aug. 12, 1998.

Table 2 displays homology between selected cytochrome P-450 genes preferred for use in this embodiment of the invention.

TABLE 2

DNA homology between selected cytochrome P450 genes.

| CYP105A1 suaC | CYP105D1 soyC | CYP105B1 subC | CYP105A2 | Sca2 | |
|---|---|---|---|---|---|
| — | 58% | 51 | 56 | 78 | 105A1 |
| | — | 51 | 48 | 57 | 105D1 |
| | | — | 56 | 52 | 105B1 |
| | | | — | 53 | 105A2 |
| | | | | — | Sca2 |

In addition to these monooxygenase mediated reactions, the use of reactions that are mediated by polypeptides that do not have monooxygenase activity is also within the scope of the present invention. In a preferred embodiment, these non-monooxygenase polypeptides will operate on a substrate that has been acted on by a monooxygenase. In another preferred embodiment, these polypeptides will operate on a compound prior to its being acted on by a monooxygenase. Moreover, it is within the scope of the present invention to improve one or more properties of the non-monooxygenase polypeptides by shuffling nucleic acids encoding these polypeptides.

C. Accessory Polypeptides

In conjunction with the oxidative pathways utilizing polypeptides having monooxygenase activity, as discussed above, the present invention provides accessory non-monooxygenase polypeptides. As used herein, "accessory polypeptides" refers to those polypeptide that do not carry out the initial monooxidation step in the methods of the invention. Exemplary accessory polypeptide include, ligases, transferases, dehydrogenases, and the like. Although both shuffled and non-shuffled polypeptides can be used, preferred accessory polypeptides are those that have been shuffled.

The non-monooxygenase polypeptides can be used at any step of a pathway of the invention. In a preferred embodiment, they will be used to further transform the oxidation product. Although it will generally be preferred to utilize oxidized substrates that are produced by a monooxygenase of the invention, those of skill will appreciate that these routes can be practiced with analogous substrates that are, for example chemically synthesized, commercially available, etc.

Moreover, the present invention provides methods using both the improved accessory peptides and unimproved accessory peptides to further elaborate the monooxygenase-mediated reaction product. The method includes contacting the product of the monooxygenase-mediated reaction with one or more of the accessory polypeptides. In a preferred embodiment, the product is contacted with an organism that expresses the accessory polypeptide(s). When the accessory polypeptides are improved polypeptides, they will generally be produced by the methods described herein.

The improved monooxygenase and the accessory polypeptide(s) can be expressed by the same host cell, or they can be expressed by different host cells. In a preferred embodiment, the accessory polypeptide is an improved polypeptide.

By utilizing accessory polypeptides, the present invention makes possible the synthesis of a great variety of industrially valuable compounds via the methods disclosed herein.

1. Dehydrogenases

In a preferred embodiment, an alcohol or diol is converted to an aldehyde or carboxylic acid by the action of a dehydrogenase. The substrate for the dehydrogenase is preferably the product of an improved oxygenase of the invention.

Polynucleotides encoding many known dehydrogenases can be used as substrates for DNA shuffling. Exemplary dehydrogenases useful in practicing the present invention include, but are not limited to:

[ECOALDB, ECAE000436, ECAE000239, D90780, D90781, ECOFUCO, ECOFUCO] dehydrogenase of *Escherichia coli;* [AF029734 and AF029733] dehydrogenase of *Xanthobacter autotrophicus;* [AREXOYGEN] dehydrogenase of *Agrobacterium radiobacter;* [AB003475] dehydrogenase of *Deinococcus radiodurans;* [AF034434, VIBTAGALDA] dehydrogenase of *Vibrio cholerae;* [D32049] dehydrogenase of *Synechococcus* sp.; [AE001154] dehydrogenase of *Borrelia burgdorferi* (BB0528); [ABY17825] dehydrogenase of *Agaricus bisporus;* [ASNALDAA] dehydrogenase of *Aspergillus niger;* [EMEALDA, EMEALCA] dehydrogenase of *Aspergillus nidulans;* [AF019635, PPU15151] dehydrogenase of *Pseudomonas putida* TOL plasmid, xylW, xyl C; [AF031161] dehydrogenase of Pseudomonas sp. VLB120, (stdD); [PFSTYABCD] dehydrogenase of *P. fluorescens*, styD; [PPU24215] dehydrogenase of *P. putida*, Flp-cymene alcohol and aldehyde dehydrogenases.

2. Conversion of hydroxyls and/or acids to esters

In another preferred embodiment, there is provided a method for converting carboxylic acid and hydroxyl groups to adducts such as esters and ethers. Useful polypeptides include, for example, ligases and transferases (see, FIG. 4). For the purposes of the discussion below, these polypeptides are referred to as "adduct-forming" polypeptides.

The adduct-forming polypeptides are useful for enhancing and controlling the production of biotransformation products. These polypeptides, which convert a diol, for example, to a monoacyl or monoglycosyl derivative can enhance control over the regioselectivity of subsequent reactions (e.g., chemical dehydration). For example, the regioselectivity of chemical dehydration in certain cases can be controlled by converting the compounds to their diacyl derivatives by means of chemical reaction, and then selectively removing one of the acyl groups using an polypeptide of the invention. Alternatively, one can control the regioselectivity of the dehydration by using an esterase or a trans-acylase polypeptide to convert the compounds to monoacyl derivatives, preferably in the presence of an excess of another carboxylic acid ester. In addition, the isolation of certain products is simplified by their conversion to more hydrophobic species. For example, the acylation of a diols to the corresponding carboxylic ester provides for a more efficient recovery of such diols, in the form of an ester, by organic solvent extraction of the adduct, Preferred organic solvents are those that can be used in an immiscible biphasic organic-aqueous biotransformation with whole cells, whether in a batch or in a continuous mode.

An adduct-forming polypeptide can be expressed by the same host cell that expresses the dioxygenase, dehydrogenase, racemase, etc., or it can be expressed by a different host cell. Moreover, an adduct-forming polypeptide can be a naturally occurring polypeptide, or it can be improved by the method of the invention.

When the adduct-forming polypeptide is an improved polypeptide, in presently preferred embodiments, the polypeptides demonstrates increased efficiency in the formation of the monoacyl- or monoglycosyl-derivatives of a desired compound (e.g., a glycol, carboxylic acid, etc.). Other improved adduct-forming polypeptides include transferases and ligases that can selectively modify only one of the hydroxyl groups of a diol, thus providing a means for controlling the regioselectivity of dehydration of such derivatives to either of two possible isomeric α-hydroxycarboxylic acid compounds.

a. Acyltransferases

One class of enzymes useful in practicing the present invention are the acyltransferases. These polypeptides can be evolved to enhance certain catalytic properties of the encoded polypeptides such as, specificity for a particular hydroxyl and/or acid, enantiomeric and/or diastereomeric selectivity.

Figure 4:
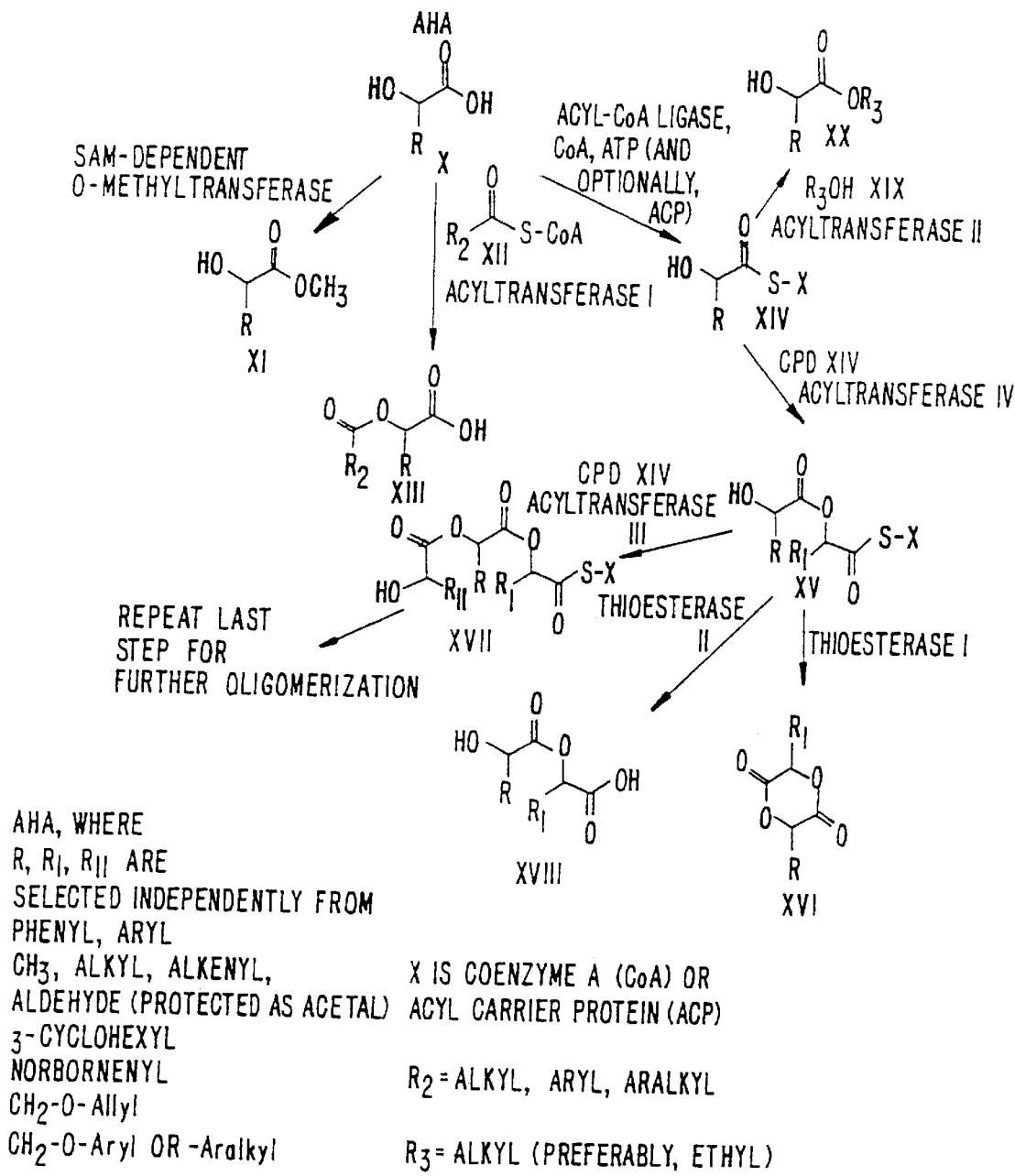
FIG. 4. Enzymatic reaction schemes for converting free AHAs to ester derivatives.
Figure 5A:
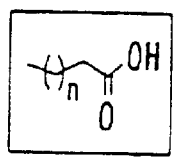
FIG. 5A exemplifies preferred reactions by a shuffled MO on fatty acid substrates and n-alkanes.
Figure 5A:
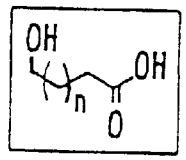
Figure 5A:
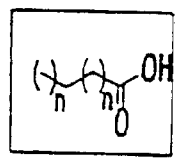
Figure 5A:
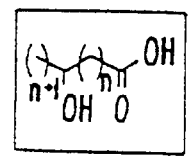
Figure 5A:
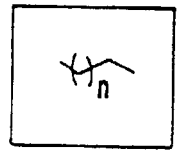
Figure 5A:
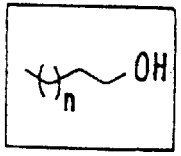
Figure 5A:
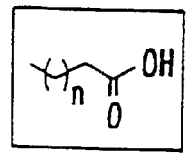
Figure 5A:
Figure 5A:
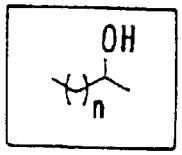
Figure 5A:
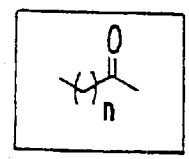
Figure 5B:
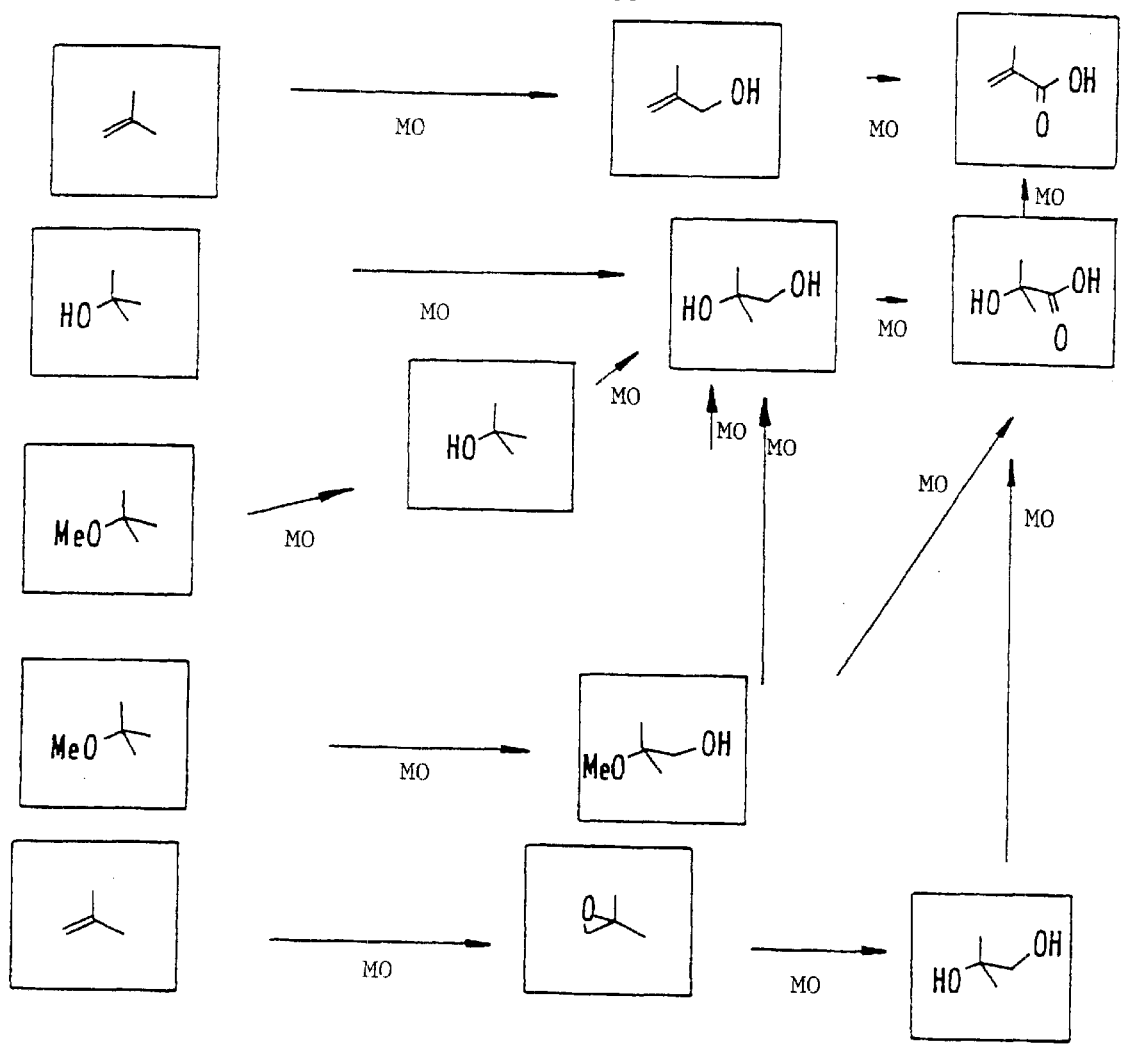
FIG. 5B exemplifies preferred reactions by a shuffled MO on branched chain alkenes and carbon backbones.
Figure 5C:
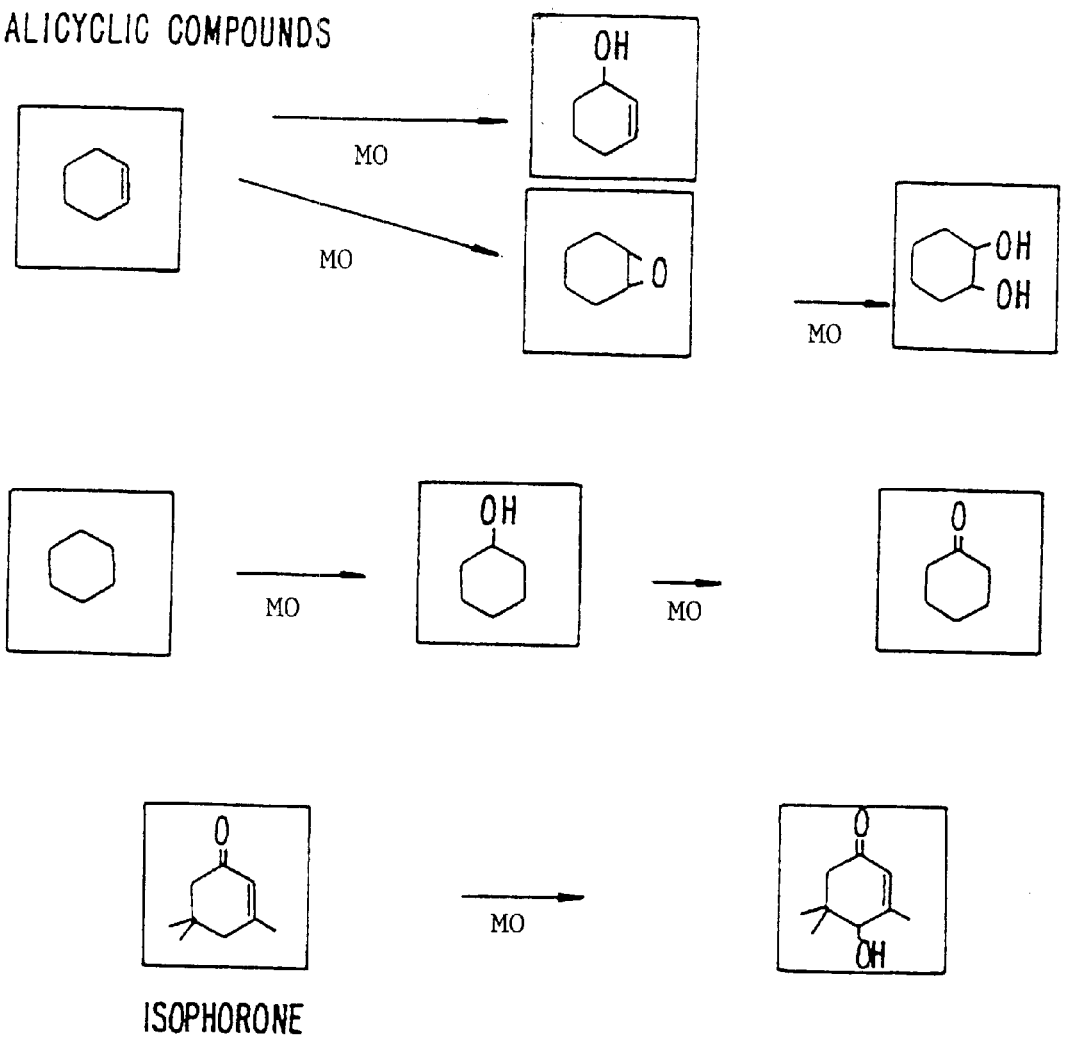
FIG. 5C exemplifies preferred reactions by a shuffled MO on alicyclic compounds.
Figure 5D:
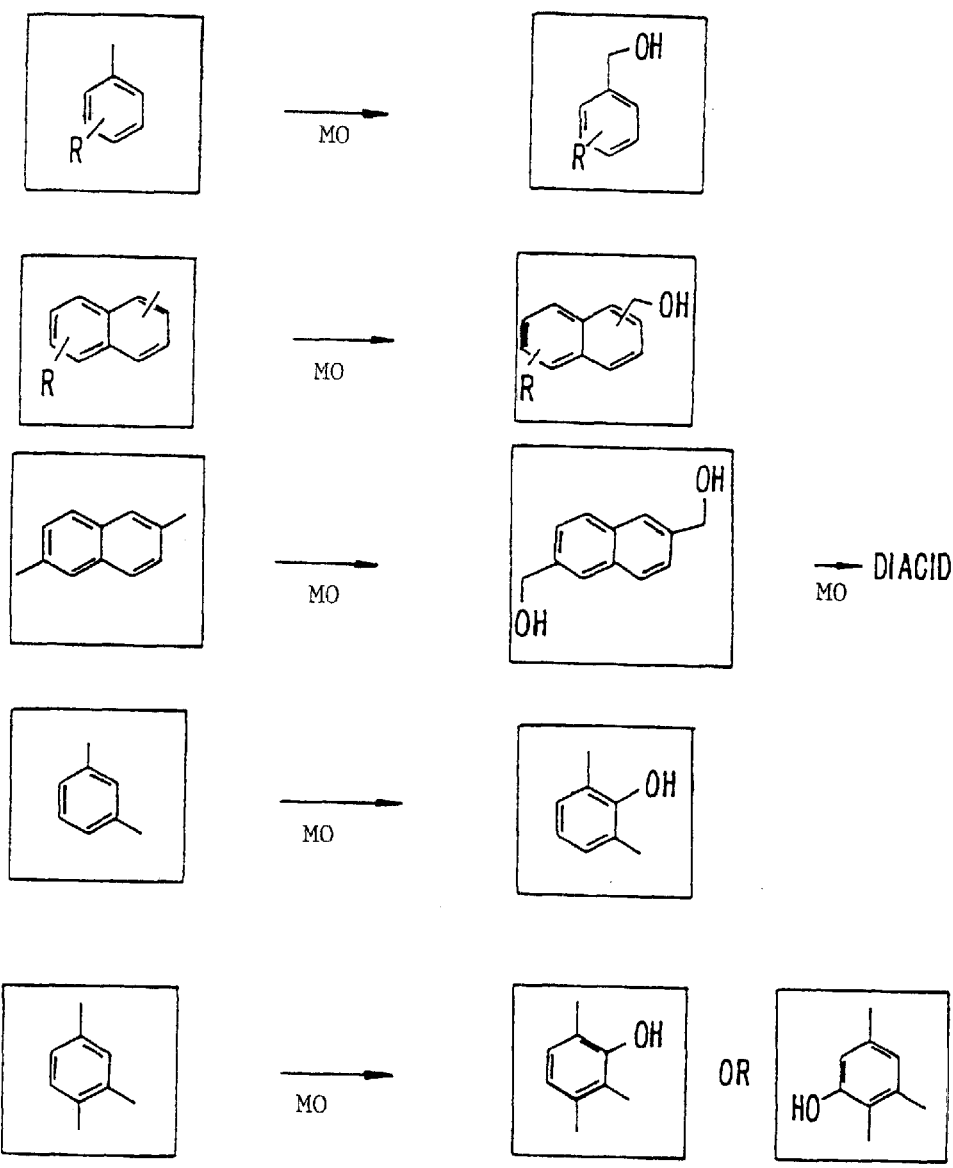
FIG. 5D exemplifies preferred reactions by a shuffled MO on aromatic compounds.
Figure 5E:
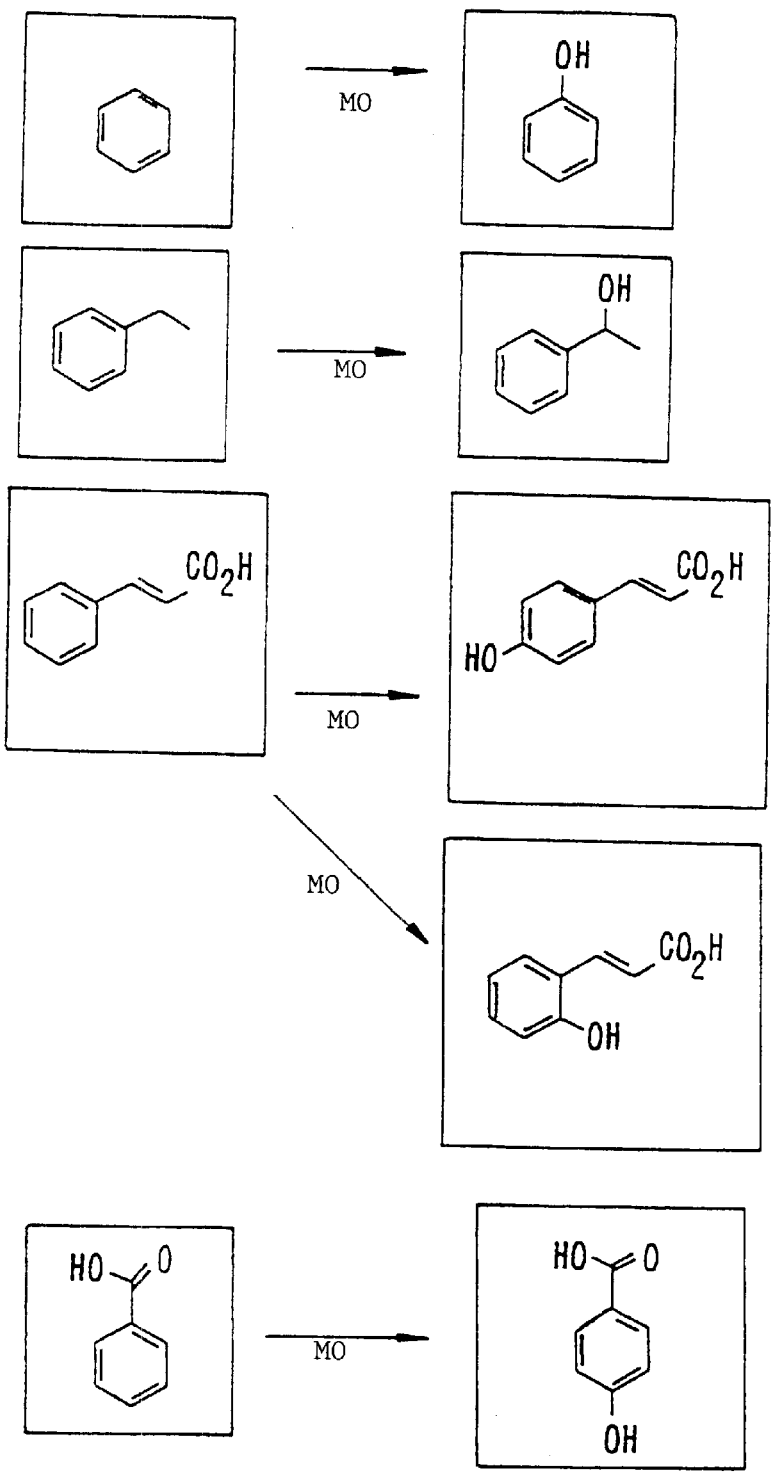
FIG. 5E exemplifies preferred reactions by a shuffled MO on aromatic compounds.
Figure 5F:
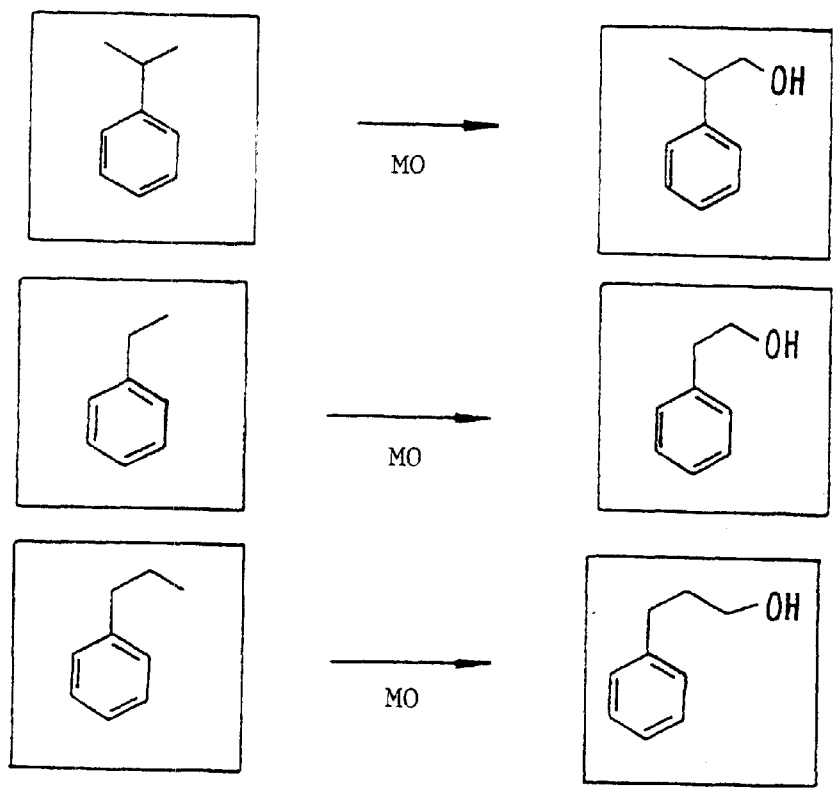
FIG. 5F exemplifies preferred reactions by a shuffled MO on aromatic compounds.
Figure 5G:
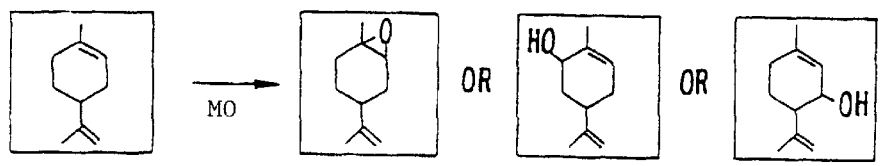
FIG. 5G exemplifies preferred reactions by a shuffled MO on terpenoids and linear olefins.
Figure 5G:
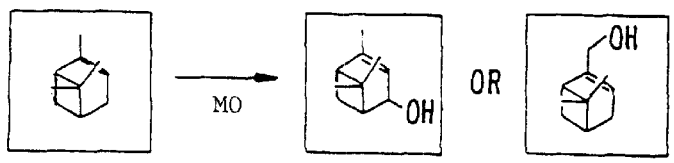
Figure 5G:
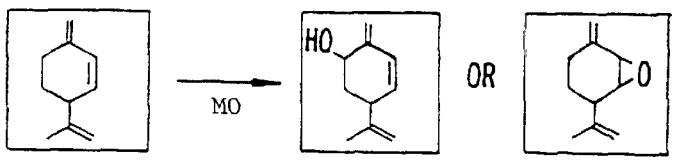
Figure 5G:
Figure 5G:
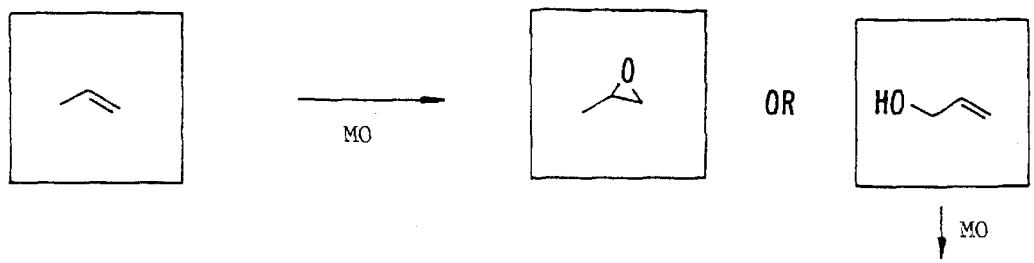
Figure 5G:
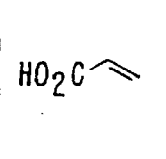

More specifically, these polypeptides catalyze acyl transfer reactions as shown in FIG. 4. Acyltransferases are ubiquitous in nature, and many organisms (e.g., microbes, plants, mammals, etc.) can be used as sources of genes encoding these polypeptides. No matter their origin, the acyltransferase genes are preferably selected from those encoding functional polypeptides that catalyze active (CoA) ester transfer reactions in the biocatalytic processes described herein. Preferred acyltransferase genes are selected from those encoding functional polypeptides catalyzing reactions of small non-biopolymeric molecules.

Examples of various acyltransferases useful in the present invention include polypeptides that catalyze the methylation of α-hydroxycarboxylic acids. A list of exemplary polynucleotides that can be recruited for this purpose are listed below by the corresponding GenBank identification:

[AF043464] acetyl-CoA: benzylalcohol acetyltransferase of *Clarkia breweri*, and benzoyl-CoA benzyl alcohol acetyltransferase present in the same organism, (Dudareva et al, *Plant Physiol.* 116(2):599–604 (1998)); [DCANTHRAN, DCHCBT1, DCHCBTIA, DCHCBT1B, DCHCBT2, DCHCBT3] hydroxycinnamoyl/benzoyl-CoA:anthranilate N-acyltransferase of *Dianthus caryophyllus*; [E08840] homoserine o-acetyltransferase of *Acremonium chrysogenum*; [E12754] anthocyanin 5-aromatic acyltransferase, of *Gentiana triflora*; [HUMBCAT] branched chain acyltransferase (human, J03208, J04723); [MG396;D02 °orf152(lacA); MJ1064(lacA) MJ1678, MTH1067]; galactoside 6-O acetyl transferase EC 2.3.1.18, lac A of *E. coli*; B0342(lacA); or of other organisms; [B3607(cysE), HI0606(cysE), HP1210(cysE), SLR1348(cysE)] serine O-acetyltransferase EC 2.3.1.30; [YGR177C, YOR377W] alcohol O-acetyltransferase, EC 2.3.1.84, of *Saccharomyces cerevisiae*; [e.g., Q00267,D90786, Z92774,I78931 AF030398, AF008204, AF042740] arylamine N-acetyltransferase, EC 2.3.1.118; [YAR035 (YAT1), YM8054.01(CAT2)] carnitine O-acetyltransferase, EC 2.3.1.7, or mammalian origin of from yeast; [CHAT] choline O-acetyltransferase, EC 2.3.1.6, of mammalian origin; acetyl CoA:deacetylvindoline 4-O-acetyltransferase (EC 2.3.1.107) St-Pierre et al, *Plant J.* 14(6): 703–713 (1998); and [ECOPLSC] 1-acyl-sn-glycerol-3-phosphate acyltransferase (plsC) of *Escherichia coli*.

b. Acyl CoA ligases

In another embodiment an accessory polypeptide having acyl CoA ligase activity is provided.

The specificity of acyl-CoA ligases towards a particular exogenous substrate or a group of substrates is preferably optimized by screening or selecting for the acylation of a substrate by shuffled and co-expressed acyl-CoA ligases and acyltransferases. Utilizing these polypeptides in tandem allows the combined effect of both polypeptides to be exploited.

To illustrate the family or single gene shuffling approach to improving acyl-CoA ligases or acyltransferases, one more of the more members of the corresponding superfamilies of these polypeptides are selected, aligned with similar homologous sequences, and shuffled against these homologous sequences.

An exemplary list of useful acyl-CoA ligase genes for inclusion into an organism of the invention is provided below:

[AF029714, ECPAA, AJO00330, PSSTYCATA] phenylacetate-CoA ligase, EC 6.2.1.30; [Y11070, Y11071] phenylpropionate-CoA ligase; [B2260 (menE), SLR0492(menE), SAU51132(menE)] O-succinylbenzoate-CoA ligase, EC 6.2.1.26; [RPU75363, RBLBADA, AA532705, AA664442, AA497001, AF042490, ARGFCBABC] (chloro) benzoate-CoA ligase, EC 6.2.1.25; [SBU23787, VPRNACOAL, POTST4C11, RIC4CL2R, OS4CL, AF041051, AF041052, GM4CL14, GM4CL16, LEP4CCOALA, LEP4CCOALB, PC4CL1A, PC4CL1AA, PC4CL2A, PC4CL2AA, TOB4CCAL, TOBTCL2, TOBTCL6, ECO110K, AF008183, AF008184, AF041049, AF041050, ATU18675, NTU5084, NTU50846, PTU12013, PTU39404, PTU39405, ATF13C5, ORU61383, AF064095, AA660600, AA660679, STMPABA] 4-coumarate-CoA ligase EC 6.2.1.12; [RPU02033] 4-hydroxybenzoate-CoA ligase; [PSPPLAS] 2-aminobenzoate-CoA ligase.

In some embodiments of the invention, a carboxylic acid is fed exogenously to the organism that expresses the ligase or transferase. Preferably, the carboxylic acid is selected from those compounds that cannot be altered by the polypeptide used to produce the substrate acted upon by the adduct forming polypeptide. Such carboxylic acids include, for example, both substituted and non-substituted benzoic acid, phenylacetic acid, naphthoic, phenylpropionic acid, phenoxyacetic acid, cycloalkanoic acid, carboxylic acids derived from terpenes, pivalic acid, substituted acrylic acids, and the like.

To facilitate the utilization of exogenously supplied carboxylic acids, and for enhancing the variety of compounds suitable for use in this process, the invention also provides microorganisms in which one or more mutations are introduced. Preferred mutations are those that effectively block metabolic modifications of such acids beyond their conversion to a suitable active ester (e.g., as a derivative of coenzyme A). Such mutations in the host organism can be introduced by classical mutagenesis methods, by site-directed mutagenesis, by whole genome shuffling, and other methods known to those of skill in the art. One can also introduce mutations that minimize host endogenous esterase activity.

In a presently preferred embodiment, the acyl transferase-encoding nucleic acids used as substrates for creating recombinant libraries encode polypeptides that transfer an acetyl group from an endogenous pool of acetyl-CoA in the cells of the host. The endogenous pools of acetyl-CoA can also be enhanced by DNA shuffling of an acetyl-CoA ligase and by supplying an exogenous acetate in the medium.

While using acetyl-CoA transferases or other acyltransferase or glycosyltransferase does not necessarily require expression of a corresponding acetyl-CoA or other ligase, in a presently preferred embodiment, the organisms produce a sufficient amount of an acyl-CoA ligase so as to activate the carboxylic acids to CoA thioesters, which in turn serve as substrates for acyl-CoA transferases that utilize the oxidation products as substrates. The specificity of an acyl-CoA ligase towards a desired exogenous carboxylic acid can be optimized using the recombination and screening/selection methods of the invention. Preferably, the screening or selecting is performed using co-expressed acyl-CoA ligases and acyltransferases, thus permitting one to screen on the basis of the combined effect of both polypeptides in the pathway for provision of monoacylated derivatives of the oxidation products.

Nucleic acids that encode acyl-CoA ligases and other acyltransferases useful as substrates for the recombination and selection/screening methods of the invention include, for example, one or more members of the superfamilies of these polypeptides. In a presently preferred embodiment, the nucleic acids are selected, aligned with similar homologous sequences, and shuffled against these homologous sequences.

c. Glycosyltransferases

Similarly, one or more glycosyltransferases can be expressed by the host cells of the invention. Alternatively, one or more glycosyltransferases can be selected from the glycosyltransferase superfamily, aligned with similar homologous sequences, and shuffled against these homologous sequences. Glycosyl transfer reactions are ubiquitous in nature, and one of skill in the art can isolate such genes from a variety of organisms, using one or more of several art-recognized methods. The following are illustrative examples of glycosyltransferase-encoding nucleic acids that can be used as substrates for creation of the recombinant libraries. The libraries are then screened to identify those polypeptides that exhibit an improvement in the glycosylation of compounds such as alcohols, diols and α-hydroxycarboxylic acids:

[EC 2.4.1.123] inositol 1-α-galactosyltransferase; [NTU32643, NTU32644] phenol β-glucosyltransferase, EC 2.4.1.35; flavone 7-O-beta-glucosyltransferase, EC 2.4.1.81; [AB002818, ZMMCCBZ1, AF000372, AF028237, AF078079, D85186, ZMMC2BZ1, VVUFGT]; flavonol 3-O-glucosyltransferase, EC 2.4.1.91; o-dihydroxycoumarin 7-O-glucosyltransferase, EC 2.4.1.104; vitexin beta-glucosyltransferase, EC 2.4.1.105; coniferyl-alcohol glucosyltransferase, EC 2.4.1.111; monoterpenol beta-glucosyltransferase, EC 2.4.1.127; arylamine glucosyltransferase, EC 2.4.1.71; sn-glycerol-3-phosphate 1-galactosyltransferase, EC 2.4.1.96; [RNUDPGTR, AA912188, AA932333] glucuronosyltransferase, EC 2.4.1.17; the human UGT and isoenzymes (~35 genes); salicyl-alcohol glucosyltransferase, EC 2.4.1.172; 4-hydroxybenzoate 4-O-beta-D-glucosyltransferase, EC 2.4.1.194; zeatin O-beta-D-glucosyltransferase, EC 2.4.1.203; [VFAUDPGFTA] D-fructose-2-glucosyltransferase; and [MBU41999] ecdysteroid UDP-glucosyltransferase (egt).

In presently preferred embodiments, the glycosyltransferases are selected from those which transfer hexose residues from UDP-hexose derivatives. Preferred hexoses include, for example, D-glucose, D-galactose and D-N-acetylglucosamine.

d. Methyltransferases

In a still further preferred embodiment, the host cells of the present invention express a polypeptide capable of converting a carboxylic acid to a carboxylic acid methyl ester. Presently preferred polypeptides include methyltransferases.

For the purpose of this invention, genes encoding S-adenosylmethionine-dependent methyltransferases are preferred. In a preferred embodiment, these polypeptides are evolved to enhance selected properties of the encoded polypeptides such as, specificity for a particular substrate and enantiomeric and/or diastereomeric selectivity and/or solvent resistance.

More specifically, these polypeptides can be evolved to catalyze the O-methylation of carboxyl groups of a caroxylic acid substrate thus forming the corresponding methyl esters. Methyltransferases are ubiquitous in nature, and many organisms (e.g., microbes, plants, mammals, etc.) can be used as sources of genes encoding these polypeptides. No matter their origin, the methyltransferase genes are preferably selected from those which encode functional polypeptides that catalyze the methylation of small non-biopolymeric molecules. Preferably, the methyltransferases are those which act on the carboxyl groups of organic acids.

Examples of various methyltransferases that can be expressed by host cells of the invention and which are useful for DNA shuffling-based directed evolution of polypeptides catalyzing the methylation of carboxylic acids are listed below by the corresponding GenBank identification:

[SCCCAGC3] methyltransferase of *Streptomyces clavuligerus* methyltransferase CmcJ; [SEERYGENE] methyltransferase of *S. erythraea* methyltransferases; [SEU77454] methyltransferase of *Saccharopolyspora erythraea*; erythromycin O-methyltransferase (eryG); [SGY08763] methyltransferase of *S. griseus*; [SKZ86111] methyltransferase of *S. lividans*; [STMDNRDKP] methyltransferase of *Streptomyces peucetius*; carminomycin o-methyltransferase (dnrK); [MDAJ39670] methyltransferase of *Streptomyces ambofaciens*; [SEY 14332] methyltransferase of *Saccharopolyspora erythraea*; [SPU10405] methyltransferase of *Streptomyces purpurascens* ATCC 25489; [STMDAUA] methyltransferase of Streptomyces sp.; aklanonic acid methyltransferase (dauC), and carminomycin 4-O-methyltransferase (dauK); [SC2A11 and SC3F7] methyltransferase of *Streptomyces coelicolor*; [SHGCPIR] methyltransferase of *S. hygroscopicus*; [STMCARMETH] methyltransferase of *Streptomyces peucetius* carminomycin 4-O-methyltransferase; [STMODPOMT] methyltransferase of *Streptomyces alboniger* O-demethylpuromycin-O-methyltransferase (dmpM); [STMTCREP]; methyltransferase of *Streptomyces glaucescens*; [SLLMRBG] methyltransferase of *S. lincolnensis* lmrB methyltransferase; [SSU65940] 31-O-demethyl-FK506 methyltransferase (fkbM) of Streptomyces sp.; [STMDAUABCE] aklanonic acid methyltransferase (dauC) of Streptomyces sp.; [STMMDMBC] O-methyltransferase (mdmC) of *Streptomyces mycarofaciens*; [STMTYLF] macrocyn-O-methyltransferase (tylF) of *S. fradiae*; [E08176] Gene of mycinamicin III-O-methyltransferase; [AF040571] methyltransferase of *Amycolatopsis mediterranei*; [ECU56082] S-adenosylmethionine:2-demethylmenaquinone methyltransferase (menG) of *Escherichia coli*; [RHANODABC] methyltransferase (nodS) of *Azorhizobium caulinodans*; [YSCSTE14] isoprenylcysteine carboxyl methyltransferase (STE14) of *Saccharomyces cerevisiae*; [YSCMTSW] farnesyl cysteinecarboxyl-methyltransferase (STE 14) of *Saccharomyces cerevisiae*; [YSCDHHBMET] 3,4-dihydroxy-5-hexaprenylbenzoate methyltransferase (COQ3) of *S. cerevisiae*; [AF004112 and AF004113] phospholipid methyltransferases (cho1+), (cho2+) of *Schizosaccharomyces pombe*; [ASNOMT, ASNOMT1A, ASNOMT1B, ASNOMT1C and AF036808-AF036830] O-methyltransferases of Aspergillus; [MSU20736] S-adenosyl-L-methionine; trans-caffeoyl-CoA3-O-methyltransferase of *Medicago sativa*; [ALFIOM] isoliquiritigenin 2'-O-methyltransferase of *Medicago sativa*; [MSU20736] S-adenosyl-L-methionine; trans-caffeoyl-CoA3-O-methyltransferase (CCOMT) of *Medicago sativa*; [MSAF000975] 7-O-methyltransferase (7-IOMT(6)) of *Medicago sativa*; [MSAF000976] 7-O-methyltransferase (7-IOMT(9)) of *Medicago sativa*; [MSU97125] of isoflavone-O-methytransferase *Medicago sativa*; [NTCCOAOMT] caffeoyl-CoA 0-methyltransferase of *Nicotiniana tabacum*; [NTZ82982] caffeoyl-CoA O-methyltransferase 5 of *N. tabacum*; [NTDIMET] o-diphenol-O-methyltransferase of *N. tabacum*; [PCCCOAMTR, PUMCCOAMT] trans-caffeoyl-CoA 3-O-methyltransferase of *Petroselinum crispum*; [PTOMT1] s caffeic acid/5-hydroxyferulic acid O-methyltransferase (PTOMT1) of *Populus tremuloide*; [PBTAJ4894-PBTAJ4896] caffeoyl-CoA 3-O-methyltransferases of *Populus balsamifera* subsp. trichocarpa; [ZEU 19911] S-adenosyl-L-methionine: caffeic acid 3-O-methyltransferase of *Zinnia elegans*; [SLASADEN] S-adenosyl-L-methionine:trans-caffeoyl-CoA 3-O-methyltransferase of *Stellaria longipes*; [VVCCOAOMT] caffeoyl-CoA O-methyltransferase of *V. vinifera*; [D88742] O-methyltransferase of *Glycyrrhiza echinata*; [AF046122] caffeoyl-CoA 3-O-methyltransferase (CCOMT) of *Eucalyptus globulus*; [ATCOQ3] dihydroxypolyprenylbenzoate: methyltransferase of *Arabidopsis thaliana* [CSJSALMS9O] S-adenosyl-L-methionine:scoulerine 9-O-methyltransferase of *Coptis japonica*; [HVU54767] caffeic acid O-methyltransferase (HvCOMT) of *Hordeum vulgare*; [MCU63634] inositol methyltransferase (Imt1) of *Mesembryanthemum crystallinum*; [PSU69554] 6a-hydroxymaackiain methyltransferase (hmm6) of *Pisum sativum*; [CAU83789] O-diphenol-O-methyltransferase of *Capsicum annuum*; [U16794] 3' flavonoid O-methyltransferase (fomt1) of *Chrysosplenium americanum*; [CBU86760] SAM:(Iso)eugenol O-methyltransferase(IEMT1) of *Clarkia breweri*; salicylic acid carboxyl SAM-O-methyltransferase (Dudareva et al, *Plant Physiol.* 116(2):599–604 (1998)); [HSHIOMT9] hydroxyindole-O-methyltransferase (HIOMT) of *Homo sapiens*; [HSCOMT2] gene catechol O-methyltransferase of *Homo sapiens*; [HUMPNMTA] phenylethanolamine N-methyltransferase gene of *Homo sapiens*; [HUMCOMTA] catechol-O-methyltransferase of *Homo sapiens*; [HUMCOMTC] catechol-O-methyltransferase of *Homo sapiens*; [HUMPNMT] phenylethanolamine N-methyltransferase of *Homo sapiens*; [AF064084] prenylcysteine carboxyl methyltransferase (PCCMT) of *Homo sapiens*; [HUMCMT] carboxyl methyltransferase of *Homo sapiens*; [HUMHNMA] histamine N-methyltransferase of *Homo sapiens*; [RATCATAA, RATCATAB] catechol-O-methyltransferase of *R. norvegicus*; [RATDHNPBMT] dihydroxypolyprenylbenzoate methyltransferase of *Rattus norvegicus*; [BOVPNMTB] of Bovine phenylethanolamine N-methyltransferase; [MPEMT7] phosphatidylethanolamine-N-methyltransferase of *Mus musculus* 2; [MMU86108] nicotinamide N-methyltransferase (NNMT) of *Mus musculus*; [MUSCMT] carboxyl methyltransferasease protein of Mouse; [GDHOMT] hydroxyindole-O-methyltransferase of *G. domesticus*; [DRU37434] L-isoaspartate (D-aspartate) O-methyltransferase (PCMT) of *Danio rerio*; [DMU37432] protein D-aspartyl, L-isoaspartylmethyltransferase of *Drosophila melanogaster*; and [HAU25845 and HAU25846] farnesoic acid o-methyl-transferases of *Homarus americanus*.

3. Epoxide hydrolases

In a still further preferred embodiment, the present invention provides a nucleic acid encoding a polypeptide capable of converting a particular epoxide to the corresponding diol.

Presently preferred polypeptides include epoxide hydrolases. Many epoxide hydrolases are known, and these enzymes have various substrate specificity and enantioselectivity. Examples of prokaryotic genes encoding epoxide hydrolases suitable for effecting epoxide hydrolysis relevant to this invention include, but are not limited to, [CAJ4332] *Corynebacterium* sp.; and [ARECHA] *Agrobacterium radiobacter* (echA).

Figure 3:
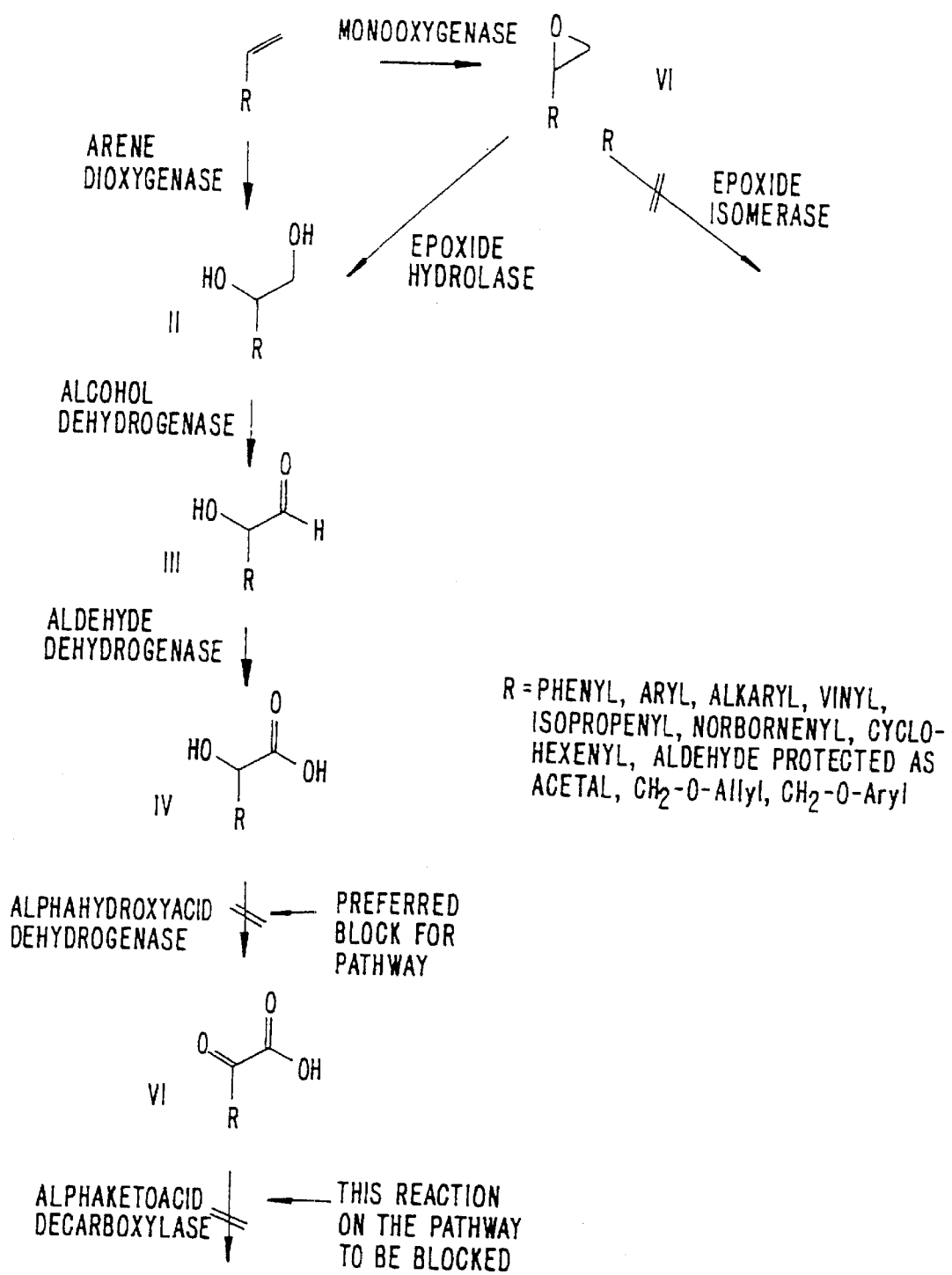
FIG. 3. Enzymatic reaction schemes for multistep biochemical transformations of olefins to AHAs.

In a presently preferred embodiment, the polypeptide has one or more improved properties brought about by shuffling methods described herein. Thus, the nucleic acids encoding this gene, and any homologs of thereof, are subjected to DNA shuffling to evolve polypeptides having improved or optimal performance and specificity towards particular substrates such as α-hydroxycarboxylic acids. In a preferred embodiment, the polypeptide has a performance and/or specificity that is enhanced over the wild type. Preferred polypeptides act on α-hydroxycarboxylic acid substrates, such as those displayed in FIG. 3.

4. Enantiomeric interconversion.

In a still further preferred embodiment, the present invention provides a nucleic acid encoding a polypeptide capable of converting a particular enantiomer of a chiral compound such as an alcohol, diol or α-hydroxycarboxylic acid or a precursor or analogue thereof to its antipode.

Presently preferred polypeptides include racemases, such as the mandelate racemase of *Pseudomonas putida* (PSEMDLABC). These polypeptides can expressed by hosts of the invention in their natural form or, alternatively, they can be evolved to enhance certain catalytic properties of the encoded polypeptides such as, specificity for a particular substrate and enantiomeric and/or diastereomeric selectivity.

The nucleic acids encoding the mandelate racemase of *Pseudomonas putida*, which catalyzes the interconversion of mandelate R and S enantiomers, is a typical preferred example of genes selected for use in this invention. The nucleic acids encoding this gene, and any homologs of thereof, are subjected to DNA shuffling to evolve polypeptides having improved or optimal performance and specificity towards particular substrates such as α-hydroxycarboxylic acids. In a preferred embodiment, the polypeptide has a performance and/or specificity that is enhanced over the wild type. Preferred polypeptides act on α-hydroxycarboxylic acid substrates, such as those displayed in FIG. 3.

5. α-Ketocarboxylic acid decarboxylase

Several thiamine phosphate-dependent polypeptides of this class are known to occur in bacteria, fungi and yeast (see, Iding et al., Biochim. Biophys. Acta 1358:307–22 (1998)). For the purpose of illustration, a gene encoding a well-known decarboxylase, preferably a benzoylformate decarboxylase (mdlC) of *Pseudomonas putida* [PSEMDLABC], is shuffled to increase the specific activity towards α-ketocarboxylic acids, such as o-hydroxybenzalpyruvate. Alternatively, genes encoding pyruvate decarboxylases (EC 4.1.1.1), indole-3-pyruvate decarboxylases (EC 4.1.1.74) or phenylpyruvate decarboxylases (EC 4.1.1.43) from a variety of sources can be used.

6. Solvent resistance polypeptides

The invention also provides organisms expressing one or more of the improved polypeptides of the invention and that are also resistant to solvents, organic substrates and reaction products (e.g., epoxides, glycols, α-hydroxyaldehydes, α-hydroxycarboxylic acids and α-hydroxycarboxylic acid derivatives (e.g., esters)) according to the methods of the invention.

The solvent resistance of organisms and polypeptide used in the biocatalytic conversion of organic compounds is important for enhancing the productivity of such processes. Increased solvent resistance of the organisms can enhance longevity, viability and catalytic activity of the microbial cells, and can simplify the administration of the feedstock compounds to the reactor and the recovery or separation of desired products by means of, for example, continuous or semi-continuous liquid-liquid extraction.

In another aspect, the invention provides microbial cells that are useful in the synthetic methods described herein, which express proteins conferring resistance to solvents (in particular, organic solvents) upon the microbial cells. This allows the use of whole microbial cells in a organic-aqueous mixture (e.g., a biphasic mixture). In presently preferred embodiments, the invention provides microbial strains including at least two of the polypeptide systems described herein. For example, a microorganism of the invention can contain both a dioxygenase gene and a transferase gene. In other embodiments, the microorganism can contain both an arene dioxygenase gene and a solvent resistance gene. The microbial cells thus provide a significant improvement in productivity of the synthesis processes, selectivity of product formation, operational simplicity, ease of product recovery and minimizing any by-product streams.

Several microorganisms are known to possess high resistance to hydrophobic compounds such as benzene and lower alkylbenzenes. Recently, genes encoding a solvent efflux pump (srpABC) have been identified in *Pseudomonas putida* strains (Kieboom et al. *J. Biol. Chem.* 273:85–91 (1998)). Similarly, various genes that encode polypeptides that confer organic solvent resistance can be found in bacterial strains such as *Pseudomonas putida* GM73 (Kim et al. *J. Bacteriol.* 180: 3692–3696 (1998)), *Pseudomonas putida* DOT-T1E (Ramos et al. *J. Bacteriol.* 180: 3323–3329 (1998)), *Pseudomonas idaho* (Pinkart and White *J. Bacteriol.* 179: 4219–4226 (1997)). These and other genes, such as those that encode many proton-dependent multidrug efflux systems, e.g., MexA-MexB-OprM, MexC-MexD-OprJ, and MexE-MexF-OprN of *Pseudomonas aeruginosa* (Li et al. *J. Bacteriol.* 180: 2987–2991 (1998)), or the tolC, acrAB, marA, soxS, and robA loci of *Escherichia coli* (Aono et al., *J. Bacteriol.* 180:938–944 (1998); White et al., *J. Bacteriol.* 179:6122–6126 (1997)), and in many other microorganisms, can be used to confer solvent resistance upon a host microbial strain used in the oxidative biocatalytic conversion of olefins by means of action of dioxygenases or dioxygenases.

In presently preferred embodiments, the ability of a polypeptide to confer solvent resistance is enhanced by subjecting nucleic acids encoding solvent resistance polypeptides, or the genomes of the microorganisms themselves, to the recombination and selection/screening methods described herein. The nucleic acids listed above, as well as similar genes, provide a source of substrates for incorporation into organisms of the invention and/or use in DNA shuffling and other methods of constructing libraries of recombinant polynucleotides. The libraries can then be screened to identify those nucleic acids that encode polypeptides conferring improved solvent tolerance on a host. For example, one can select for improved tolerance to compounds such as olefins, AHAs, aldehydes, esters and hydrophobic solvents, including alkanes, cycloalkanes, alcohols and halocarbon derivatives, for example, which are used for performing biotransformation (e.g., two-phase oxidation) of olefins to glycols, AHAs and to their corresponding acyl- and glycosyl-derivatives, etc. Similarly, DNA shuffling of nucleic acids that encode these polypeptides can be used to confer and to improve resistance of the microbial cell to high concentrations of biotransformation substrates, intermediates and endproducts, thus improving biocatalyst performance and productivity.

In addition to each of the methods set forth above, the present invention provides polypeptides produced according to these disclosed methods. Moreover, the invention provides organisms that express the polypeptides produced by the method of the invention. The organisms of the invention can express one or more of the improved polypeptides. Also provided by the present invention are methods of synthesizing a desired compound. This method includes contacting an appropriate substrate with a polypeptide of the invention. In a preferred embodiment, the substrate is contacted with an organism of the invention that expresses a polypeptide of the invention.

D. Methods of Using Improved Polypeptides to Prepare Organic Compounds

In addition to the methods discussed above, the present invention provides a range of methods for preparing useful organic compounds by the oxidation and further elaboration of appropriate precursors. Among the methods provided by the present invention are, for example, the oxidation of alkylarene compounds to the corresponding unsaturated diols and the subsequent dehydration of these diols hydroxy alkylarenes. Additionally, there is provided an analogous method for preparing hydroxylated aromatic carboxylic acids. Moreover, the invention provides methods for preparing cyclic exocyclic and/or acyclic diols from molecules having alkene bonds. The exocyclic and acyclic diols can be readily converted to α-hydroxycarboxylic acids.

The reaction types and sequences set forth below are illustrative of the scope of the invention. The monooxygenases of the invention are capable of oxidizing any organic substrate comprising an oxidizable moiety. Additional reaction sequences utilizing the polypeptides of the invention will be apparent to those of skill in the art.

1. Preparation of epoxides

In a preferred embodiment, there is provided a method for converting an olefin into an epoxide. The polypeptide of the invention is designed to be functional with substantially any olefinic substrate, however, in a preferred embodiment, the polypeptide acts on at least one alkene group of a substrate that includes:

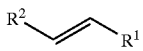

to produce an epoxide product having the structure:

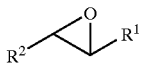

wherein, $R^1$ and $R^2$ are independently selected from H, alkyl, substituted alkyl, aryl, substituted aryl, heteroaryl, substituted heteroaryl, heterocyclyl, substituted heterocyclyl, —$NR^3R^4(R^5)_m$, —$OR^3$, —CN, $C(R^6)NR^3R^4$ and $C(R^6)OR^3$ groups. $R^3$, $R^4$ and $R^5$ are members independently selected from the group consisting of H, alkyl, substituted alkyl, aryl, substituted aryl, heteroaryl, substituted heteroaryl, heterocyclyl and substituted heterocyclyl groups. $R^5$ is selected from =O and =S. m is 0 or 1, such that when m is 1, an ammonium salt is provided.

In a still further preferred embodiment, the olefinic substrate is selected from 2-vinylpyridine, 4-vinylpyridine, 3-butenenitrile, vinylacetamide, N,N-dialkyl vinylacetamide, diallylamine, triallylamine, diallyldimethylammonium salts, styrene and phenyl-substituted styrene.

2. Preparation of vicinal diols

The formation of vicinal diols by oxidizing a π-bond using a monooxygenase of the invention and hydrolyzing the resulting epoxide provides ready access to a wide array of compounds that are useful as both final products and as intermediates in multi-step reaction pathways. The monooxygenases of the invention are capable of converting to expoxides and, thus, to vicinal diols an array of structurally distinct compounds comprising one or more π-bonds.

Although the method can be practiced with essentially any π-bond, in essentially any compound, in a preferred embodiment, the method includes preparing a vicinal diol group by contacting a substrate comprising a carbon-carbon double bond with an improved monooxygenase polypeptide, or an organism expressing an improved monooxygenase polypeptide to form an epoxide. The epoxides are cleaved by chemical or enzymatic action.

In another preferred embodiment, the substrate comprising the carbon-carbon π-bond is selected from styrene, substituted styrene, divinylbenzene, substituted divinylbenzene, isoprene, butadiene, diallyl ether, allyl phenyl ether, substituted allyl phenyl ether, allyl alkyl ether, allyl aralkyl ether, vinylcyclohexene, vinylnorbornene, and acrolein.

In yet another preferred embodiment, the vicinal diol produced by the action of the improved monooxygenase polypeptide has the structure:

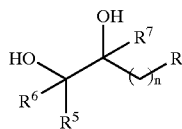

wherein $R^1$ and $R^5$ are independently selected from alkyl, substituted alkyl, aryl, substituted aryl, heteroaryl, substituted heteroaryl, heterocyclyl, substituted heterocyclyl, —$NR^2R^3$, —$OR^2$, —CN, $C(R^4)NR^2R^3$ and $C(R^4)OR^2$ groups, or $R^1$ and $R^5$ are joined to form a ring system selected from saturated hydrocarbyl rings, unsaturated hydrocarbyl rings, saturated heterocyclyl rings and unsaturated heterocyclyl rings; $R^2$ and $R^3$ are members independently selected from H, alkyl, substituted alkyl, aryl, substituted aryl, heteroaryl, substituted heteroaryl, heterocyclyl and substituted heterocyclyl groups; $R^4$ is selected from =O and =S; $R^6$ and $R^7$ are independently selected from H and alkyl; and n is a number from 0 to 10, inclusive.

In certain preferred vicinal diols $R^1$ is selected from phenyl, substituted phenyl, pyridyl, substituted pyridyl —$NR^2R^3$, —$OR^2$, —CN, $C(R^4)NR^2R^3$ and $C(R^4)OR^2$ groups, $R^2$ and $R^3$ are members independently selected from H, alkyl, substituted alkyl, aryl, substituted aryl, heteroaryl, substituted heteroaryl, heterocyclyl and substituted heterocyclyl groups; and $R^4$ is selected from =O and =S.

In another preferred embodiment, the diol includes a six-member ring having at least one endocyclic double bond and at least one substituent selected from methyl, carboxyl and combinations thereof.

3. Dehydrogenation of ROH groups

In an other preferred embodiment, the invention provides a class of improved P-450 polypeptides that dehydrogenate hydroxyl-containing substrates. Although substantially any hydroxyl-containing substrate can be dehydrogenated using the polypeptides of the invention, in a preferred embodiment, the substrate is:

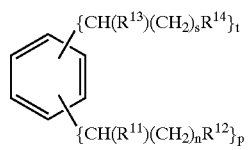

wherein $R^{11}$, $R^{12}$, $R^{13}$ and $R^{14}$ are independently selected from H and OH and at least one of $R^{11}$, $R^{12}$, $R^{13}$ and $R^{14}$ is OH; n and s are independently selected from the numbers 0 to 16; and p and t are independently selected from 0 to 6, wherein at least one of p and t must be at least one. The enzyme of the invention, preferably, converts at least one hydroxyalkyl group to a member selected from:

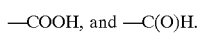

—COOH, and —C(O)H.

In another preferred embodiment, the substrate is selected from among toluene and xylene and the polypeptide converts said at least one methyl group to a carboxylic acid or a carbonyl.

4. Preparation of α-hydroxycarboxylic acids

In another preferred embodiment, there is provided a method for converting an olefin to an α-hydroxyaldehyde or an α-hydroxycarboxylic acid. In a preferred embodiment, the olefin is converted to an α-hydroxycarboxylic acid. The method includes: (a) contacting the olefin with an improved monooxygenase polypeptide of the invention to form an epoxide; (b) hydrolyzing the epoxide to form a vicinal diol; and (c) contacting the vicinal diol with a dehydrogenase polypeptide to form the α-hydroxycarboxylic acid.

As in other methods involving the hydrolysis of the expoxide, the epoxide can be hydrolyzed using chemical or enzymatic means. The hydrolysis is preferably mediated by an improved epoxide hydrolase prepared using the methods of the invention. The dehydrogenase polypeptides useful in this embodiment can be naturally occurring polypeptides or, alternatively, they can be polypeptides improved using the methods of the invention. When more than one polypeptide is used to effect a particular transformation they can be expressed in the same host organism or in different host organisms.

α-Hydroxycarboxylic acids (AHAs) are an important group of industrial chemicals. One of the simplest representatives of this class of compounds is lactic acid. Lactic acid is used for many purposes, including the synthesis of polyester polymers (e.g., polylactic acid). In addition to the lactic acid homopolymer, lactic acid can be copolymerized with other α-hydroxycarboxylic acids, such as mandelic acid, to form co-polymers with lactic acid. Enantiomerically pure hydroxycarboxylic acids are also used as resolving reagents for separating mixtures of chiral molecules. α-Hydroxycarboxylic acids are generated chemically by a variety of general methods that are less than ideal. For example, a commonly used method, hydrolysis of a cyanohydrin is problematic. The cyanohydrins are produced by the addition of HCN to an aldehyde. Aldehydes are relatively expensive starting materials and the hydrolysis of the cyanohydrins to the corresponding α-hydroxycarboxylic acids does not proceed in an enantioselective manner. This necessitates the disposal or recycling of a substantial portion of the costly aldehydes.

Chiral lactic acid has been manufactured by means of a microbial fermentative process using a carbohydrate feedstock. At present, this fermentative methodology does not provide a means for making AHAs other than lactic acid. A great number of useful AHAs have a structure wherein the lactic acid methyl group is replaced with another substituent such as, for example, aromatic, alicyclic or alkenic moieties useful for subsequent chemical modifications of either the AHAs themselves, or of polymers or copolymers incorporating these AHAs.

A promising route to the highly selective manufacture of chiral AHAs is based on the oxidation of olefins by means of a monooxygenase polypeptide of the invention. These polypeptides can be isolated and used in vitro or, alternatively, they can be used in vivo by using whole microbial cells displaying the appropriate polypeptide activity. Moreover, dioxgenase polypeptides also have useful activity. The preparation of α-hydroxy carboxylic acids utilizing dioxygenases is disclosed in U.S. Ser. No. 60/148, 850, filed on Aug. 12, 1999, now U.S.S.N. 09/637,965, filed on Aug. 11, 2000, now pending, bearing Attorney Docket No. 018097-031100, entitled "Shuffling of Dioxygenase Genes for Production of Industrial Chemicals", filed on an even date herewith and incorporated by reference in its entirety.

The present invention also provides improved polypeptides that exhibit an enhanced ability to convert a range of substrates to α-hydroxycarboxylic acids, α-hydroxycarboxylic acid precursors and analogues by processes employing oxidative biocatalysis. Methods are provided for generating polynucleotides that encode enzymes that catalyze these reactions and that have improved properties. Presently preferred substrates include olefins.

Biocatalytic methods that employ the recombinant polypeptides provided by the present invention have several significant advantages over previously available methods for the synthesis of α-hydroxy acids, their precursors and analogues. For example, the invention provides polypeptides that can increase the amount of product produced in a reaction, as well as increase the enantiomeric excess and/or regiospecific formation of the product. Among the enhanced properties that are obtained using the methods include enhanced forward rate kinetics, altered substrate specificity and affinity, enhanced regioselectivity and enantioselectivity, and decreased susceptibility to inhibitors and inactivation by substrates, intermediates and products.

As is generally true for the other aspects and embodiments of the present invention, the recombinant polypeptides of the invention are preferably expressed by an organism, such as microbial cells, that carry out the biocatalysis. Accordingly, the invention also provides organisms that are adapted for efficient biocatalytic manufacturing of α-hydroxycarboxylic acids, their analogues and their precursors. The microorganisms preferably express one or more recombinant polypeptides that are optimized for the biocatalysis pathway of interest. The biocatalytic polypeptides that are expressed by the microbial cells can be wild type or they can be recombinant polypeptides that exhibit improved properties encoded by the recombinant nucleic acids obtained using the methods of the invention. In a preferred embodiment, the organism expresses at least two enzymes selected from an improved monooxygenase, an epoxide hydrolase and a dehydrogenase. Either or both of the epoxide hydrolase and the dehydrogenase can be an improved polypeptide.

In yet another embodiment, a nucleic acid encoding a polypeptide that converts a vicinal glycol to an α-hydroxyaldehyde and/or an α-hydroxycarboxylic acid is provided. For the purpose of this invention, the genes encoding dehydrogenase polypeptides for conversion of the glycols to α-hydroxyaldehydes and/or to α-hydroxycarboxylic acids, can be selected from many known dehydrogenases.

In another preferred embodiment, the method of invention is used to convert olefinic and vicinal diol precursors to α-hydroxycarboxylic acids having the structure:

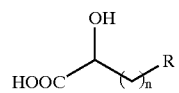

wherein,

R$^1$ is selected from aryl, substituted aryl, heteroaryl, substituted heteroaryl, heterocyclyl, substituted heterocyclyl, —NR$^2$R$^3$, —OR$^2$, —CN, C(R$^4$)NR$^2$R$^3$ and C(R$^4$)OR$^2$ groups; R$^2$ and R$^3$ are members independently selected from H, alkyl, substituted alkyl, aryl, substituted aryl, heteroaryl, substituted heteroaryl, heterocyclyl and substituted heterocyclyl groups; R$^4$ is selected from =O and =S, and n is a number between 0 and 10, inclusive.

In a still further preferred embodiment, R$^1$ is selected from phenyl, substituted phenyl, pyridyl, substituted pyridyl —NR$^2$R$^3$, —OR$^2$, —CN, C(R$^4$)NR$^2$R$^3$ and C(R$^4$)OR$^2$ groups; R$^2$ and R$^3$ are members independently selected from H, alkyl, substituted alkyl, aryl, substituted aryl, heteroaryl, substituted heteroaryl, heterocyclyl and substituted heterocyclyl groups; and R$^4$ is selected from =O and =S.

In yet another preferred embodiment, the invention provides a method for altering or controlling the regiospecificity of the dehydrogenation reaction. This method "blocks" one of the vicinal diol hydroxyl groups by forming and ester, for example. The method includes contacting the vicinal diol with a microorganism comprising an improved polypeptide having an activity selected from ligase, transferase and combinations thereof, thereby forming a α-hydroxycarboxylic acid adduct. As with the other polypeptides discussed above, this polypeptide can be expressed by the same host cell that expresses other polypeptides of the reaction cascade. Moreover, this polypeptide can be a naturally occurring polypeptide, or it can be improved using the method of the invention.

a. α-Hydroxycarboxylic acid adducts

AHAs are bifunctional molecules with two chemically and enzymatically distinguishable functional groups, carboxyl and hydroxyl. In the biocatalytic modifications of AHAs described in this invention, either of these groups can be derivatized by bond formation. While these reactions do not change the oxidation state of the AHA molecule, recruitment of the enzymes effecting modification of AHAs provides the opportunity to generate biotransformation end-products with substantially different physical and chemical properties than that of a free AHA. Generally desirable properties include an increase of hydrophobicity, a decrease of aqueous solubility and, for an ester formed through a carboxylic group of an AHA, a decrease in acidity of the process end-products.

In a preferred embodiment, the adduct-forming polypeptide produces an α-hydroxycarboxylic acid adduct selected from esters and ethers. The method includes contacting an α-hydroxycarboxylic acid with a polypeptide having an activity selected from ligase, transferase and combinations thereof, thereby forming a α-hydroxycarboxylic acid adduct. The adduct forming polypeptides useful in this embodiment can be naturally occurring polypeptides or, alternatively, they can be polypeptides improved using the methods of the invention, as discussed generally, above.

Exemplary adduct forming reactions are provided in FIG. 4. This Figure shows the use of a methyltransferase to convert carboxylic acid (X) to the corresponding methyl ester (XI), acyltransferase I to convert the X to ester XIII, and acyl-CoA ligase to convert X to intermediate XIV. This intermediate can then be transformed into a simple alkyl ester (XIX) or to structures having greater complexity of structure in the alcohol-derived component (e.g., XV). Species such as XV can be further elaborated using other polypeptides including, for example, acyltransferase III to produce compound XVII, thioesterase II to produce compound XVIII and thioesterase I to produce compound XVI.

In a further preferred embodiment, the α-hydroxycarboxylic acid adduct has the structure:

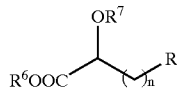

wherein, $R^1$ is selected from aryl, substituted aryl, heteroaryl, substituted heteroaryl, heterocyclyl, substituted heterocyclyl, $-NR^2R^3(R^4)_m$, $-OR^2$, $-CN$, $C(R^5)NR^2R^3$ and $C(R^5)OR^2$ groups, $R^2$, $R^3$ and $R^4$ are members independently selected from the group consisting of H, alkyl, substituted alkyl, aryl, substituted aryl, heteroaryl, substituted heteroaryl, heterocyclyl and substituted heterocyclyl groups; $R^5$ is selected from $=O$ and $=S$; $R^6$ is selected from H, alkyl and substituted alkyl groups; $R^7$ is $C(O)R^8$, wherein $R^8$ is selected from H alkyl and substituted alkyl groups and $R^7$ and $R^8$ are not both H; m is 0 or 1, such that when m is 1, an ammonium salt is provided; and n is a number between 0 and 10, inclusive.

In yet another preferred embodiment, $R^1$ is selected from phenyl, substituted phenyl, pyridyl, substituted pyridyl $-NR^2R^3$, $-OR^2$, $-CN$, $C(R^5)NR^2R^3$ and $C(R^5)OR^2$ groups; $R^2$ and $R^3$ are members independently selected from the group consisting of H, $C_1$–$C_6$ alkyl and allyl; and $R^5$ is $=O$.

Figure 2:
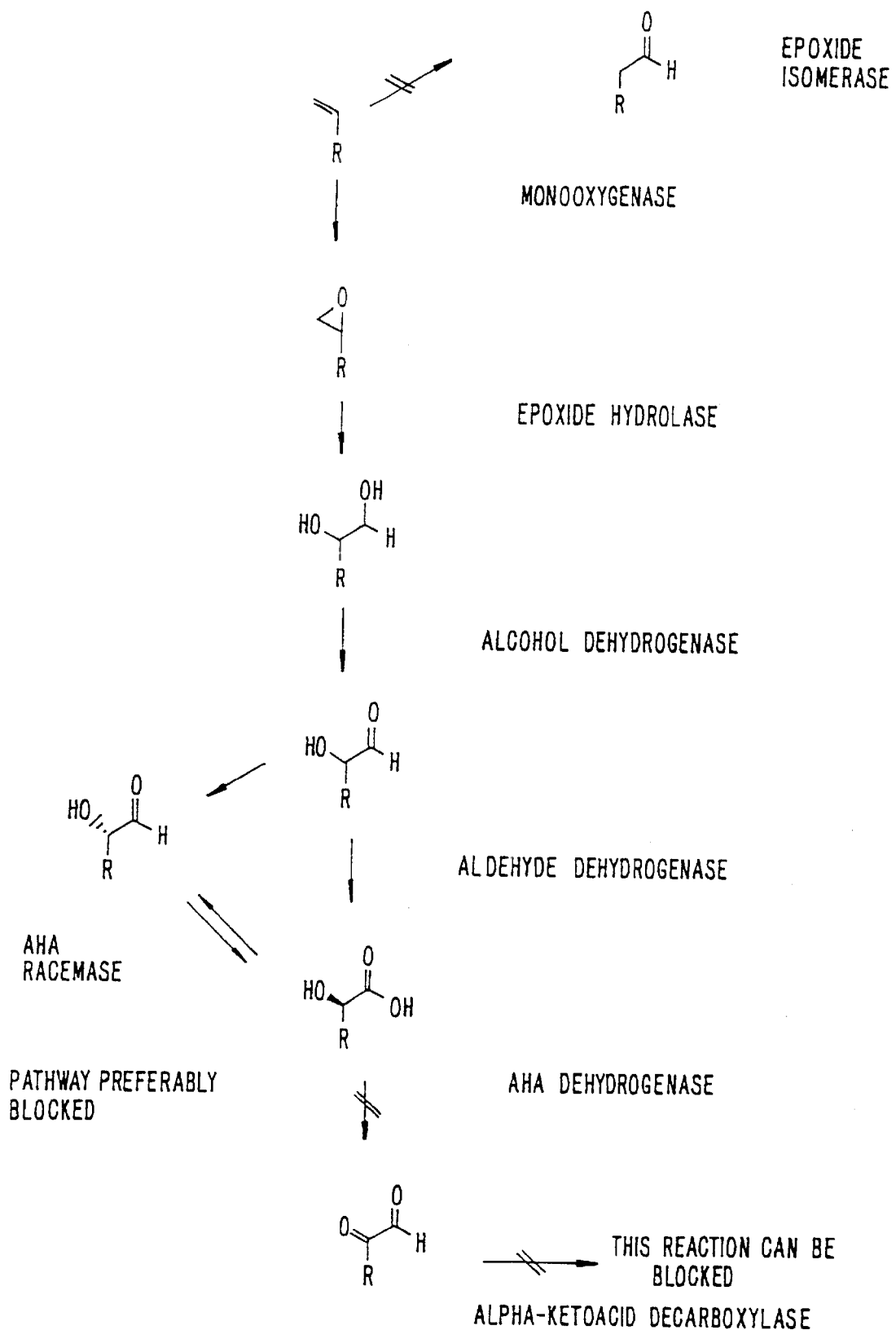
FIG. 2. Structures of exemplary feedstock olefinic compounds and structures of α-hydroxycarboxylic acids.

In yet another preferred embodiment of this invention, the described reactions and pathways are utilized for biocatalytic whole-cell conversion of styrene to mandelic acid and its ester derivatives. The pathway for styrene conversion, all of its intermediates and reactions are shown in FIG. 2.

The esterified adducts provide an increase in the overall efficiency of the biotransformation process as they simplify end-product recovery. The esters are easily isolated by organic solvent extraction and partitioning. Moreover, the adducts obviate the need for pH adjustment in the aqueous fermentation media to prevent the accumulation of the high levels of acidic biotransformation products.

There are several biochemically distinct means by which AHAs can be biocatalytically esterfied in a substantially aqueous environment. In one preferred embodiment of this invention, expression of genes encoding an S-adenosylmethionine (SAM)-dependent O-methyltransferase is used to effect conversion of AHAs to their methyl esters (e.g., FIG. 4, conversion of compound X to compound XI). SAM-dependent methyltransferases of differing substrate specificity are common in nature, and suitable enzymes and corresponding genes can be found and used directly for the purpose of this invention. Alternatively, these species can be further evolved and optimized for specific activity with the AHAs using one or more nucleic acid shuffling methods described herein. The invention also provides means for HTP screening for the presence, and quantitative determination, of the AHA-specific O-methyltransferase catalytic activities in microorganisms, cells, tissues or extracts of tissues of higher eukaryotic organisms. These methods can be used either to identify sources of corresponding genes or to evolve the desired specificity of known methyltransferases towards the AHAs by means of DNA shuffling described herein.

In another embodiment acyltransferase enzymes which specifically esterify the sec-hydroxyl of AHAs by means of active carboxyl transfer from either acyl-coenzyme A or acylated acyl carrier protein (ACP) are incorporated into the reaction pathway. This pathway is depicted in FIG. 4, as shown by the coupling of compounds X and XII to yield compound XIII. A preferred embodiment of this pathway, involves recruiting and expressing gene(s) encoding acyl-CoA-dependent acyltransferases, including those which utilize as substrates acetyl-CoA and CoA derivatives of fatty acids, as well as lactoyl-CoA, CoA-thioesters with other AHAs, and CoA derivatives of aromatic, arylalkanoic, branched chain alkanoic carboxylic acids, and alpha-aminoacids. Where carboxylic acids (either in from of free acid, salt or ester), intended for esterification of AHAs, are supplied exogenously, or are co-produced by another co-functioning biotransformation or fermentative pathway in the same host organism, or a different host organism, the invention provides a means for facilitating ester formation by recruiting and co-expressing those acyl-CoA ligases or ACPs which effect in-vivo activation of these acids forming suitable substrates for the acyl transferase enzymes that act on the AHAs.

The invention also provides for another type of biochemical transformation of AHAs to AHA carboxylic esters wherein free AHAs are first converted to their active ester form by means of the enzymatic formation of a derivative with CoA or ACP (FIG. 4, compound XIV). Several alternative acyltransferase enzymes (and genes encoding them) can be recruited for effecting subsequent transformations of compound XIV to esters of different compositions. These preferably include AHA-CoA transferases acting (a) on alcohols (XX) to produce esters (IX), or (b) on molecule of compound XIV or compound XV to produce acyclic homo- and hetero-oligomers (n=2–5) of AHAs. By recruiting an additional thioesterase enzymes, the activated forms of these oligomeric esters can be converted to free carboxylic oligomers (e.g., XVIII) or to the cyclic substituted glycolides (XVI).

In another preferred embodiment, the formation of an α-hydroxycarboxylic acid ester is catalyzed by an acyl CoA-ligase that is evolved by nucleic acid shuffling. In a preferred embodiment, shuffling of nucleic acids encoding acyl-CoA ligase activities results in an increase in the synthesis of esters. In another preferred embodiment, the esters are selected from structures XIII–XVIII (FIG. 4). The synthesis of these and other esters will generally rely on the provision of a corresponding α-hydroxycarboxylic acid precursor. In a preferred embodiment, the α-hydroxycarboxylic acid precursor is present in an amount sufficient to establish intracellular pools of CoA-activated carboxylic derivatives of α-hydroxycarboxylic acids.

In still another preferred embodiment, the transferase polypeptide is selected from glycosyltransferase and methyltransferase, more preferably methyltransferase and more preferably still a S-adenosylmethionine dependent O-methyltransferase.

5. Enzymes effecting chiral switch at the level of AHAs.

Another object of this invention is the effective control of the enantiomeric composition of the compounds prepared by the methods of the invention. For clarity of illustration, the discussion below focuses on AHA esters made by the biotransformation process from alkenes. This focus is intended to be illustrative and not limiting of the scope of this embodiment of the invention.

Means of enantiomeric control, when integrated as part of the multistep biocatalytic pathway, constitutes an important advantage as it allows selective production of either enantiomer of the AHA. The enantiomerically pure AHAs can be used as resolving reagents, chiral synthons, or monomers for polyesters or co-polyesters with lactic acid.

In a preferred embodiment, the AHA is mandelic acid, or an analogue thereof, and the chiral switch is effected by recruiting mandelate a racemase gene.

Mandelate racemase catalyzes the interconversion of the R and S enantiomers of mandelic acid and its derivatives. An exemplary mandelate racemase is that of *Pseudomonas putida* (the sequence of the gene can be found in the GenBank database under the locus [PSEMDLABC]). Preferred mandelate racemases are those of the *P. putida* strain ATCC 12633, however, mandelate racemases from any other organism can be used.

Although, in a preferred embodiment, the chiral switch is made at the level of the AHA, this switch can be made with any of the precursors or adducts of the AHA as well. Thus, in yet another preferred embodiment, the AHA is modified by at least one of the ester-forming enzymes discussed herein. Preferred ester forming enzymes are those which specifically, or preferentially, act on one enantiomer of the AHA, thus allowing enantiospecific resolution of the racemate in-vivo. The activity of the above racemases provides an enantiomeric equilibrium at the expense of the non-esterified enantiomer. The combined action of the racemase and the AHA esterifying enzymes provides a chiral switch which allows preparation of one desired enantiomer, whether R or S, from AHAs of any enantiomeric composition.

6. Hydroxylation of organic substrates

The monooxygenase polypeptides of the invention are capable of hydroxylating substantially any substrate comprising a terminal methyl, internal methylene or π-bond group. These substrates include, for example, alkyl, substituted alkyl, aryl, substituted aryl, heteroaryl, substituted heteroaryl and the like. Other appropriate substrates will be apparent to those of skill in the art.

In a preferred embodiment, the substrate has the structure:

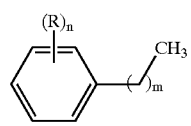

wherein, each of the n R groups is a member selected from the group consisting of H, alkyl groups and substituted alkyl groups; m is a number from 0 to 10, inclusive; and n is a number from 0 to 5, inclusive.

In another preferred embodiment, the substrate includes benzene substituted with a member selected from the group of straight-chain alkyl groups branched-chain alkyl groups and combinations thereof. The substituent is more preferably, a member selected from $C_1$–$C_6$ straight-chain, $C_1$–$C_6$ branched-chain alkyl and combinations thereof, and even more preferably, ethyl, n-propyl, i-propyl, t-butyl and combinations thereof.

In another preferred embodiment, the substrate has the structure:

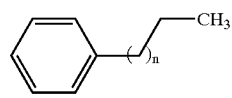

wherein, n is a number between 0 and 9, inclusive.

In yet another preferred embodiment, the substrate has the structure:

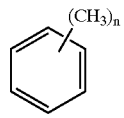

wherein, n is an integer from 1 to 6.

Presently preferred products of these oxidation reactions include benzyl alcohol, substituted benzyl alcohol, 2-phenylethanol, substituted 2-phenylethanol, 3-phenylpropanol, substituted 3-phenylpropanol and their derivatives.

In a still further preferred embodiment, the substrate includes a member selected from 3,4-dihydrocoumarin and 3,4-dihydrocoumarin residues and the poly peptide converts a methylene group of the substrate to —CH(OH)—.

In yet another preferred embodiment, the substrate is 3,4-dihydrocoumarin and the polypeptide converts the substrate to 4-hydroxy-4-dihydrocoumarin.

7. Preparation of hydroxylated aromatic carboxylic acids

Hydroxylated aromatic carboxylic acids have many diverse uses, including as antimicrobial additives, UV protectants (e.g. esters of p-hydroxybenzoic acid, parabens), pharmaceutical compositions (e.g., esters of salicylic acid, coumarins and 3,4-dihydroxycoumarin).

Thus, in another preferred embodiment, the present invention provides a method for preparing hydroxylated aromatic carboxylic acids. The method includes contacting a substrate comprising an aryl carboxylic acid with a dioxygenase polypeptide of the invention. The polypeptide is preferably expressed by an organism of the invention.

a. Carboxylic acid substrates

The carboxylic acids used as substrates in the present invention can be obtained from commercial sources, or they can be prepared by methods known in the art. In a preferred embodiment, the carboxylic acids are prepared by contacting a substrate comprising an aryl alkyl group with an oxygenase polypeptide to produce the corresponding aryl alkyl alcohol. The alcohol is subsequently acted upon by a dehydrogenase polypeptide to produce the desired carboxylic acid. Alternatively, the alcohol can be converted to COOH by chemical means.

For clarity of illustration, the discussion herein focuses on the oxidation of arylmethyl groups to carboxylic acids. This focus is intended to be illustrative and not limiting.

(i). Alkyl group monooxygenation

The first step in the biotransformation processes for conversion of alkylaryl compounds, such as toluene and isomeric xylenes includes the selective oxidation of at least one methyl group present in the aromatic substrate to the corresponding carboxylic acid (e.g., benzoic, toluic acids). In an exemplary embodiment, the substrate is a p- or a m-xylenes and preferably, only one of the methyl groups is oxidized.

Following the oxygenation step, the resulting alcohol is dehydrogenated, generally by the action of a dehydrogenase polypeptide to produce the desired carboxylic acid.

The invention provides for polypeptides that selectively oxidize only one alkyl group of an arene bearing two or more alkyl substituents. In an exemplary embodiment, xylene is converted to a monocarbocylic acid. Alternatively, the invention provides polypeptides that are capable of oxidizing more than one alkyl substituent of a species substituted with two or more alkyl groups. This is in contrast to certain polypeptides of the invention are capable of oxidizing both of the methyl substituents of a xylene to produce the corresponding benzenedimethanol (4a).

In a preferred embodiment, the monoxygenation/dehydrogenation pathway produces a carboxylic acid having the structure:

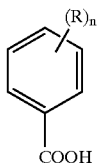

wherein each of the n R groups is independently selected from H, alkyl and substituted alkyl groups; and n is a number from 1 to 5, inclusive, more preferably R is methyl, and more preferably still, n is a number from 1 to 3, inclusive.

In a still further preferred embodiment, the carboxylic acid is selected from:

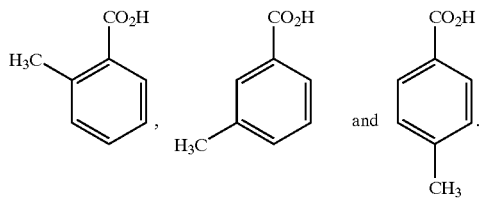

Many enzymes for effecting these reactions are well known in the art, and are suitable for use in the construction of useful polypeptides and host strains. To achieve the initial oxidation of the methyl groups, certain enzymes are presently preferred, including non-heme multicomponent monooxygenases of toluene and xylenes, and p-cymene, as well as certain arene dioxygenases which act on these substrate in a monooxygenase mode. The latter are exemplified by naphthalene dioxygenase, 2-nitrotoluene 2,3-dioxygenase and 2,4-dinitrotoluene 4,5-dioxygenase. These dioxygenases do not oxidize the aromatic ring of methylbenzenes, but are capable of oxidizing methyl groups of a variety of aromaticcompounds in a monooxygenase mode (Selifonov, et al., *Appl. Environ. Microbiol.* 62(2):507–514 (1996); Lee et al., *Appl. Environ. Microbiol.* 62(9):3101–3106 (1996); Parales, et al., *J. Bacteriol.* 180(5):1194–1199 (1998); Suen et al., *J. Bacteriol.* 178(16):4926–4934 (1996). As with the other polypeptide activities discussed herein, the ability of a dioxygenase to act as a monooxygenase is a property that can be optimized by shuffling the nucleic acids encoding these dioxygenases.

The following list provides examples of polynucleotides that encode dioxygenases acting as monooxygenases and which are suitable for use in the methods of the invention. The loci are identified by GenBank ID and encode complete or partial protein components of the arene dioxygenases. Suitable loci include:

[AB004059], [AF010471], [AF036940], [AF053735], [AF053736], [AF079317], [AF004283], [AF004284], [PSENAPDOXA], [PSENAPDOXB], [PSENDOABC], [PSEORF1], [PSU49496] naphthalene-1,2-dioxygenase; [BSU62430] 2,4-dinitrotoluene dioxygenase; [PSU49504] 2-nitrotoluene dioxygenase.

The polypeptide that catalyzes the monooxygenation can be a naturally occurring polypeptide, or it can have one or more properties that are improved relative to an analogous naturally occurring polypeptide. In a preferred embodiment, the polypeptides are expressed by one or more host organisms. Moreover, the polypeptide that catalyzes the monooxygenation can be co-expressed by the same host expressing a polypeptide used for further structural elaboration of the oxidation substrate or product (e.g., a dioxygenase polypeptide that oxidizes the π-bond). Alternatively, the mono- and di-oxygenase polypeptides can be expressed in different hosts.

(ii). Oxidation of alkylarenes having alkyl groups with $\geq C_2$

While much of the discussion above highlighting pathway and organism construction for oxidation of methylbenzenes is directly applicable to the set of processes dealing with alkyl benzenes bearing other alkyl groups.

Thus, in a preferred embodiment, at least one alkyl group of the alkylarene has at least two carbon atoms. Preferred species produced in the monoxygenation step (and any subsequent structural elaboration) have the structure:

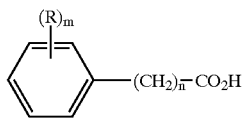

wherein each of the m R groups is selected from H, alkyl, substituted alkyl, aryl, substituted aryl, heteroaryl, substituted heteroaryl, heterocyclyl and substituted heterocyclyl; m is a number from 0 to 5, inclusive; and n is a number from 1 to 10, inclusive. Preferred aryl groups are those substituted on the aryl group with at least one methyl moiety.

In another preferred embodiment, the compound has the structure:

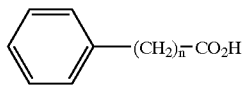

wherein n is a number from 1 to 6, inclusive.

Generally, oxidation of $C_2$ alkyl groups is best accomplished by expressing a suitable cytochrome P450 type enzyme system. The enzymes of this class are ubiquitous in nature, and they can be found in a variety of organisms. For example, n-propylbenzene is known to undergo □-oxidation in strains of *Pseudomonas desmolytica* S449B1 and *Pseudomonas convexa* S107B1(Jigami et al., *Appl. Environ. Microbiol.* 38(5):783–788 (1979)) which can utilize this hydrocarbon in either of two alternative oxidation pathways.

Similarly, well known in the art, alkane monooxygenases of bacterial origin, or cytochromes P450 for camphor oxidation, whether wild-type or mutant, can be recruited for the purpose of introducing the oxygen at the terminal methyl group of alkylarenes (Lee et al., *Biochem. Biophys. Res. Commun.* 218(1):17–21 (1996); van Beilen et al., *Mol. Microbiol* 6(21):3121–3136(1992); Kok et al., *J. Biol. Chem.* 264(10):5435–5441 (1989); Kok et al., *J. Biol. Chem.* 264(10):5442–5451 (1989); Loida et al., *Protein Eng.* 6(2): 207–212 (1993).

(iii) Oxygenation of arenes with exocyclic π-bonds

In another preferred embodiment, the starting material for the carboxylic acid is an arene bearing an exocyclic π-bond. This class of compounds is exemplified by styrene. Other analogous species are set forth in FIG. 3.

The conversion of the exocyclic π-bond is best accomplished by recruiting a cluster of bacterial styrene oxidation genes well known in the art (Marconi et al., *Appl. Environ. Microbiol.* 62(1):121–127 (1996); Beltrametti et al., *Appl. Environ. Microbiol.* 63(6):2232–2239 (1997); O'Connor et al., *Appl. Environ. Microbiol.* 63(11):4287–4291 (1997); Velasco et al., *J. Bacteriol.* 180(5):1063–1071 (1998); Itoh, et al., *Biosci. Biotechnol. Biochem.* 60(11):1826–1830 (1996). Alternatively, the styrene epoxidation step can be accomplished by using monooxygenases active towards methyl substituted aromatic compounds, such as toluene or xylenes (Wubbolts, et al., *Enzyme Microb. Technol.* 16(7):608–615 (1994).

(iv). Dehydrogenation

To produce the desired carboxylic acid, the alcohol from (i–iii), above, is preferably treated with a dehydrogenase polypeptide. The dehydrogenase enzymes can be endogenous to a host that expresses one or more of the oxygenase polypeptides, or it can exhibit properties that are improved relative to an endogenously expressed dehydrogenase.

The polypeptide that catalyzes the dehydrogenation can be a naturally occurring polypeptide, or it can have one or more properties that are improved relative to an analogous naturally occurring polypeptide. In a preferred embodiment, the polypeptides are expressed by one or more host organisms. Moreover, the polypeptide that catalyzes the dehydrogenation can be co-expressed by the same host expressing one or more of the dioxygenase polypeptide. Alternatively, the dehydrogenase and oxygenase polypeptides can be expressed in different hosts.

In yet another preferred embodiment, the invention provides a method for altering or controlling the regiospecificity of the dehydrogenation reaction of a vicinal diol. This method "blocks" one of the vicinal diol hydroxyl groups by forming an ester, for example. The method includes contacting the vicinal diol with a polypeptide, preferably expressed by a host organism, having an activity selected from ligase, transferase and combinations thereof, thereby forming a α-hydroxycarboxylic acid adduct. As with the other polypeptides discussed above, this polypeptide can be expressed by the same host cell that expresses other polypeptides of the reaction cascade. Moreover, this polypeptide can be a naturally occurring polypeptide, or it can be improved using the method of the invention.

b. Monooxygenation of aromatic π-bonds

In the synthesis of hydroxyaryl carboxylic acids using the methods of the invention, once the carboxylic acid moiety is in place, the molecule is submitted to an arene monooxygenation cycle (FIG. 1). The monooxygenation of the aromatic ring is preferably accomplished by recruiting one or more monooxygenase genes, preferably of bacterial origin. Exemplary monooxygenase genes are disclosed herein. The method of the invention can be practiced using essentially any type of aromatic ring system. Exemplary aromatic systems include, benzenoid and fused benzenoid ring systems (e.g, benzene, napthalene, pyrene, benzopyran, benzofuran, etc.) and heteroaryl systems (pyridine pyrrole, furan, etc.). In a preferred embodiment, the substrate includes a benzenoid hydrocarbon.

Similar to the embodiments discussed above, in this embodiment, the polypeptide that catalyzes the monooxygenation can be coexpressed with one or more polypeptides used in a synthetic pathway. For example, the monooxygenase, dehydrogenase and transferasease polypeptides can all be coexpressed in a single host. Other functional combinations of coexpression will be apparent to those of skill in the art.

8. Conversion of hydroxyls and/or acids to esters

In another preferred embodiment, there is provided a method for converting carboxylic acid and hydroxyl groups to adducts such as esters and ethers. Useful polypeptides include ligases and transferases (see, FIG. 4). For the purposes of the discussion below, these polypeptides are referred to as "adduct-forming" polypeptides.

The adduct-forming polypeptides are useful for enhancing the production of biotransformation products. These polypeptides, which convert a diol, for example, to a monoacyl or monoglycosyl derivative, can enhance control over the regioselectivity of subsequent reactions (e.g., chemical dehydration). For example, the regioselectivity of chemical dehydration in certain cases can be controlled by converting the compounds to their diacyl derivatives by means of chemical reaction, and then selectively removing one of the acyl groups using an polypeptide of the invention. Alternatively, one can control the regioselectivity of the dehydration by using an esterase or a trans-acylase polypeptide to convert the compounds to monoacyl derivatives in the presence of an excess of another carboxylic acid ester, in an essentially organic medium. In addition, acylation of diols, for example, to obtain monocarboxylic esters provides advantages for efficient recovery of such esters by means of organic solvent extraction, including by extraction with organic solvents which may be used in an immiscible biphasic organic-aqueous biotransformation with whole cells, whether in a batch or in a continuous mode.

An adduct-forming polypeptides can be expressed by the same host cell that expresses the monooxygenase, dehydrogenase, racemase, etc., or it can be expressed by a different host cell. Moreover, an adduct-forming polypeptide can be a naturally occurring polypeptide, or it can be improved by the method of the invention.

When the adduct-forming polypeptide is an improved polypeptide, in presently preferred embodiments, the polypeptides can, for example, demonstrate increased efficiency in the formation of the monoacyl- or monoglycosyl-derivatives of a desired compound (e.g, a glycol, carboxylic acid, etc.). Other improved adduct-forming polypeptides include transferases and ligases that can selectively modify only one of the hydroxyl groups of a diol, thus providing a means for control of regioselectivity of dehydration of such derivatives to either of two possible isomeric α-hydroxycarboxylic acid compounds.

9. Conversion of fatty acids to hydroxy acids

In another preferred embodiment, there is provided a method for converting fatty (preferably, alkanoic, n=3–20) acids to hydroxy acids. Monooxygenases are well known to those skilled in the art to perform the oxidation of remote carbons in a fatty acid. Improved polypeptides will have selectivity for the oxidation of any position in the chain. These hydroxyacids can then be used as substrates for polymer formation.

E. Antioxidant and Impurity Modification and Detoxification

In another embodiment, the invention provides a means for degrading or modifying organic materials which leads to their detoxification. Exemplary compounds include stabilizing agents, antioxidizing agents, environmental pollutants and the like. This method is applicable to substantially any compound that can be detoxified by, for example, oxidation, either with or without additional structural elaboration. For clarity of illustration, the discussion below focuses on the detoxification of agents commonly found in organic solvents and in π-bonded compounds of use in the present invention.

Many commercially available compounds (e.g., alkylbenzenes, alkenes, etc.) are stabilized with small amounts of antioxidants such as 4-tert-butylcatechol or alkylphenols (e.g. BHT) to prevent polymerization during storage and transportation. While the amount of these compounds is usually relatively small (10–15 ppm), they can inhibit biocatalyst performance as they accumulate in aqueous fermentation medium during prolonged incubations required to obtain satisfactory endproduct concentrations.

Several types of enzymes for modifying the phenolic stabilizing compounds can be used to alleviate any negative effects of these compounds on the whole cell biocatalyst performance. Their genes can be introduced in the same host organism used to produce endproducts or intermediate of relevance to his invention. Alternatively, they can be incorporated into a separate host organism. This obviates the need for additional steps in the process which may be required in order to remove these stabilizers. Optimization of one or several of these enzymes for the efficient removal of these stabilizing compounds is a target for DNA shuffling.

Exemplary enzymes for modifying phenolic and diphenolic stabilizers include, but not limited to, acyltransferase, methyltransferase, glycosyltransferase, lactase and peroxidase. In addition to these enzymes, catecholic stabilizers also can be modified to innocuous products by catechol dioxygenases effecting meta- or ortho-ring cleavage. Many of these enzymes show a significant breadth of activity towards compounds related to phenolic stabilizers. Thus, DNA shuffling can be applied to optimize enzyme parameters such as:

a) increased turnover with particular phenolic stabilizer,
b) increased functional expression, by obviating the requirements for certain post-transitional modifications of those enzymes which require such modifications (e.g. glycosylation of peroxidases and lactases); and
c) alleviation of inhibition of these enzymes by high concentration of co-occurring feedstock compounds and intermediates and endproducts of the biocatalytic process.

F. Analytical Methodology

A number of analytical techniques are useful in practicing the present invention. These analytical techniques are used to measure the extent of conversion of a particular substrate to product. These techniques are also used to analyze the regioselectivity and/or the enantiomeric selectivity of a particular reaction catalyzed by a polypeptide of the invention. Moreover, these techniques are employed to assess the effect of nucleic acid shuffling experiments on the efficiency and selectivity of the polypeptides produced following the shuffling. The discussion below focuses on those aspects and embodiments of the invention in which an olefin precursor is oxidized by a monooxygenase. The analytical techniques discussed in this context are generally of broad applicability to other aspects and embodiments of the invention. This is particularly true of the spectroscopic and chromatographic methods discussed below. Thus, in the interest of brevity, the following discussion focuses on analyzing the products of the oxidation of an olefin, but the utility of the methods discussed is not limited to this embodiment.

1. Selecting for Monooxygenase activity

Monooxygenase activity can be monitored by HPLC, gas chromatography and mass spectroscopy, as well as a variety of other analytical methods available to one of skill. The consumption of molecular oxygen by the monooxygenase can be measured using an oxygen sensing system, such as an electrode. Incorporation of $^{18}O$ from radio-labeled molecular oxygen can be monitored directly by mass shift by MS methods and by an appropriate radioisotope detector with HPLC and GC devices. For example, epoxidation of 1-hexadecene to 1,2-epoxyhexadecene can be monitored by $^{18}O$ incorporation either in intact whole cell or lysate. This has been used, for example by Bruyn et al with *Candida lipolytica*.

In addition, epoxide formation can be indirectly measured by various reactive colorimetric reactions. When $H_2O_2$ is used as the oxidant, disappearance of peroxide over time can be monitored directly either potentiometrically or calorimetrically using a number of commercially available peroxide reactive dyes.

In a high-throughput modality, the method of choice is high-throughput MS, or MS with an electron spray-based detection method. In addition, selection protocols in which the organism uses a given alkane, alkene or epoxide as a sole carbon source can be used. In some systems this will be most readily accomplished by combining the alkene oxidizing polypeptide with an epoxide hydrolase to generate a metabolizable alcohol.

2. Automation for Strain Improvement

One key to strain improvement is having an assay that can be dependably used to identify a few mutants out of thousands that have potentially subtle increases in product yield. The limiting factor in many assay formats is the uniformity of library cell (or viral) growth. This variation is the source of baseline variability in subsequent assays. Inoculum size and culture environment (temperature/humidity) are sources of cell growth variation. Automation of all aspects of establishing initial cultures and state-of-the-art temperature and humidity controlled incubators are useful in reducing variability. In one aspect, library members, e.g., cells, viral plaques, spores or the like, are separated on solid media to produce individual colonies (or plaques). Using an automated colony picker (e.g., the Q-bot, Genetix, U.K.), colonies are identified, picked, and 10,000 different mutants inoculated into 96 well microtitre dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtiter plates act to promote uniform aeration of cells and the dispersal of mycelial fragments similar to the blades of a fermenter.

a. Prescreen

The ability to detect a subtle increase in the performance of a shuffled library member over that of a parent strain relies on the sensitivity of the assay. The chance of finding the organisms having an improvement is increased by the number of individual mutants that can be screened by the assay. To increase the chances of identifying a pool of sufficient size, a prescreen that increases the number of mutants processed by 10-fold can be used. The goal of the primary screen will be to quickly identify mutants having equal or better product titres than the parent strain(s) and to move only these mutants forward to liquid cell culture for subsequent analysis.

In one preferred embodiment, the prescreen for P450 activity is a method for measuring functional heme incorporation. Active P450 monooxygenases have an absorbance at around 450 nm in the presence of carbon monoxide in a reducing environment. Thus expression of the P450 library on an agar plate is followed by the addition of a reducing solution, such as dithionite in water. This solution is then removed and the plate is placed in a CO atmosphere. Colonies with increased absorbance at 450 nm are picked as active cytochrome P450 enzymes. This screening process is general for all P450 monooxygenases.

3. Selection for Redox Partners

One target for the application of gene shuffling technologies is to evolve monooxygenases to use cheaper, more practical redox partners. However, the complexities of managing redox equivalents can be circumvented, in many cases, by using peroxides (such as hydrogen peroxide) as co-substrates. For example, a monooxygenase capable of oxidizing 1-octene to 1,2-epoxyoctane does so in a non-NAD(P)H-dependent manner when $H_2O_2$ is added to the reaction mix. For peroxidases and chlorperoxidases this peroxide-dependent, NAD(P)H-free oxidative chemistry is the norm. Peroxide-mediated oxidations, however, often result in the rapid inactivation of catalytic activity by a variety of partially understood mechanisms enzymes (see, CYTOCHROME P450: STRUCTURE, MECHANISM, AND BIOCHEMISTRY [2nd edition], P. R. Ortiz de Montellano, editor, New York: Plenum Press, chapter 9; and Meunier, B. *Chem. Rev.* 92:1411–1456 (1992)). Enhancing the stability of P450 enzymes in the presence of peroxides and increasing the overall turnover rates of these enzymes with basic industrial raw materials is a feature of the invention.

Gene shuffling offers a means of generating new peroxidase and oxygenase polypeptides with altered selectivity, activity or stability. Whereas peroxides are often prohibitively expensive for use as oxidants for industrial chemistry, biological systems offer the potential to generate and use peroxides in situ without isolation of the reactive intermediates. The concepts disclosed here include the coevolution of a hydrogen peroxide-generating system (such as glucose, galactose or alcohol oxidases) with a monooxygenase polypeptide capable of using the peroxide generated to synthesize an oxidized coproduct. In this context, peroxides can be commercially feasible oxidizing agents for even low-value, high-volume commodity chemicals.

4. Screening for improved monooxygenase activity.

In each of the aspects and embodiments discussed below, the concept of screening the library of recombinant polypeptides to enable the selection of improved member s of the library is set forth. Although it will be apparent to those of skill in the art that many screening methodologies can be used in conjunction with the present invention, the invention provides a screening process comprising:

(a) introducing the library of recombinant polynucleotides into a population of test microorganisms such that the recombinant polynucleotides are expressed;

(b) placing the organisms in a medium comprising at least one substrate; and (c) and identifying those organisms exhibiting an improved property compared to microorganisms without the recombinant polynucleotide.

a. Oxidation of olefins

Depending on the specific outcome desired from a particular course of DNA shuffling of nucleic acids encoding oxygenases for biocatalytic oxidation of olefins, the invention provides several methods for detecting and measuring catalytic properties encoded by the recombinant polynucleotides. These are exemplified by the following methods.

For the purpose of the optimization of individual reactions and whole pathways for production of α-hydroxycarboxylic acids, their derivatives, analogues and precursor compounds described in this invention can be monitored by virtually any analytic technique known in the art. In preferred embodiments, the production of the desired compound is monitored using one or more techniques selected from thin layer chromatography (TLC), high performance liquid chromatography (HPLC), chiral HPLC, mass-spectrometry, mass spectrometry coupled with a chromatographic separation modality, NMR spectroscopy, radioactivity detection from a radioactively labeled compounds (e.g., —olefins, diols, aldehydes, AHAs, etc.), scintillation proximity assays, and by UV-spectroscopy. In a high throughput modality, the preferred methods are selected from one or any combination of these methods.

The methods of the invention are used to improve polypeptides that catalyze the initial oxidation of π-bonded species. Methods using monooxygenase-based pathways are encompassed herein. The oxidation product from the conversion of a substrate comprising a π-bond (e.g., arenes, alkylarenes, alkenes, etc.) can be detected by numerous methods well known to those of skill in the art. Certain preferred methods are set forth herein.

In a preferred embodiment, the vicinal diol derived from oxidation of an olefin is quantitated using a radioactively labeled substrate. Although any radioactive isotope commonly used in the art can be incorporated into a substrate, preferred isotopic labels include, for example, $^{14}C$ and/or $^{3}H$. Differences in the volatility of the olefin substrate and the corresponding diol can be exploited to quantitate the radioactively labeled product. This method can easily be applied to aqueous samples of culture fluids obtained by incubating individual clones of cells expressing libraries of a recombinant polynucleotide obtained using the methods of the invention.

In an exemplary embodiment, cells expressing libraries of recombinant polynucleotides encoding a monooxygenase can be grown in a multiwell dish with a radioactive substrate administered directly to the aqueous medium. After incubation of the cells with the radioactive olefin substrate, any residual uncoverted substrate is removed by evaporation, with or without application of vacuum. After removing the unconverted substrate, the culture fluid (or aliquots thereof) is mixed with a suitable scintillation cocktail, and the radioactivity in the samples is quantitatively measured. In a preferred embodiment, selection of the most active clones is based on the amount of radioactivity incorporated into the compounds produced by the organisms expressing the clone.

Alternatively, radioactively labeled substrate can be administered as a vapor phase to colonies growing on a surface of a membrane filter overlaying agar-solidified medium. After incubation, the membrane is removed from the agar surface, and any residual hydrocarbon is evaporated from the membrane. The membrane is autoradiographed, or a scintillation dye is sprayed over the membrane for radioactivity detection. A modification of this assay that is particularly suitable for $^{14}C$ label detection in and/or around colonies capable of oxidizing π-bonds to the corresponding glycols involves using a porous membrane that has scintillation dye incorporated in the membrane composition by covalent or adsorption means. This assay is termed "scintillation proximity assay on membrane" or "SPA."

In another embodiment of this invention, a variation of SPA is used to selectively quantify the glycol derived from the substrate. This variation involves adding beads for scintillation proximity assay to the samples of culture fluids or extracts obtained by incubation of cells with radiolabeled substrate as described above. Alternatively, the sample can be applied to a membrane. The beads or membrane are functionalized with groups that interact with a glycol.

In a preferred embodiment of this assay, the beads or membranes contain a suitable scintillating dye and their surfaces are modified by chemical groups that interact readily with diols. Such materials can be prepared by known chemical methods from commercially available SPA materials and they can be used to trap free diols directly in the aqueous medium or culture broths obtained by incubation of the microbial cells with the radiolabeled substrates.

In another preferred embodiment, the surface of the beads used in this assay is functionalized with a sufficient amount of a compound that interacts with a glycol, such as compounds containing aryl or alkylboronate (boronic acid). Such beads can be obtained by chemical modification of commercially available SPA beads by reactions known to one skilled in the art. In a preferred embodiment, the reactions used to modify the beads are analogous to those used for the preparation of arylboronate-modified resins for solid-phase extraction or chromatography. After incubation, the beads are washed with a sufficient amount of water or other suitable solvent and subjected to quantitative determination of radioactivity.

One can also determine amounts of glycol produced by oxidation of an π-bond by taking advantage of the reactive nature of the substrate. Samples of culture fluids, or extracts in an appropriate solvent, can be treated with known excess amounts of dilute solutions of, for example, a halogen ($Cl_2$, $Br_2$, $I_2$), permanganate salts. The residual excess amount of those reagents, left after reaction with any substrate present, can be measured by chemical methods known in the art for determination of these compounds (see, for example, VOGEL'S PRACTICAL ORGANIC CHEMISTRY $5^{th}$ Ed., Furniss et al., Eds., Longman Scientific and Technical, Essex, 1989).

Mass spectrometry can also be used to determine the amount of a vicinal glycol formed due to species encoded by the libraries of shuffled oxygenase genes. Mass spectrometric methods allow ion peaks to be detected. The ion peaks derived from the vicinal glycol can be readily distinguished from peaks derived from olefin substrates. In a preferred embodiment, coordination ion spray or electrospray mass spectrometry is utilized.

In another preferred embodiment, a compound that interacts with a component of the mixture, preferably the glycol, is utilized to enhance the sensitivity and selectivity of the method. In a presently preferred embodiment, the sample analyzed contains excess arylboronic or alkylboronic acid. Preferred boronic acids are those containing at least one nitrogen atom and include, but are not limited to, dansylaminophenylboronic acid, aminophenylboronic acid, pyridylboronic acid.

The ions detected in the mass spectrum derive from cyclic boronate ester derivatives of the glycols with a boronic acid. The samples are preferably analyzed in non-acidic and non-basic organic solvent or aqueous phase, substantially free of alcohols and other glycols. Other appropriate analytical conditions will be apparent to those of skill in the art.

Another preferred method for quantitating the glycols uses periodic acid or its salts, preferably the sodium salts, to cleave the vicinal glycols to the corresponding aldehydes. In a preferred embodiment, vicinal diols other than the analyte (e.g., carbohydrates) are excluded from the aqueous or organic solvent samples. This is easily attained by using non-carbohydrate carbon sources to grow the microbial cells, and/or by removal of the cells from the media by centrifugation or filtration prior to contacting of the sample with periodate reagent. The periodate reagent can be used in solution, or preferably, immobilized on a solid phase (e.g. anion exchange resin). After reacting the glycol with an excess of periodate ion, the amount of free aldehyde groups can be measured by a variety of assays know in the art. In a preferred method, the aldehydes are quantitated by a method based on the formation of a colored hydrazone derivative. Alternatively, when using radioactively labeled olefins for biotransformation, the free aldehydes obtained by this method can be trapped by aldehyde reactive groups (e.g., free amines) on the surface of an appropriately modified SPA beads or membranes.

b. Methods for detecting alternative regioselectivity of oxidation of species with multiple π-bonds In one embodiment, the substrate includes more than one π-bond (e.g., styrene, butadiene, etc.). In a preferred embodiment, one of the π-bonds undergoes reaction more readily than the other. In this embodiment, it is generally preferred to determine which of the π-bonds underwent reaction. The preferred method for making this determination is $^1H$ or $^{13}C$ NMR, although other methods can be used. Other methods include, for example, chromatography (e.g., TLC, GC, HPLC, etc.), UV/vis spectroscopy and IR spectroscopy. In an embodiment wherein the reaction is operating in a high throughput mode, the method of choice is a flow-through $^1$H or $^{13}$C NMR spectroscopy.

When $^{13}$C NMR is used, the substrates are preferably labeled with $^{13}$C. π-bonded species can be synthesized by methods know in the art from a $^{13}$C enriched material to incorporate one, or any combination of several, labeled carbon atom(s) into the structure of these compounds. The enrichment levels for the labeled positions are preferably at least 5% of $^{13}$C, more preferably 50% and more preferably still 95% for any given labeled position. Incorporation of a $^{13}$C label provides a number of advantages, such as increasing the NMR signal and decreasing time required for spectral acquisition. Moreover, labeled compounds allow for a quantitative or semi-quantitative interpretation of the composition of a mixture of isomeric oxidation products. Preferably, incubations with $^{13}$C labeled olefins are conducted in multi-well plates, and aliquots of culture fluids or their extracts are sampled with an autosampler communicating with the NMR probe. In another preferred embodiment, the reaction components are not chromatographed or otherwise purified prior to obtaining a NMR spectrum.

Determining the absolute configuration and the enantiomeric composition of the glycols formed from π-bonded species, preferably employs a variation of the method described above for determining regioselectivity of dihydroxylation of the olefinic substrates by a monooxygenase using $^1$H or $^{13}$C NMR. In a preferred embodiment, the substrates are labeled with $^{13}$C and $^{13}$C NMR, is employed. This method preferably involves the use of a chiral and essentially enantiomerically pure derivatizing reagent such as a substituted arylboronic acid which forms a cyclic boronate derivatives with vicinal glycols, as know in the art (references: Resnick, Gibson, 1997, cite). In a preferred embodiment, both the substrates and one or more carbon atoms of the boronic acid is labeled with $^{13}$C. Although a broad range of boronic acids are of use in the present invention, a currently preferred boronic acid is shown below:

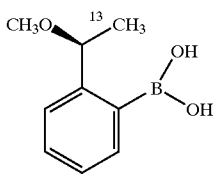

The absolute configuration of any chiral center of the compounds produced by the methods of the invention can be either R or S. In presently preferred embodiments, the enantiomeric excess of the product is preferably 98% or more. NMR signals of different enantiomers of the reaction products can be distinguished in diastereomeric products using substantially enantiomerically pure boronate compounds as discussed above. Moreover, the relative intensity of the NMR signals arising from corresponding atoms of the diastereomeric products can be used for estimating the enantiomeric composition of the product(s) present in the sample.

c. Methods for detecting alternative regioselectivity of oxidation of alkylarenes Useful methods for determining the regioselectivity of the oxidation of alkylarene compounds are substantially similar to those described in section (ii), supra.

5. AHA formation from glycols

Among methods for specifically measuring the free AHAs produced in the biocatalytic process, those which are particularly preferred are methods using a variation of the scintillation proximity assay described above. These methods preferably use an excess of beads or membranes bearing one or more positively charged functional groups (e.g quaternary or tertiary or primary amines). In preferred embodiments, these beads or membranes act as an anion exchange medium and they selectively trap free AHAs, thereby removing them from aqueous culture broths. In another preferred embodiment, this method employs a radioactively labeled starting material, or subsequent intermediate, (e.g., glycol, epoxide, etc.). The radioactively labeled compound interacts with the beads or membrane. Prior to measuring the radioactivity associated with the beads or the membrane, non-specifically adsorbed label is preferably removed by evaporating excess radioactive compound and/or washing with an aqueous solution which does not cause elution of the AHAs from the anion-exchange beads or membrane.

Preferred methods for determining the chirality and absolute configuration of AHAs formed in the described biotransformation process are substantially similar to those methods employed in making these determinations with respect to the glycols, as discussed above.

6. Methods for determination of HCAs

In HTP mode, a preferred analytical method is flow-through $^1$H or $^{13}$C NMR spectroscopy. In the $^{13}$C NMR mode, the aromatic substrate for oxidation by a monooxygenase is preferably labeled by the $^{13}$C isotope. Alkylaryl compounds or the corresponding arylalkanoic acids are synthesized by methods know in the art from a $^{13}$C enriched material to incorporate one, or any combination of several, labeled carbon atom(s) into the structure of these compounds. The enrichment levels for any labeled position are preferably at least 5% of $^{13}$C, and more preferably at least 95%. Incorporation of $^{13}$C label increases sensitivity of the NMR measurement, decreases time required for acquisition of spectrum per sample, and allows for quantitative or semi-quantitative interpretation of compositions of mixtures of isomeric oxidation products. Preferably, incubations with $^{13}$C labeled precursors are conducted in multi-well plates, and aliquots of culture fluids or their extracts are sampled with autosampler connected to the solvent line passing through NMR probe without any column separation.

For determining absolute configuration and enantiomeric composition of the HCAs, a variation of the methods described above for determining reaction regioselectivity by $^1$H or $^{13}$C NMR is used. In conjunction with the preferred use of $^{13}$C labeled substrates, $^{13}$C NMR is preferably employed.

The absolute configuration of any chiral center may be either R or S. In a preferred embodiment, the enantiomeric excess is 98% or more. NMR signals of different enantiomers of HCAs can be distinguished in diastereomeric products using known methods, such as NMR in conjunction with lanthanide shift reagents—or after derivatization with Mosher's esters. Alternatively the enantiomeric excess can be determined by chiral GC.

In another preferred embodiment, a variation of the SPA method is used. In this version, a solid support, such as beads or a membrane containing a suitable scintillation dye is used. The solid support is modified with positively charged groups such that it acts like an anion-exchange material. These materials can be prepared from commercially available SPA materials and they can be used to trap free acids directly in the aqueous medium or culture broths obtained by incubation of the host cells with a radiolabeled alkylarene.

7. Methods for determination of esters

In the interest of brevity, the following discussion focuses on the determination of esters of AHAs. One of skill will appreciate that the same, or similar, methods can be used to determine esters of other compounds formed using the methods of the invention.

Both spectroscopic and non-spectroscopic methods can be used to quantitate the extent of ester synthesis and to characterize the esters. The preferred non-spectroscopic method for assaying AHA methyl ester formation catalyzed by methyl transferases is based on use of a radioactively labeled precursors to AHA methyl esters. $^{14}C$ or $^{3}H$ methyl labeled SAM (or its in-vivo precursor, methionine) can be used as a probe. In another preferred embodiment, the labeled substrate is the free α-hydroxycarboxylic acid itself.

Using the methods of the invention, methyltransferases that are selective for a particular AHA enantiomer can be selected and further improved by iterative cycles of DNA shuffling and this assay. The selectivity of the methyltransferases of the invention towards a particular enantiomeric configuration of an AHA is preferably measured using samples of the α-hydroxycarboxylic acids that are substantially enantiomerically pure. Host cells employed in this biocatalytic cycle will preferably lack AHA racemase activity (e.g. mandelate racemase). In another preferred embodiment, both AHA enantiomers have a different radioactive label, e.g. one enantiomer is labeled with $^{14}C$, and another with $^{3}H$ (at one or more H positions which do not readily exchange with water). Measurement of the radioactivity incorporated into the product is performed using a radioactivity detector that allows for the selective measurement of at least two different isotopes. This variation allows the evaluation of the enantioselectivity of a methyltransferases in a single sample.

The radioactivity associated with methyl esters of AHAs is preferably measured in samples which are obtained by selective extraction or partitioning of the methyl esters from neutral or moderately basic (pH about 6–10) aqueous culture samples. These samples can contain varying amounts of free, labeled AHA, of AHA salts and other non-labeled organic compounds. The samples are preferably obtained by incubating individual clones expressing methyltransferase libraries with the labeled AHAs. The incubation medium is subsequently extracted by a adding a defined amount of a preferably water-immiscible organic solvent, or by contacting the broth with a extraction medium (e.g. XAD-1180, or similar beads, or membrane).

In those embodiments employing an extraction medium, following its removal from contact with the broth, the extraction media is preferably washed to remove adventitiously bound compounds. Preferred wash solutions are aqueous that do not elute the AHA methyl esters from the extraction medium, but which remove other molecules adsorbed onto the medium. The radioactivity of the extracted material is then measured by methods well known in the art. In embodiments using beads or a membrane an appropriate scintillating dye is preferably used for detecting the radioactivity.

Substantially similar methods can also be employed for detecting other neutral esters of AHAs, such as those exemplified by glycolides (e.g., XVI, FIG. 13) and esters of type XX. Thus the same approach is useful for assaying and characterizing the ester forming activity of polypeptides represented by libraries of acyl-transferases, or by a combination of AHA-CoA: alcohol acyltransferases and AHA-CoA ligases. Variations on this method can include the use of a radioactively labeled alcohol (e.g., XIX) or any of its in-vivo metabolic precursor.

In another preferred embodiment, the method for detecting polypeptide activity leading to the formation of neutral AHA esters employs UV or fluorescence spectroscopy. This method is applicable to those embodiments in which the transferase activity yields products exhibiting distinct UV and/or fluorescent characteristics. Exemplary compounds include, for example, substituted or non-substituted esters of aromatic carboxylic acids (e.g., mandelic acid). In preferred embodiments of this method, a solvent or solid-phase extraction under neutral or moderately basic conditions (pH about 6–12) is performed on the cell culture medium. Compounds thus isolated are detected by measurement of their UV absorption or fluorescence. These spectral parameters are evaluated to determine relative amounts and identities of the products formed by the transferase reactions.

a. Screening for improved transferase activity

The screening of the transferase libraries, obtained by DNA shuffling or other methods as described above, is done most easily in bacterial or yeast systems by one or more of the screening methods described below.

(i). Methods for detecting increased activity of transferase reactions

The methods for detection of increased formation of monoacyl- and monoglycosyl-derivatives of, for example, glycols and α-hydroxycarboxylic acids include methods in which physical differences between the substrates, the cis-diols and the derivatives arising from the transferase-catalyzed reactions are measured. Preferred methods include HPLC and mass-spectrometry. In a high throughput modality, a method of choice is mass-spectrometry, preferably, coordination ion and/or electrospray mass-spectrometry.

For acyl transferases, another presently preferred method uses a labeled acyl-donor precursor, e.g. labeled carboxylic acid or its derivative, administered to the cells that express libraries of shuffled genes encoding acyl ligases and/or acyl transferases, e.g., acyl-CoA ligases and acyl-CoA transferases. The amount of label in the hydrophobic reaction products is measured after extraction of the labeled derivatives into a suitable organic solvent, or after solid-phase extraction of these compounds by addition of a sufficient amount of hydrophobic porous resin beads (e.g., XAD 1180, XAD-2, -4, -8). In the case of a radiolabeled compound, scintillating dye can be present in the organic solvent, added to the samples, or chemically incorporated in the bead polymer. The latter constitutes a modification of scintillation proximity assay method.

(ii) Methods for detecting regioselectivity of transferase reactions.

The methods for detecting regioselectivity of the transferase reactions include HPLC, and in an HTP modality, flow-through NMR spectroscopy. When NMR spectroscopy is used for determining relative amounts of different regiomeric monoacyl or monoglycosyl derivatives of oxidized substrates, the latter are preferably obtained by action of the arene monooxygenases on isotopically ($^{13}C$ and/or $^{2}H$) labeled substrate. Another variation of the NMR technique includes use of isotopically labeled precursors of acyl- or glycosyl-donor intermediates.

8. Selecting for enhanced organic solvent resistance.

Selection for recombinant polynucleotides that provide improved organic solvent resistance can be accomplished by introducing the library of recombinant polynucleotides into a population of microorganism cells and subjecting the population to a medium that contains various concentrations of the organic hydrophobic compounds of interest. The medium can contain, for example, carbon, nitrogen and minerals, and preferably does not otherwise limit growth and viability of the cells in the absence of the solvent, thus ensuring that solvent resistance is essentially the only limiting factor affecting growth of the cells expressing variants of the genes encoding solvent resistance traits.

In other embodiments, one can employ a screening strategy to identify those recombinant polynucleotides that encode polypeptides that confer improved solvent resistance. For example, one can screen based on the in vivo expression of a reporter gene, such as those encoding fluorescent proteins (exemplified by the green fluorescent protein, GFP). Preferably, for the purpose of detecting the best solvent resistant genes under essentially stationary growth phase conditions, those reporter genes are used which display their function in a fashion dependent on availability of intracellular reducing pools, such as NADH and NADPH, and essentially unimpaired ribosomal biosynthesis of proteins.

Such genes and can be exemplified by several bacterial luciferase gene clusters (lux) which contain not only luciferase components, but also all polypeptides required for in-vivo regeneration of the aldehyde substrate for luciferase.

A variety of methods can be used to detect and to pick or to enrich for the clones with the most efficient solvent resistant traits as judged by display of the properties associated with the in-vivo reporter genes. These methods include, for example, fluorescence activating cell sorting of liquid cell suspensions (e.g., cells that express GFP) and CCD camera imaging of individual colonies grown on a solid(ified) medium (e.g., for cells that express lux).

If additional improvement in solvent resistance is desired, one can carry out a series of cycles of iterative DNA shuffling and selection by growing the cells in the presence of the organic solvent. Concentrations of the solvents used for selective growth conditions are incrementally increased after each round of recursive mode DNA shuffling in order to provide more stringent selective pressure for those organisms expressing solvent resistance genes.

For use in a high throughput screening protocol, the increase in the solvent resistance to a particular compound of interest and relevance to the biocatalytic synthesis of interest can also be directly measured by administering a radioactively labeled compound and determining relative distribution of radioactivity between cell biomass and extracellular medium components, similar to the method described by Ramos et al., *J. Bacteriol.* 180:3323–3329 (1998).

G. Bioreactors

In another aspect, the invention provides a bioreactor system for carrying out biotransformations using the improved polypeptides of the invention. The bioreactor includes: (a) an improved monooxygenase polypeptide of the invention; (b) a redox partner source; (c) oxygen; and (d) a substrate for oxidation.

In a preferred embodiment, the monooxygenase polypeptide is an arene monooxygenase polypeptide.

In another preferred embodiment, the bioreactor further includes another useful polypeptide, such as a transferase, ligase, dehydrogenase and the like. The additional useful polypeptide(s) can be co-expressed by a host cell also expressing the improved monooxygenase or it can be expressed by a host cell that does not express the improved monooxygenase. Moreover, each of the polypeptides incorporated into the reactor can be provided as a constituent of a whole cell preparation, a polypeptide extract or as a substantially pure polypeptide. The cells and/or polypeptides can be in suspension, solution or they can be immobilized on an insoluble matrix, bead or other particle. Additional considerations are discussed below. This discussion is intended as illustrative and not limiting. Other bioreactor formats, conditions, etc. will be apparent to those of skill in the art.

General growth conditions for culturing the particular organisms are obtained from depositories and from texts known in the art such as BERGEY'S MANUAL OF SYSTEMATIC BACTERIOLOGY, Vol. 1, N. R. Krieg, ed., Williams and Wilkins, Baltimore/London (1984).

For clarity of illustration, the discussion below focuses on the preferred conditions for the oxidation of an organic substrate using the polypeptides of the invention. It is understood that this focus is for the purpose of illustration and that similar conditions are applicable to pathways of the invention other than oxidation.

The nutrient medium for the growth of any oxidizing microorganism should contain sources of assimilable carbon and nitrogen, as well as mineral salts. Suitable sources of assimilable carbon and nitrogen include, but are not limited to, complex mixtures, such as those constituted by biological products of diverse origin, for example soy bean flour, cotton seed flour, lentil flour, pea flour, soluble and insoluble vegetable proteins, corn steep liquor, yeast extract, peptones and meat extracts. Additional sources of nitrogen are ammonium salts and nitrates, such as ammonium chloride, ammonium sulfate, sodium nitrate and potassium nitrate. Generally, the nutrient medium should include, but is not limited to, the following ions: $Mg^{2+}$, $Na^+$, $K^+$, $Ca^{2+}$, $NH_4^+$, $Cl^-$, $SO_4^{2-}$, $PO_4^{2-}$ and $NO_3^-$ and also ions of the trace elements such as Cu, Fe, Mn, Mo, Zn, Co and Ni. The preferred source of these ions are mineral salts.

If these salts and trace elements are not present in sufficient amounts in the complex constituents of the nutrient medium or in the water used it is appropriate to supplement the nutrient medium accordingly.

The microorganism employed in the process of the invention can be in the form of fermentation broths, whole washed cells, concentrated cell suspensions, polypeptide extracts, and immobilized polypeptides and/or cells. Preferably concentrated cell suspensions, polypeptide extracts, and whole washed cells are used with the process of the invention (S. A. White and G. W. Claus, *J. Bacteriology* 150:934–943 (1982)). Methods of immobilizing polypeptides and cells are well known in the art and include such techniques as microencapsulation, attachment to alginate beads, cross-linked polyurethane, starch particles, polyacrylamide gels and the use of coacervates, which are aggregates of colloidal droplets. In a presently preferred embodiment, the polypeptide and/or cell is immobilized onto a glass particles having a porous outer surface, such as that described in Dubin , et al., U.S. Pat. No. 5,922,531, issued Jul. 13, 1999.

Concentrated washed cell suspensions may be prepared as follows: the microorganisms are cultured in a suitable nutrient solution, harvested (for example by centrifuging) and suspended in a smaller volume (in salt or buffer solutions, such as physiological sodium chloride solution or aqueous solutions of potassium phosphate, sodium acetate, sodium maleate, magnesium sulfate, or simply in tap water, distilled water or nutrient solutions). The substrate is then added to a cell suspension of this type and the oxidation reaction according to the invention is carried out under the conditions described.

The conditions for oxidizing a substrate in growing microorganism cultures or fractionated cell extracts are advantageous for carrying out the process according to the invention with concentrated cell suspensions. In particular the temperature range is from about 0° C. to about 45° C. and the pH range is from about 2 to about 10. There are no special nutrients necessary in the process of the invention. More importantly, washed or immobilized cells can simply be added to a solution of substrate, without any nutrient medium present.

It is also possible to carry out the process according to the invention with polypeptide extracts or polypeptide extract fractions prepared from cells. The extracts can be crude extracts, such as obtained by conventional digestion of microorganism cells. Methods to break up cells include, but are not limited to, mechanical disruption, physical disruption, chemical disruption, and enzymatic disruption. Such means to break up cells include ultrasonic treatments, passages through French pressure cells, grindings with quartz sand, autolysis, heating, osmotic shock, alkali treatment, detergents, or repeated freezing and thawing.

If the process according to the invention is to be carried out with partially purified polypeptide extract preparations, the methods of protein chemistry, such as ultracentrifuging, precipitation reactions, ion exchange chromatography or adsorption chromatography, gel filtration or electrophoretic methods, can be employed to obtain such preparations. In order to carry out the reaction according to the invention with fractionated cell extracts, it may be necessary to add to the assay system additional reactants such as, physiological or synthetic electron acceptors, like $NAD^+$, $NADP^+$, methylene blue, dichlorophenolindophenol, tetrazolium salts and the like. When these reactants are used, they can be employed either in equimolar amounts (concentrations which correspond to that of the substrate employed) or in catalytic amounts (concentrations which are markedly below the chosen concentration of substrate). If, when using catalytic amounts, it is to be ensured that the process according to the invention is carried out approximately quantitatively, a system which continuously regenerates the reactant which is present only in a catalytic amount must also be added to the reaction mixture. This system can be, for example, a polypeptide which ensures reoxidation (in the presence of oxygen or other oxidizing agents) of an electron acceptor which is reduced in the course of the reaction according to the invention.

If nutrient media is used with intact microorganisms in a growing culture, nutrient media can be solid, semi-solid or liquid. Aqueous-liquid nutrient media are preferably employed when media is used. Suitable media and suitable conditions for cultivation include known media and known conditions to which substrate can be added.

The substrate to be oxidized in the process of the invention can be added to the base nutrient medium either on its own or as a mixture with one or more oxidizable compounds. Additional oxidizable compounds which can be used include polyols, such as sorbitol or glycerol.

If one or more oxidizable compounds are added to the nutrient solution, the substrate to be oxidized can be added either prior to inoculation or at any desired subsequent time (between the early log phase and the late stationary growth phase). In such a case the oxidizing organism is preferably pre-cultured with the oxidizable compounds. The inoculation of the nutrient media is effected by a variety of methods including slanted tube cultures and flask cultures.

Contamination of the reaction solution should be avoided. To avoid contamination, sterilization of the nutrient media, sterilization of the reaction vessels and sterilization of the air required for aeration is preferably undertaken. It is possible to use, for example, steam sterilization or dry sterilization for sterilization of the reaction vessels. The air and the nutrient media can likewise be sterilized by steam or by filtration. Heat sterilization of the reaction solution containing the substrate is also possible.

The process of the invention can be carried out under aerobic conditions using shake flasks or aerated and agitated tanks. Preferably, the process is carried out by the aerobic submersion procedure in tanks, for example in conventional fermentors. It is possible to carry out the process continuously or with batch or fed batch modes, preferably the batch mode.

It is advantageous to ensure that the microorganisms are adequately brought into contact with oxygen and the substrate. This can be effected by several methods including shaking, stirring and aerating.

If foam occurs in an undesired amount during the process, chemical foam control agents, such as liquid fats and oils, oil-in-water emulsions, paraffins, higher alcohols (such as octadecanol), silicone oils, polyoxyethylene compounds and polyoxypropylene compounds, can be added. Foam can also be suppressed or eliminated with the aid of mechanical devices.

H. Kits

Also provided is a kit or system utilizing any one of the selection strategies, materials, components, methods or substrates hereinbefore described. Kits will optionally additionally include instructions for performing methods or assays, packaging materials, one or more containers which contain assay, device or system components, or the like.

In an additional aspect, the present invention provides kits embodying the methods and apparatus herein. Kits of the invention optionally include one or more of the following: (1) a shuffled component as described herein; (2) instructions for practicing the methods described herein, and/or for operating the selection procedure herein; (3) one or more monooxygenase assay component; (4) a container for holding monooxygenase nucleic acids or polypeptides, other nucleic acids, transgenic plants, animals, cells, or the like and, (5) packaging materials.

In another preferred embodiment, the kit provides a library of improved P-450s, that have been produced by shuffling for improved stability, ease of handling, etc. The polypeptides in this library have catalytic activities that are substantially identical to those P-450 found in microsome preparations used to screen drugs and other xenobiotic compounds.

In a further embodiment, the present invention provides for the use of any component or kit herein, for the practice of any method or assay herein, and/or for the use of any apparatus or kit to practice any assay or method herein.

In yet another embodiment, the kit of the invention includes one or more improved monooxygenase polypeptides of the invention. In a preferred embodiment, the kit includes a library of improved monooxygenase polypeptides.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A method for obtaining a polynucleotide that encodes an improved polypeptide comprising monooxygenase (MO) activity, wherein said improved polypeptide has more than one improved property over a naturally occurring monooxygenase polypeptide, said method comprising:

(a) recombining a plurality of parental polynucleotides to produce a library of recombinant polynucleotides encoding recombinant monooxygenase polypeptides;

(b) screening said library to identify a recombinant polynucleotide that encodes an improved recombinant monooxygenase polypeptide that has enhanced stability in presence of peroxides and another property improved over said naturally occurring monooxygenase polypeptide, (c) recovering the recombinant polynucleotide that encodes the improved recombinant monooxygenase polypeptide identified in (b); and, (d) repeating steps (a, (b) and (c) using the recombinant polynucleotide recovered in step (c) as one of the plurality of parental polynucleotides in repeated step (a).

2. The method of claim 1 wherein said peroxide is hydrogen peroxide.

3. The method of claim 1, wherein said monooxygenase is a P450 enzyme.

4. The method of claim 1, wherein in said screening step, said another property improved over said naturally occurring monooxygenase polypeptide, is enhanced enantioselectivity.

5. A method for obtaining a polynucleotide that encodes an improved polypeptide comprising monooxygenase activity wherein said improved polypeptide has more than one improved property over a naturally occurring monooxygenase polypeptide, said method comprising:

(a) recombining a plurality of parental polynucleotides, at least one of which has monooxygenase activity, to produce a library of recombinant polynucleotides encoding recombinant monooxygenase polypeptides;

(b) screening said library to identify a recombinant polynucleotide that encodes an improved recombinant monooxygenase polypeptide that has enhanced enantioselectivity and another improved property over said naturally occurring monooxygenase polypeptide, (c) recovering the recombinant polynucleotide that encodes the improved recombinant monooxygenase polypeptide identified in step (b); and, (d) repeating steps (a), (b) and (c) using the recombinant polynucleotide recovered in step (c) as one of the plurality of parental polynucleotides in repeated step (a).

6. The method of claim 5, where in said screening step further comprises screening said library to identify a recombinant polynucleotide that encodes an improved recombinant monooxygenase polypeptide that has enhanced stability in the presence of peroxides over said naturally occurring monooxygenase polypeptide.

7. The method of claim 6 wherein said peroxide is hydrogen peroxide.

8. The method of claim 7, wherein said monooxygenase is a P450 enzyme.

9. The method of claim 5, wherein said enhanced enantioselectivity is for the production of a secondary alcohol.

* * * * *